United States Patent
Locke et al.

(10) Patent No.: US 12,344,642 B2
(45) Date of Patent: *Jul. 1, 2025

(54) VARIANT SURVIVIN VACCINE FOR TREATMENT OF MYELOMA

(71) Applicants: H. LEE MOFFITT CANCER CENTER AND RESEARCH INSTITUTE, INC., Tampa, FL (US); THE WISTAR INSTITUTE OF ANATOMY AND BIOLOGY, Philadelphia, PA (US)

(72) Inventors: Frederick L. Locke, Lutz, FL (US); Dario Altieri, Philadelphia, PA (US); Scott Antonia, Land O'Lakes, FL (US); Claudio Anasetti, Saint Petersburg, FL (US); Dmitry Gabrilovich, Villanova, PA (US)

(73) Assignees: H. LEE MOFFITT CANCER CENTER AND RESEARCH INSTITUTE, INC., Tampa, FL (US); THE WISTAR INSTITUTE OF ANATOMY AND BIOLOGY, Philadelphia, PA (US)

( * ) Notice: Subject to any disclaimer, the term of this patent is extended or adjusted under 35 U.S.C. 154(b) by 741 days.

This patent is subject to a terminal disclaimer.

(21) Appl. No.: 17/451,176

(22) Filed: Oct. 18, 2021

(65) Prior Publication Data
US 2022/0106370 A1    Apr. 7, 2022

Related U.S. Application Data

(60) Division of application No. 16/548,989, filed on Aug. 23, 2019, now Pat. No. 11,149,072, which is a continuation of application No. 15/568,967, filed as application No. PCT/US2016/031390 on May 7, 2016, now Pat. No. 10,414,810.

(60) Provisional application No. 62/158,341, filed on May 7, 2015.

(51) Int. Cl.
| | | |
|---|---|---|
| C07K 14/47 | (2006.01) | |
| A61K 40/19 | (2025.01) | |
| A61K 40/24 | (2025.01) | |
| A61K 40/42 | (2025.01) | |
| A61P 35/00 | (2006.01) | |

(52) U.S. Cl.
CPC .......... *C07K 14/4703* (2013.01); *A61K 40/19* (2025.01); *A61K 40/24* (2025.01); *A61K 40/424* (2025.01); *A61P 35/00* (2018.01); *C07K 14/4702* (2013.01); *A61K 2239/48* (2023.05)

(58) Field of Classification Search
CPC ............ C07K 14/4703; C07K 14/4702; A61K 39/00115; A61K 2039/5154
See application file for complete search history.

(56) References Cited

U.S. PATENT DOCUMENTS

| | | |
|---|---|---|
| 2003/0100525 A1 | 5/2003 | Altieri |
| 2004/0192631 A1 | 9/2004 | Xiang et al. |
| 2006/0035837 A1 | 2/2006 | Altieri et al. |
| 2011/0020373 A1 | 1/2011 | Saxon et al. |
| 2013/0142761 A1 | 6/2013 | Kaplan |
| 2015/0050304 A1 | 2/2015 | Wang et al. |

FOREIGN PATENT DOCUMENTS

| | | |
|---|---|---|
| EP | 1931377 | 7/2014 |
| WO | WO 2014/022138 | 2/2014 |

OTHER PUBLICATIONS

Allred, D.C. et al. "Prognostic and predictive factors in breast cancer by immunohistochemical analysis," *Mod Pathol*, 1998; 11:155-68.

Altieri, D.C. et al. "Survivin, versatile modulation of cell division and apoptosis in cancer," *Oncogene*, 2003; 22:8581-9.

Ambrosini, G. et al. "A novel anti-apoptosis gene, survivin, expressed in cancer and lymphoma," *Nat Med*, 1997; 3:917-21.

Andersen, M.H et al. "Identification of a cytotoxic T lymphocyte response to the apoptosis inhibitor protein survivin in cancer patients," *Cancer research*, 2001; 61:869-72.

Andersen, M.H. et al. "The universal character of the tumor-associated antigen survivin," *Clin Cancer Res*, 2007; 13:5991-4.

Attal, M. et al. "Randomized trial experience of the Intergroupe Francophone du Myelome," *Semin Hematol*, 2001; 38:226-30.

Barlogie, B. et al. "Treatment of multiple myeloma," *Blood*,2004; 103:20-32.

Becker, J.C. et al. "Survivin-specific T-cell reactivity correlates with tumor response and patient survival: a phase-II peptide vaccination trial in metastatic melanoma," *Cancer Immunol Immunother*, 2012; 61:2091-103.

Beyer, M. et al. "In vivo peripheral expansion of naive CD4+ CD25high FoxP3+ regulatory T cells in patients with multiple myeloma," *Blood*, 2006;107:3940-9.

Bonanno, G. et al. "Indoleamine 2,3-dioxygenase 1 (IDO1) activity correlates with immune system abnormalities in multiple myeloma," *Journal of Translational Medicine*, 2012;10:247.

Brody, J.D. et al. "Immunotransplantation preferentially expands T-effector cells over T-regulatory cells and cures large lymphoma tumors," *Blood*, 2009; 113:85-94.

Brown, R. et al. "B7+ T cells in myeloma: an Acquired Marker of Prior Chronic Antigen Presentation," *Leuk Lymphoma*, 2004; 45:363-71.

Brown, R.D. et al. "The expression of T cell related costimulatory molecules in multiple myeloma," *Leuk Lymphoma*, 1998; 31:379-84.

(Continued)

*Primary Examiner* — Elly-Gerald Stoica
(74) *Attorney, Agent, or Firm* — SALIWANCHIK, LLOYD & EISENSCHENK

(57) ABSTRACT

The invention concerns a variant (double mutant form) of the survivin polypeptide; nucleic acid molecules encoding the survivin variant; antigen presenting cells (APCs) such as dendritic cells, or APC precursors, comprising the variant survivin polypeptide or encoding nucleic acid sequence; and methods for treating a malignancy, such as myeloma, or for inducing an immune response, utilizing a variant survivin polypeptide, nucleic acid molecule, or APC.

12 Claims, 23 Drawing Sheets
Specification includes a Sequence Listing.

(56) References Cited

OTHER PUBLICATIONS

Casati, C. et al. "The apoptosis inhibitor protein survivin induces tumor-specific CD8+ and CD4+ T cells in colorectal cancer patients," *Cancer Res*, 2003;63:4507-15.
Chang, C.C. et al. "Tetra-O-methyl nordihydroguaiaretic acid induces growth arrest and cellular apoptosis by inhibiting Cdc2 and survivin expression," *Proceedings of the National Academy of Sciences of the United States of America*, 2004; 101:13239-44.
Cheung, C. et al. "Survivin—biology and potential as a therapeutic target in oncology," *Onco Targets and Therapy*, 2013, 6:1453-1462.
Cong, X.L. et al. "Survivin and leukemia," *Int J Hematol*, 2004; 80:232-8.
Corthay, A. et al. "Primary antitumor immune response mediated by CD4+ T cells," *Immunity*, 2005; 22:371-83.
De Haart, S.J. et al. "Accessory cells of the microenvironment protect multiple myeloma from T-cell cytotoxicity through cell adhesion-mediated immune resistance," *Clin Cancer Res*, 2013; 19:5591-601.
Dhodapkar, K.M. et al. "Dendritic cells mediate the induction of polyfunctional human IL17-producing cells (Th17-1 cells) enriched in the bone marrow of patients with myeloma," *Blood*, 2008; 112:2878-85.
Favaloro, J. et al. "Myeloid derived suppressor cells are numerically, functionally and phenotypically different in patients with multiple myeloma," *Leuk Lymphoma*, 2014:1-8.
Fields, A.C. et al. "Survivin expression in hepatocellular carcinoma: correlation with proliferation, prognostic parameters, and outcome," *Mod Pathol*, 2004; 17:1378-85.
Fields, P.E. et al. "Blocked Ras activation in anergic CD4+ T cells," *Science*, 1996; 271:1276-8.
Fukuda, S. et al. "Survivin, a cancer target with an emerging role in normal adult tissues," *Mol Cancer Ther*, 2006, 5(5):1087-1098.
Gabrilovich, D.I. "Combination of chemotherapy and immunotherapy for cancer: a paradigm revisited," *The lancet oncology*, 2007; 8:2-3.
Gerdemann, U. et al. "Cytotoxic T lymphocytes simultaneously targeting multiple tumor-associated antigens to treat EBV negative lymphoma," *Mol Ther*, 2011; 19:2258-68.
Gerdemann, U. et al. "Rapidly generated multivirus-specific cytotoxic T lymphocytes for the prophylaxis and treatment of viral infections," *Mol Ther*, 2012; 20:1622-32.
Gorgun, G.T. et al. "Tumor-promoting immune-suppressive myeloid-derived suppressor cells in the multiple myeloma microenvironment in humans," *Blood*, 2013; 121:2975-87.
Grube, M. et al. "CD8+ T cells reactive to survivin antigen in patients with multiple myeloma," *Clin Cancer Res*, 2007; 13:1053-60.
Han, S. et al. "Overcoming immune tolerance against multiple myeloma with lentiviral calnexin-engineered dendritic cells," *Mol Ther*, 2008; 16:269-79.
Hirschhorn-Cymerman, D. et al. "Induction of tumoricidal function in CD4+ T cells is associated with concomitant memory and terminally differentiated phenotype," *J Exp Med*, 2012; 209:2113-26.
Hirschowitz, E.A. et al. "Immunization of NSCLC patients with antigen-pulsed immature autologous dendritic cells," *Lung Cancer*, 2007; 57:365-72.
Hirschowitz, E.A. et al. "Autologous dendritic cell vaccines for non-small-cell lung cancer," *J Clin Oncol*, 2004; 22:2808-15.
Hung, K. et al. "The central role of CD4(+) T cells in the antitumor immune response," *J Exp Med*, 1998;188:2357-68.
Idenoue, S. et al. "A potent immunogenic general cancer vaccine that targets survivin, an inhibitor of apoptosis proteins," *Clin Cancer Res*, 2005; 11:1474-82.
Kawasaki, H. et al. "Inhibition of apoptosis by survivin predicts shorter survival rates in colorectal cancer," *Cancer Res*, 1998; 58:5071-4.
Knauer, S.K. et al. "Survivin's dual role: an export's view," *Cell Cycle*, 2007; 6:518-21.
Levitsky, H.I. et al. "In vivo priming of two distinct antitumor effector populations: the role of MHC class I expression," *J Exp Med*, 1994; 179:1215-24.
Li, F. et al. "Control of apoptosis and mitotic spindle checkpoint by survivin," *Nature*, 1998; 396:580-4.
Li, J. et al. "Expression and clinical significance of survivin in bone marrow cells of multiple myeloma patients," *Chinese Journal of Cancer*, 2005; 24:1522-6.
Lim, S.H. et al. "Distinct T-cell clonal expansion in the vicinity of tumor cells in plasmacytoma," *Cancer*, 2001; 91:900-8.
Liu, G. et al. "Sensitization of malignant glioma to chemotherapy through dendritic cell vaccination," *Expert review of vaccines*, 2006; 5:233-47.
Locke, F.L. et al. "Immunotherapy strategies for multiple myeloma: the present and the future," *Immunotherapy*, 2013; 5:1005-20.
Locke F.L. et al. "Conditional deletion of PTEN in peripheral T cells augments TCR-mediated activation but does not abrogate CD28 dependency or prevent anergy induction," *J Immunol*, 2013; 191:1677-85.
Locke, F. et al. "Survivin-specific CD4+ T cells are decreased in patients with survivin-positive myeloma," *J. Immunother. Cancer*, 2015, 3:20, 11 pages.
Mesri, M. et al. "Cancer gene therapy using a survivin mutant adenovirus," *J. of Clin. Invest*, 2001, 108:981-90.
Mori, A. et al. "Expression of the antiapoptosis gene survivin in human leukemia," *Int J Hematol*, 2002; 75:161-5.
Nagaraj, S. et al. "Dendritic cell-based full-length survivin vaccine in treatment of experimental tumors," *J Immunother*, 2007; 30:169-79.
Nakagawa, Y. et al. "IAP family protein expression correlates with poor outcome of multiple myeloma patients in association with chemotherapy-induced overexpression of multidrug resistance genes," *Am J Hematol*, 2006; 81:824-31.
Nakahara, T. et al. "YM155, a novel small-molecule survivin suppressant, induces regression of established human hormone-refractory prostate tumor xenografts," *Cancer research*, 2007; 67:8014-21.
Noonan, K. et al. "A novel role of IL-17-producing lymphocytes in mediating lytic bone disease in multiple myeloma," *Blood*, 2010; 116:3554-63.
Palucka, K. et al. "Cancer immunotherapy via dendritic cells," *Nature Reviews Cancer*, 2012, 12:265-277.
Palumbo, A. et al. "Melphalan 200 mg/m(2) versus melphalan 100 mg/m(2) in newly diagnosed myeloma patients: a prospective, multicenter phase 3 study," *Blood*, 2010;115:1873-9.
Palumbo, A. et al. "Lenalidomide: a new therapy for multiple myeloma," *Cancer Treat Rev*, 2008; 34:283-91.
Pennati, M. et al. "Targeting surviving in cancer therapy: fulfilled promises and open questions," *Carcinogenesis*, 2007, 28(6):1133-1139.
Piesche, M. et al. "Identification of a promiscuous HLA DR-restricted T-cell epitope derived from the inhibitor of apoptosis protein surviving," *Human Immunology*, 2007; 68:572-6.
Pisarev, V. et al. "Full-length dominant-negative survivin for cancer immunotherapy" *Clinical Cancer Research*, 2003, 17:6523-6533.
Prabhala, R.H. et al. "Dysfunctional T regulatory cells in multiple myeloma," *Blood*, 2006; 107:301-4.
Prabhala, R.H. et al. "Elevated IL-17 produced by TH17 cells promotes myeloma cell growth and inhibits immune function in multiple myeloma," *Blood*, 2010; 115:5385-92.
Ramachandran, I.R. et al. "Myeloid-derived suppressor cells regulate growth of multiple myeloma by inhibiting T cells in bone marrow," *J Immunol*, 2013; 190: 3815-23.
Ramos, C.A. et al. "Human papillomavirus type 16 E6/E7-specific cytotoxic T lymphocytes for adoptive immunotherapy of HPV-associated malignancies," *J Immunother*, 2013; 36:66-76.
Rapoport, A.P. et al. "Combination immunotherapy using adoptive T-cell transfer and tumor antigen vaccination on the basis of hTERT and survivin after ASCT for myeloma," *Blood*, 2011; 117:788-97.
Rapoport, A.P. et al. "Restoration of immunity in lymphopenic individuals with cancer by vaccination and adoptive T-cell transfer," *Nat Med*, 2005; 11:1230-7.
Rawstron, A.C. "Minimal residual disease detection in myeloma: no more molecular remissions?" *Haematologica*, 2005; 90:1300B.

(56) References Cited

OTHER PUBLICATIONS

Richardson, P.G. et al. "Bortezomib in the front-line treatment of multiple myeloma," *Expert Rev. Anticancer Ther*, 2008; 8:1053-72.
Romagnoli, M. et al. "Significant impact of survivin on myeloma cell growth," *Leukemia*, 2007; 21:1070-8.
Rosenberg, S.A. et al. "Cancer immunotherapy: moving beyond current vaccines," *Nature Medicine*, 2004; 10:909-15.
Rosenblatt, J. et al. "PD-1 blockade by CT-011, anti-PD-1 antibody, enhances ex vivo T-cell responses to autologous dendritic cell/myeloma fusion vaccine," *J Immunother*, 2011; 34:409-18.
Schmidt, S. et al. "Survivin is a Shared Tumor-Associated Antigen Expressed in a Broad Variety of Malignancies and Recognized by Specific Cytotoxic T Cells," *Blood*, 2003,102:571-576.
Schmitz, M. et al. "Generation of survivin-specific CD8+ T effector cells by dendritic cells pulsed with protein or selected peptides," *Cancer Res*, 2000; 60:4845-9.
Shain, K.H. et al. "Environmental-mediated drug resistance: a target for multiple myeloma therapy," *Expert review of hematology*, 2009; 2:649-62.
Stauber, R.H. et al. "Nuclear and cytoplasmic survivin: molecular mechanism, prognostic, and therapeutic potential," *Cancer Res*, 2007; 67:5999-6002.
Swana, H.S. et al. "Tumor content of the antiapoptosis molecule survivin and recurrence of bladder cancer," *N Engl J Med*, 1999; 341:452-3.
Tamura, H. et al. "Marrow stromal cells induce B7-H1 expression on myeloma cells, generating aggressive characteristics in multiple myeloma," *Leukemia*, 2013; 27:464-72.
Tanaka, K. et al. "Expression of survivin and its relationship to loss of apoptosis in breast carcinomas," *Clin Cancer Res*, 2000; 6:127-34.
Tanaka, M. et al. "Induction of HLA-DP4-restricted anti-survivin Th1 and Th2 responses using an artificial antigen-presenting cell," *Clin Cancer Res*, 2011; 17:5392-401.
Tolcher, A.W. et al. "A Phase I and Pharmacokinetic Study of YM155, A Small Molecule Inhibitor of Survivin," *Journal of Clinical Oncology*; 2008; 26(32):5198-5208.

Veerapathran, A. et al. "Ex vivo expansion of human Tregs specific for alloantigens presented directly or indirectly," *Blood*, 2011; 118:5671-80.
Wang, X.F. et al. "Comprehensive analysis of HLA-DR- and HLA-DP4-restricted CD4+ T cell response specific for the tumor-shared antigen survivin in healthy donors and cancer patients," *J Immunol*, 2008; 181:431-9.
Wang, Y-Q. et al. "Enhancement of survivin-specific anti-tumor immunity by adenovirus prime protein-boost immunity strategy with DDA/MPL adjuvant in a murine melanoma model," *International Immunopharmacology*, 2013, 17:9-17.
Weber, G. et al. "Generation of tumor antigen-specific T cell lines from pediatric patients with acute lymphoblastic leukemia—implications for immunotherapy," *Clin Cancer Res*, 2013;19:5079-91.
Widenmeyer, M. et al. "Promiscuous survivin peptide induces robust CD4+ T-cell responses in the majority of vaccinated cancer patients," *Int J Cancer*, 2012; 131:140-9.
Xiang, R. et al. "A DNA vaccine targeting survivin combines apoptosis with suppression of angiogenesis in lung tumor eradication," *Cancer Res*, 2005; 65:553-61.
Zhang, R. et al. "A survivin double point mutant has potent inhibitory effect on the growth of hepatocellular cancer cells," *Cancer Biology & Therapy*, 2008, 7(4):547-554.
Zheng, Y et al. "Transcriptional regulator early growth response gene 2 (Egr2) is required for T cell anergy in vitro and in vivo," *J Exp Med*, 2012; 209:2157-63.
Rech, J. et al. "Phase I study of anti-CD25 mab daclizumab to deplete regulatory T cells prior to telomerase/survivin peptide vaccination in patients (pts) with metastitic breast cancer (MBC)," *2010 American Society of Clinical Oncology Annual Meeting*; 2508, Jun. 8, 2010; Abstract.
Rech, J. et al. "CD25 Blockage Depletes and Selectively Reprograms Regulatory T Cells in Concert with Immunotherapy in Cancer Patients," *Science Transitional Medicine*, 2012; 4(134):134ra62.
International Search Report/Written Opinion for WO2016/179573, dated Aug. 19, 2016, pp. 1-18.
Bot, A. et al. "Repositioning therapeutic cancer vaccines in the dawning era of potent immune interventions" *Expert Review of Vaccines*, 2013, 12(10):1291-1234.
Tan, S. et al. "Cancer immunotherapy: Pros, cons and beyond" *Biomed. & Pharmacother.*, 2020, 124:109821 (11 pages).

VARIANT SURVIVIN VACCINE FOR TREATMENT OF MYELOMA

CROSS-REFERENCE TO RELATED APPLICATIONS

The present application is a divisional of U.S. application Ser. No. 16/548,989, filed Aug. 23, 2019, which is a continuation of U.S. application Ser. No. 15/568,967, filed Oct. 24, 2017, which is the National Stage of International Application No. PCT/US2016/031390, filed May 7, 2016, which claims the benefit of U.S. Provisional Application Ser. No. 62/158,341, filed May 7, 2015, which is hereby incorporated by reference herein in its entirety, including any figures, tables, nucleic acid sequences, amino acid sequences, or drawings.

GOVERNMENT SUPPORT

This invention was made with government support under grant number CA078810 awarded by the National Institutes of Health. The government has certain rights in the invention.

BACKGROUND OF THE INVENTION

Survivin is a small protein and tumor associated antigen expressed in multiple myeloma. Survivin normally functions as an apoptosis inhibitor, via spindle microtubule and mitotic checkpoint regulation (1). It is a potential target for immunotherapy since it is highly expressed in many cancers (2-4), it is linked to worse prognosis in both solid and hematologic tumors, and it is undetectable in almost all normal adult tissues (5). Survivin is overexpressed in myeloma cell lines and its expression in primary myeloma cells is associated with poor prognosis, disease progression, and drug resistance (6, 7).

CD8+ T cells specific for survivin have been demonstrated in myeloma patients (8), and survivin-specific CTL responses were generated in vivo in tumor-bearing mice (9-11). For malignant melanoma patients receiving a MHC class I restricted peptide vaccine against survivin, both response to therapy and overall survival were associated with a CD8+ T cell response against survivin (12). Present knowledge of human immune response against survivin is almost entirely based upon the induction of cytotoxic CD8+ T cell responses using vaccines or clonotype analysis using single HLA-Class I peptides. Little is known about important CD4+ helper T cell responses against survivin, which are essential for an optimal anti-tumor immune response (13, 14). Cancer patients can have survivin-specific CD4+ T cells (15-17) and robust CD4+ responses may be generated with survivin HLA-class II restricted peptide vaccines in cancer patients (18, 19). CD4+ T cells can reject tumors in the absence of CD8+ T cells (20) and provide primary anti-tumor immune responses important for immunosurveillance (21). The spontaneous CD4+ response against survivin in myeloma patients has not been characterized, and must be understood to identify vaccine strategies against aggressive survivin expressing myeloma.

Prior evaluation of T cell immune responses against survivin, and most therapeutic survivin cancer vaccines, has relied upon identification of T cells specific for HLA restricted peptides. This strategy has several limitations. Many peptides can be generated from the entire protein. Each peptide is restricted by one or few HLA molecules for presentation to immune cells and HLA molecules are encoded by 15 distinct genes that are the most polymorphic in the entire genome. Therefore, because HLA genes vary widely among people, the probability of one peptide inducing an immune response is low and the breadth of the response is extremely narrow. Survivin-derived peptide pools can overcome these limitations and allow study of the immune response against survivin (22).

BRIEF SUMMARY OF THE INVENTION

The present invention concerns variant survivin polypeptides, nucleic acid molecules encoding the variant survivin polypeptides, antigen presenting cells (APCs) comprising the variant survivin polypeptide or encoding nucleic acid sequence, and compositions containing any of the foregoing, useful as vaccines for the treatment of existing malignancies and preventing or delaying the onset of malignancies, and for inducing a desired immune response (e.g., a survivin-reactive CD4+ T cell response).

In one approach, APCs such as autologous dendritic cells may be generated from their precursors in bone marrow or peripheral blood mononuclear cells from the subject suffering from the malignancy, transfecting the cells with a nucleic acid to produce a variant survivin polypeptide, and then infusing the cells back into the subject. Advantageous, portions of the variant survivin polypeptide are presented by the APC. The APC-based vaccination can act as an antigen delivery vehicle as well as a potent adjuvant, resulting in anti-tumor immunity.

Accordingly, aspects of the invention are directed to (i) a variant survivin polypeptide, (ii) nucleic acid molecules encoding the polypeptides (and expression constructs comprising the nucleic acids), and (iii) APCs comprising the variant survivin polypeptide or nucleic acid sequence encoding a variant survivin polypeptide, wherein the variant survivin polypeptide comprises at least consecutive amino acids 16-87 (N-terminal zinc-binding baculovirus inhibitor of apoptosis protein repeat (BIR) domain) of the human wild-type survivin polypeptide (SEQ ID NO:1) modified to have an amino acid at position 34 which is other than threonine and an amino acid at position 84 which is other than cysteine, relative to the human wild-type survivin polypeptide, and wherein the variant survivin polypeptide:

(a) comprises a 142-amino acid sequence having at least 80% sequence identity to the human wild-type survivin polypeptide (SEQ ID NO:1), or (b) is a subsequence (fragment) of the human wild-type survivin polypeptide (SEQ ID NO:1).

In some embodiments, one or both of the amino acids at position 34 and at position 84 are nonpolar amino acids. In some embodiments, one or both of the amino acids at position 34 and at position 84 are alanine.

In some embodiments, the variant survivin polypeptide comprises a full-length mammalian wild-type survivin polypeptide having an amino acid at position 34 which is other than threonine, and an amino acid at position 84 which is other than cysteine, such as set forth as SEQ ID NO:2 or a mammalian homolog thereof.

In some embodiments, the variant survivin polypeptide comprises the full-length human wild-type survivin polypeptide having an amino acid at position 34 which is other than threonine, and an amino acid at position 84 which is other than cysteine, as set forth as SEQ ID NO:2.

In some embodiments, the variant survivin polypeptide further includes at least consecutive amino acids 6-10, consecutive amino acids 89-97 (linker region), and consecutive amino acids 97-141 (coiled coil domain) of the human wild-type survivin polypeptide (SEQ ID NO:1).

Another aspect of the invention concerns a composition comprising APCs of the invention; and a pharmaceutically acceptable carrier. The composition may include further components, such as an adjuvant or other anti-cancer agents, such as a chemotherapeutic or immunotherapeutic agent, or an antigen (e.g., a tumor-associated antigen).

Another aspect of the invention concerns a method for treating a malignancy, comprising administering to a subject in need of treatment an effective amount of antigen presenting cells of the invention. In some embodiments, the malignancy is myeloma.

BRIEF DESCRIPTION OF THE DRAWINGS

(FIG. 2A) Log-fraction plot of the LDA of survivin specific CD4+CD25− T cells both before and after expansion with DC:survivin. The slope represents log-active cell fraction, bold lines represent frequency estimates, and non-bold lines show 95% CIs based on the likelihood ratio test of single-hit model. One out of 44,907 cells were estimated to respond to the survivin peptide pool before expansion (Before). Separately, CD4+CD25− T cells from the same donor were expanded using DC:survivin and exogenous IL-2 for 12 days. Cells were collected, enumerated, and rested without cytokines for 2 days. Repeat LDA after expansion demonstrated enrichment for survivin specific T cells to 1 out of 383 (After), p<0.0001. The results are representative of 2 independent experiments from separate healthy donors. (FIG. 2B) LDA was validated by labeling un-stimulated CD4+CD25− T cells with CTV (cell trace violet) prior to expansion with DC:survivin and exogenous IL-2. After 12 days, T cells were flow sorted into CD4+ CTV− (replicated) and CD4+CTV+ (non-replicated), then rested for 2 days without cytokines. $2.5\times10^3$ CD4+ T cells were stimulated with DC:survivin or DC:HIV (irrelevant) peptide pool for 24 hours. *=p<0.05 by t test, error bars indicate the standard deviation. The results are representative of two independent experiments from separate healthy donors.

FIG. 3A: The survivin-reactive CD4+CD25− precursor frequency for 12 consecutive myeloma patients was determined. Myeloma patients survivin-reactive cells, as a % of total CD4+CD25− cells, were less than that of consecutive healthy donors (p=0.02, non-parametric t-test). FIGS. 3B-3C: Myeloma patient CD4+ CD25− cells were expanded using DC:survivin as described. The survivin-reactive cell frequency (FIG. 3B) and the total number of survivin-reactive cells (FIG. 3C) was significantly increased (graph shows results of 5 myeloma patients with survivin-reactive cells calculated by LDA both before and after peptide pool expansion). (Line=Mean, Box=25%-75% CI, Whiskers=minimum and maximum) *p<0.05 by non-parametric t-test.

FIG. 4A: CD138+ T cells were purified from myeloma patient bone marrow aspirates. mRNA transcripts for survivin were normalized to GAPDH. FIG. 4B: mRNA expression inversely correlates to the de-novo survivin-reactive CD4+CD25− T cell precursor frequency as calculated by LDA. (p=0.0028 and r=−1.0 by Spearman nonparametric correlation analysis).

FIGS. 5A-5B: An adenoviral construct was used to infect autologous myeloma patient DCs which leads to expression of a full-length mutant survivin protein. Patient CD4+CD25− T cell survivin-reactive frequency was calculated by LDA before and after 12 day co-culture with DC:ad-ms. The survivin vaccine increases both the frequency of survivin-reactive CD4+ cells (FIG. 5A) and the absolute number of survivin-reactive cells (FIG. 5B). *=p<0.05 by paired ratio t-test.

FIGS. 6-8 demonstrate that the adenoviral construct used in the study can be used to overexpress survivin in DCs. Dendritic cells were from healthy donor peripheral blood and infected with either control (Ad-CMV-GFP) or Ad-survivin (20,000 viral particles per cell) for 48 hr. Survivin was evaluated by Western Blot. MM lysate is a positive control showing survivin protein in multiple myeloma cells. FIG. 8 shows the results of another experiment similar to FIGS. 6 and 7, but for comparison with several different tumors were used as positive controls. PC9 and A549 are two lung carcinoma cell lines.

FIG. 11A: The survivin reactive CD4+CD25− precursor frequency for 12 consecutive myeloma patients was determined. Myeloma patients survivin reactive cells, as a % of total CD4+CD25−) cells were less than that of consecutive healthy donors (p=0.02, non-parametric t-test). FIG. 11B: CD138+ T cells were purified from myeloma patient bone marrow aspirates.

mRNA transcripts for survivin were normalized to GAPDH. mRNA expression inversely correlates to the survivin reactive CD4+CD25– T cell precursor frequency as calculated by LDA. (p=0.0028 and r=–1.0 by Spearman nonparametric correlation analysis).

Figure 12A:
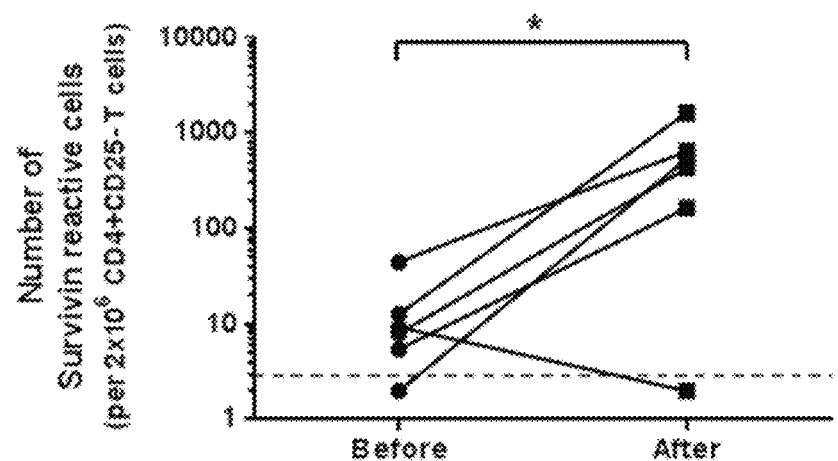
Figure 12B:
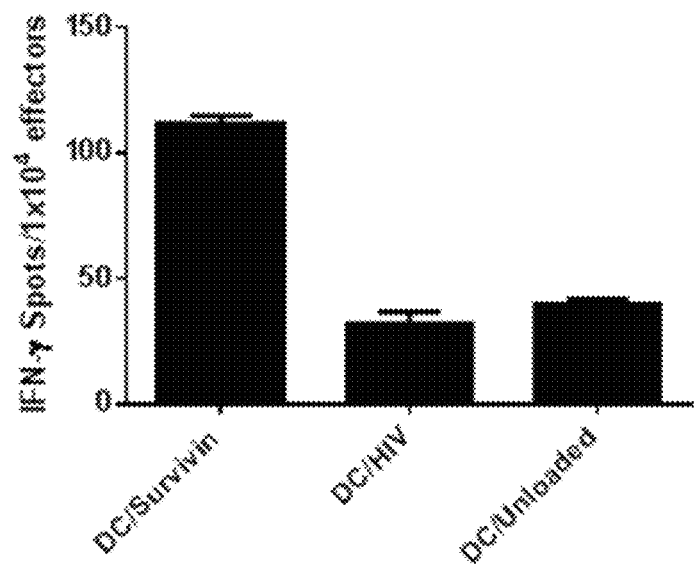

FIGS. 12A and 12B. A full length survivin protein vaccine expands survivin specific CD4+ cells even in patients with a low survivin reactive precursor frequency. FIG. 12A: An adenoviral construct was used to infect autologous myeloma patient DCs which leads to expression of a full length mutant survivin protein (mAd-surv). Patient CD4+CD25– T cell survivin reactive frequency was calculated using survivin peptide pool by LDA before and after 12 day co-culture with DC:ad-ms. The survivin vaccine increases both the frequency of survivin reactive CD4+ cells (not shown) and the absolute number of survivin reactive cells. *=p<0.05 by paired ratio t-test. FIG. 12B: After T cell stimulation using mAd-surv, T cells were collected, rested for 2 days, enumerated, and re-stimulated using autologous DCs loaded with survivin peptide pool, irrelevant protein (HIV) peptide pool, or unloaded DCs. Expanded cells exhibit survivin specificity.

Figure 13A:
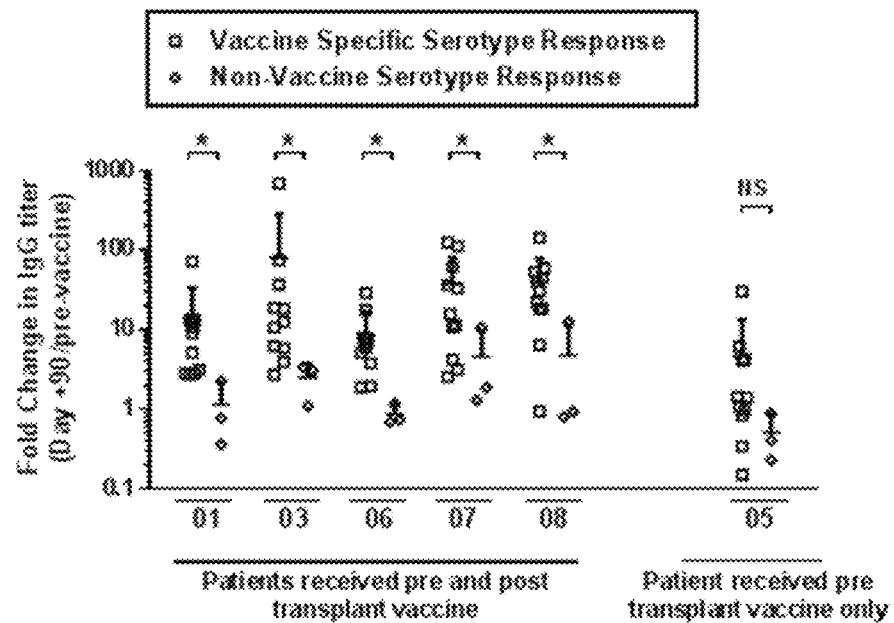
Figure 13B:
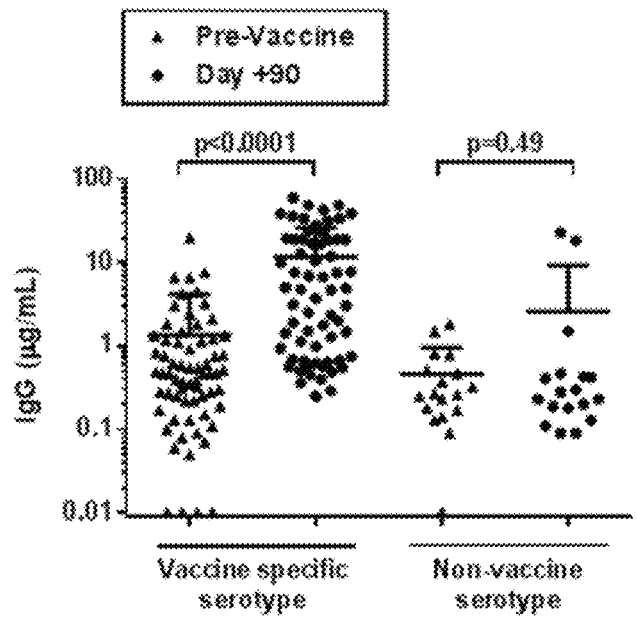

FIGS. 13A and 13B. Vaccination with PCV-13 elicits humoral immune responses against pneumococcal serotypes when administered pre-mobilization and again early post-transplant. FIG. 13A: The relative increase in pneumococcal serotype IgG (Day+90 after transplant/pre-vaccine) is plotted on the y axis. Pneumococcal 13-valent Conjugate Vaccine specific serotypes (open squares) are compared to serotypes not included in the vaccine (open diamonds) for each patient. *=p<0.05 by non-parametric t-test. NS=not significant. FIG. 13B: Absolute IgG levels for each of the pneumococcal serotypes, pre-vaccine (triangles) and day +90 post-transplant (circles). *=p<0.05 by non-parametric paired t-test.

Figure 14A:
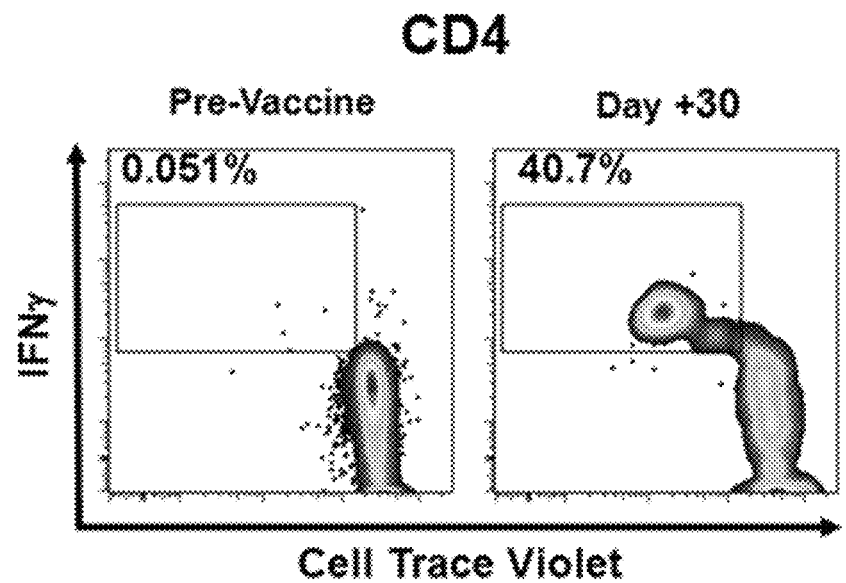
Figure 14B:
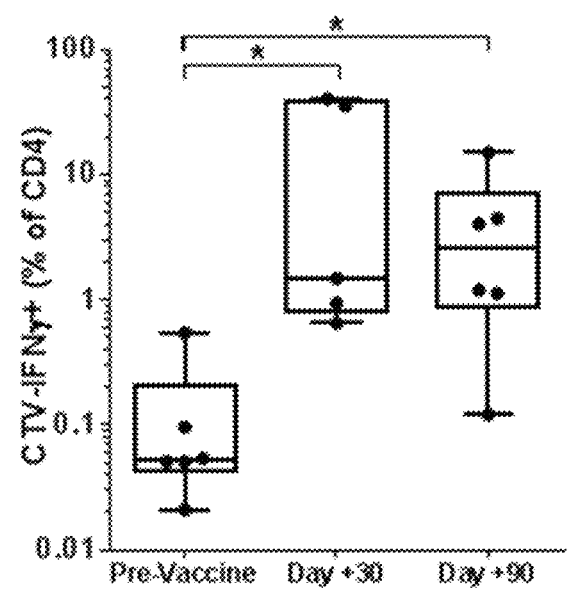
Figure 14C:
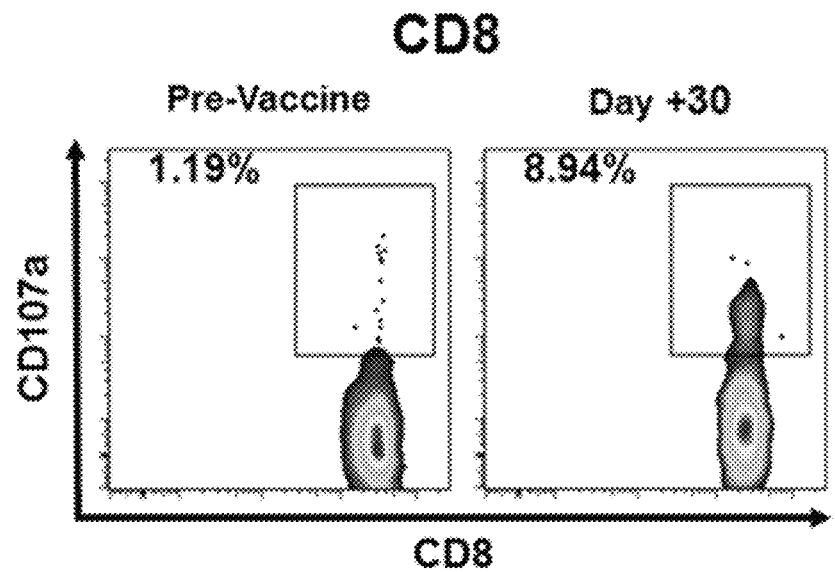
Figure 14D:
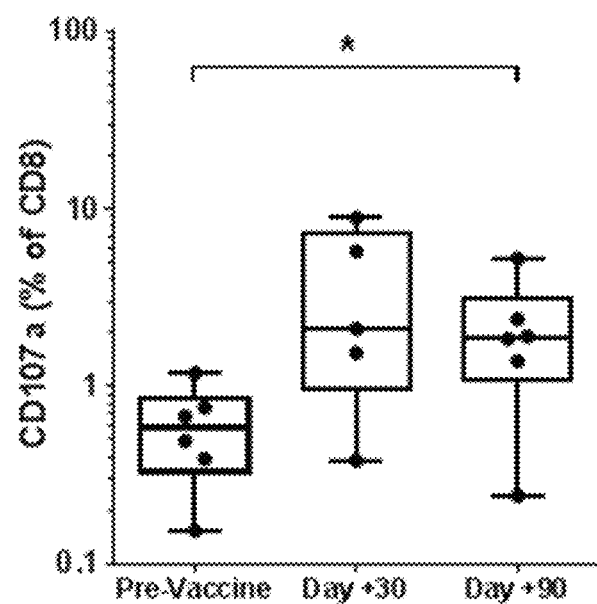

FIGS. 14A-14D. Vaccination with PCV-13 elicits cellular immune responses to the CRM197 protein. PBMCs were stained with cell trace violet then incubated with CRM197 or vehicle control as indicated in the methods. Cells were then harvested and stained for flow cytometry. FIG. 14A: Flow plot was first gated upon live, single cell, CD3+, CD4+ and shows the best CD4+CTV-IFN-gamma+ response at day +30. FIG. 14B: The % of CD4+ cells that divide and express intracellular IFN-gamma (CTV-IFNgamma+ as a % of live single cell CD4) is plotted for each patient (one dot for each patient) from pre-vaccine to post-transplant (day +30 and day +90). *=p<0.05 by non-parametric t-test. FIG. 14C: Flow plot was first gated upon live, single cell, CD3+, CD8+ and shows the best CD8+CD107a+ response at day +30. FIG. 14D: The % of CD8+ cells that express the cytotoxicity marker CD107a (CD107a+ as a % of live single cell CD8) is plotted for each patient (one dot for each patient) from pre-vaccine to post-transplant (day +30 and day +90). *=p<0.05 by non-parametric t-test.

Figure 15A:
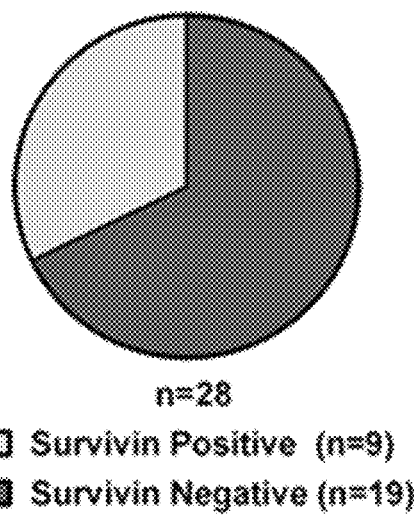
Figure 15B:
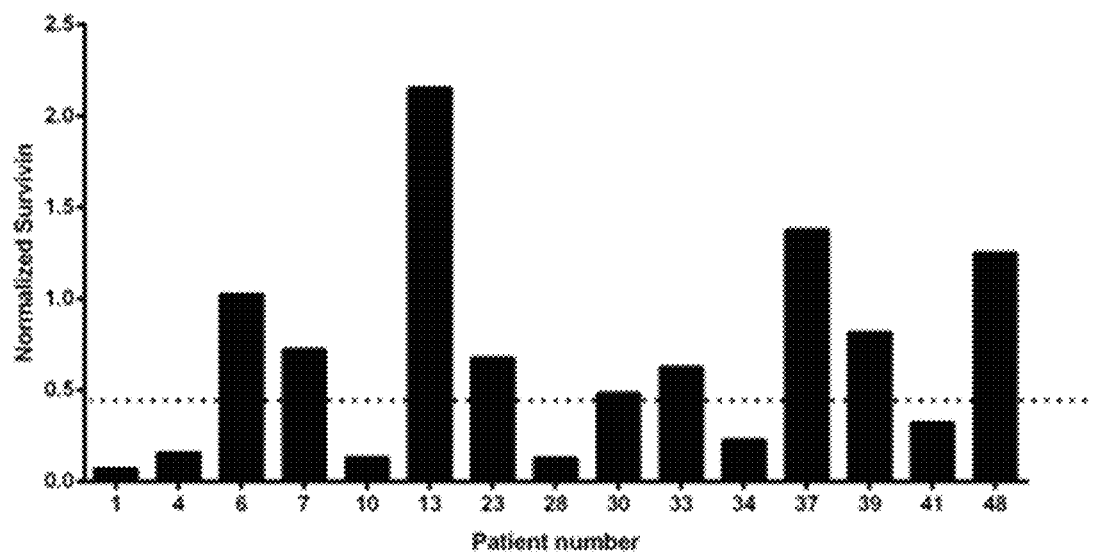
Figure 16A:
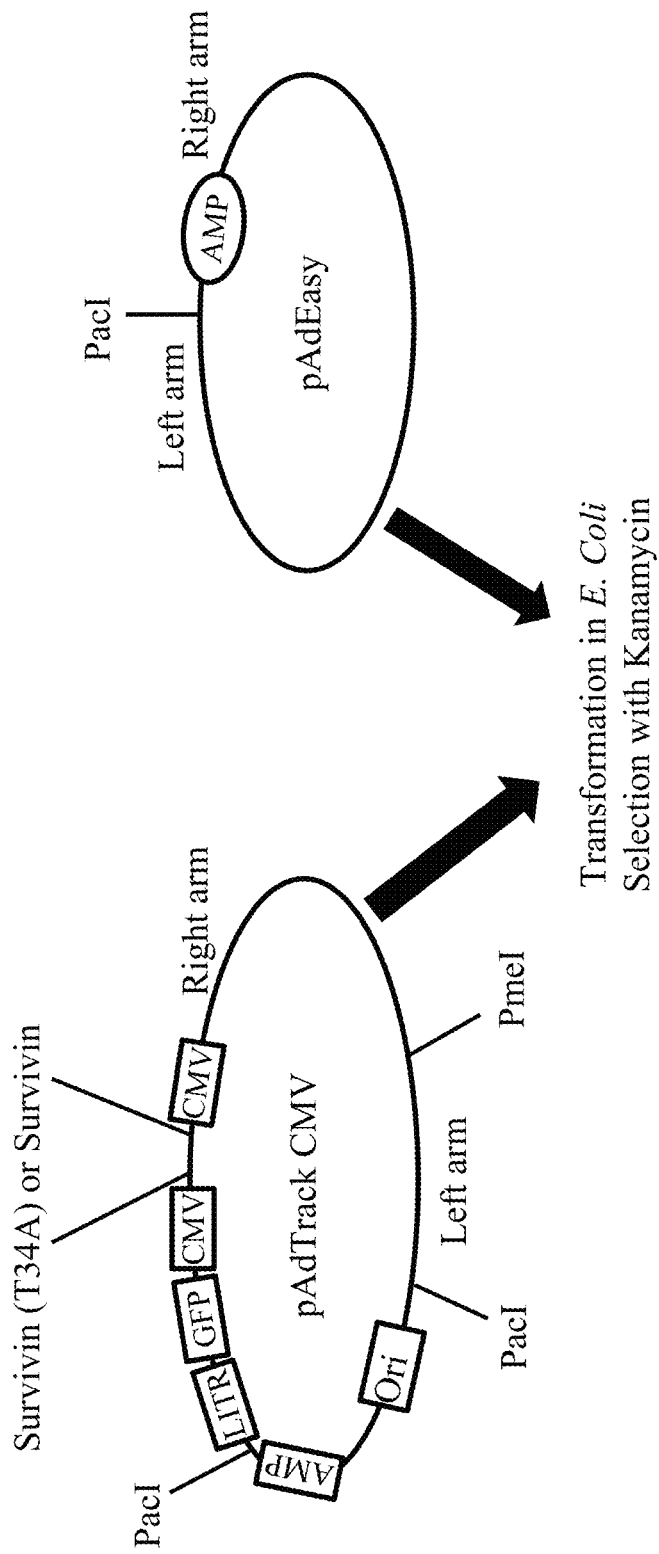
Figure 16B:
Figure 16C:
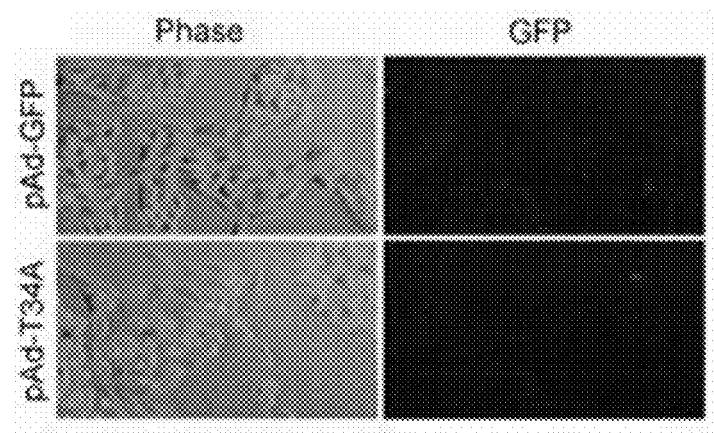
Figure 16D:
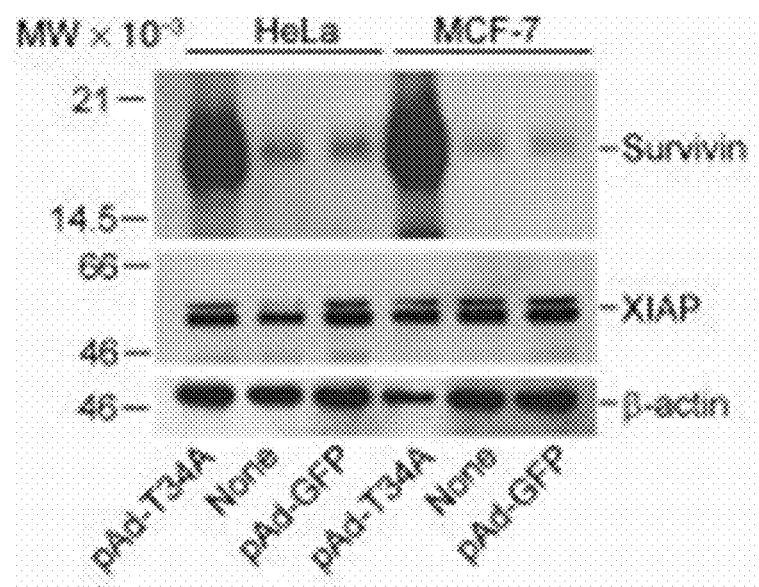

FIGS. 15A and 15B. Tumor survivin is expressed in myeloma patients' tumors after induction therapy. FIG. 15A: Survivin protein expression. Bone marrow biopsy specimens collected after induction chemotherapy and prior to autologous transplant were evaluated by immunohistochemistry for the presence of survivin protein. FIG. 15B: Survivin mRNA expression. CD138+ cells were purified from bone marrow aspirates collected after induction chemotherapy and prior to autologous transplant. PCR reveals survivin expression normalized against GAPDH expression. Dotted line represents the survivin expression (mean+2 standard deviations) in PBMCs from healthy donor controls.

FIGS. 16A-16D. Construction and expression of single mutant (T34A) pAd-survivin vectors. (FIG. 16A) Map of pAdTrack CMV and pAdEasy vectors. (FIG. 16B) GFP expression in transduced cultures. HeLa cells were infected with the indicated pAd vectors at moi of 50 for 8 hours, harvested after 48 hours, and analyzed by fluorescence microscopy. (FIG. 16C) Absence of replication-competent adenoviral particles. HeLa cells ($8\times10^4$) were infected with pAd-T34A or pAdGFP at moi of 1,250 and grown for 3 days at 37° C. Cell extracts were used to successively infect a second HeLa cell culture, and cells were analyzed by phase-contrast microscopy (Phase) or GFP expression (GFP) after an additional 2-day period. (FIG. 16D) Western blot analysis. Aliquots of HeLa or MCF-7 cells were infected with the indicated pAd vectors at MOI of 50, harvested after 48 hours at 37° C., and protein normalized extracts were analyzed by Western blotting with an Ab to survivin, XIAP, or control β-actin followed by chemiluminescence. Molecular-weight markers in kilodaltons are shown on the left. LITR, left-hand inverted terminal repeat; MW, molecular weight.

Figure 17:
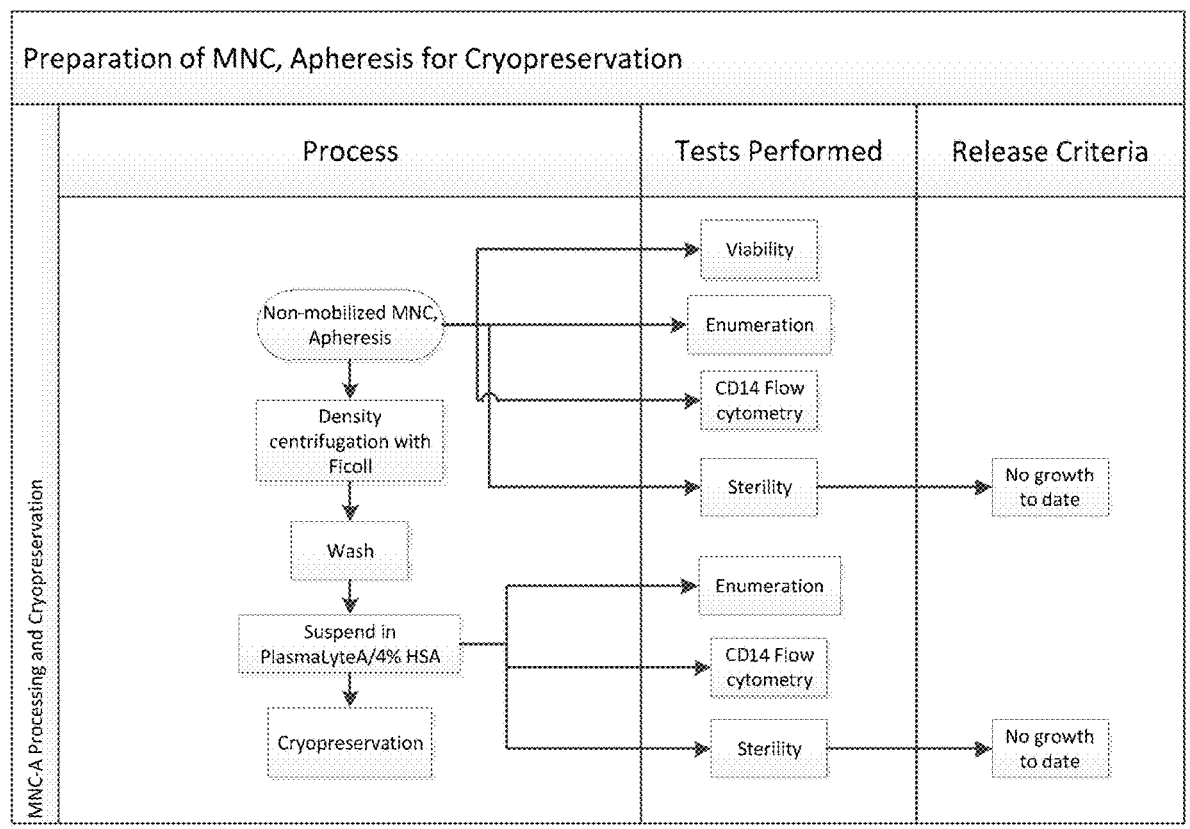

FIG. 17. Flow chart showing processes for preparation of autologous or allogeneic mononuclear cells and apheresis for cryopreservation.

Figure 18:
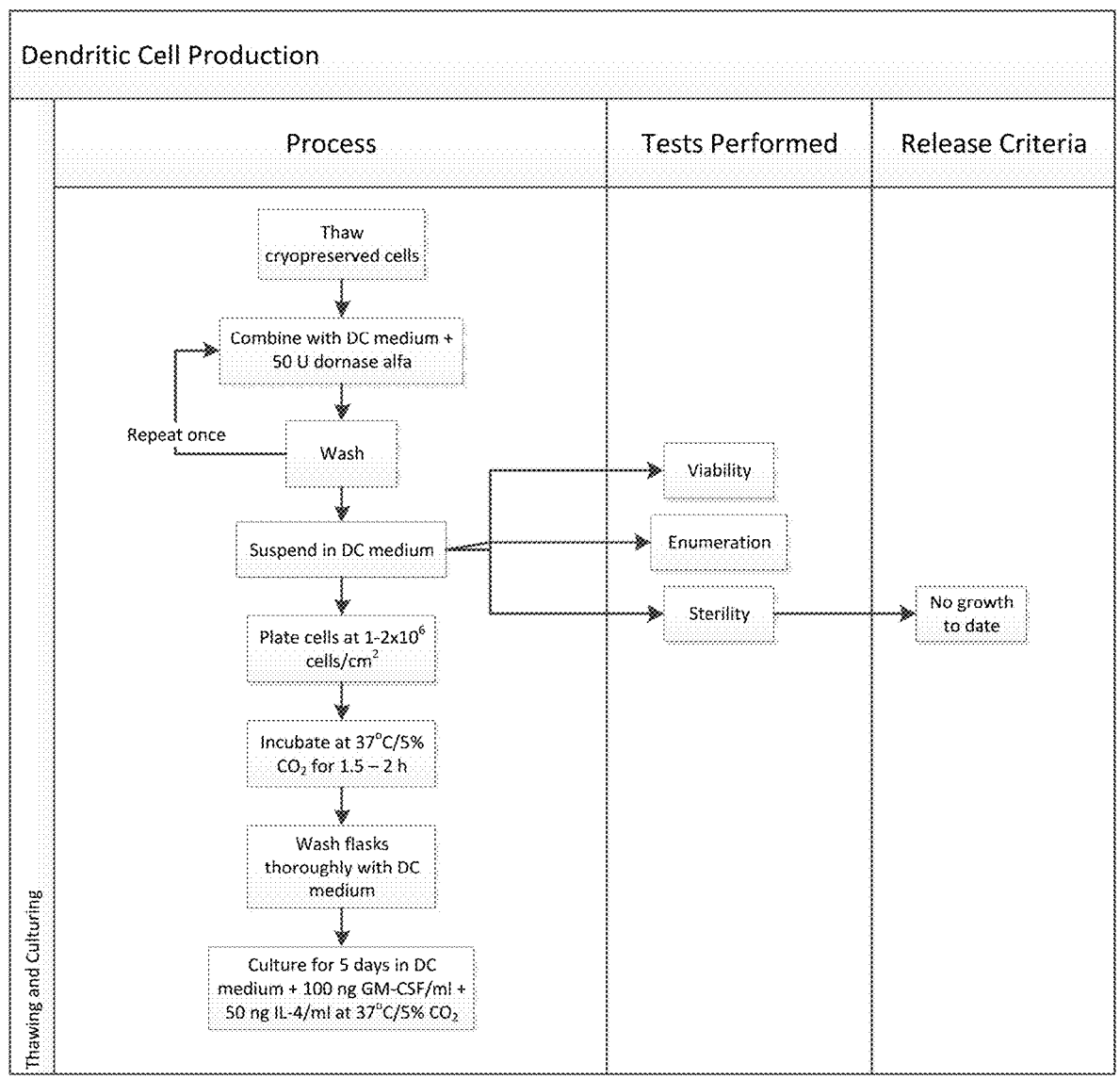

FIG. 18. Flow chart showing processes for thawing and culturing during dendritic cell production.

Figure 19:
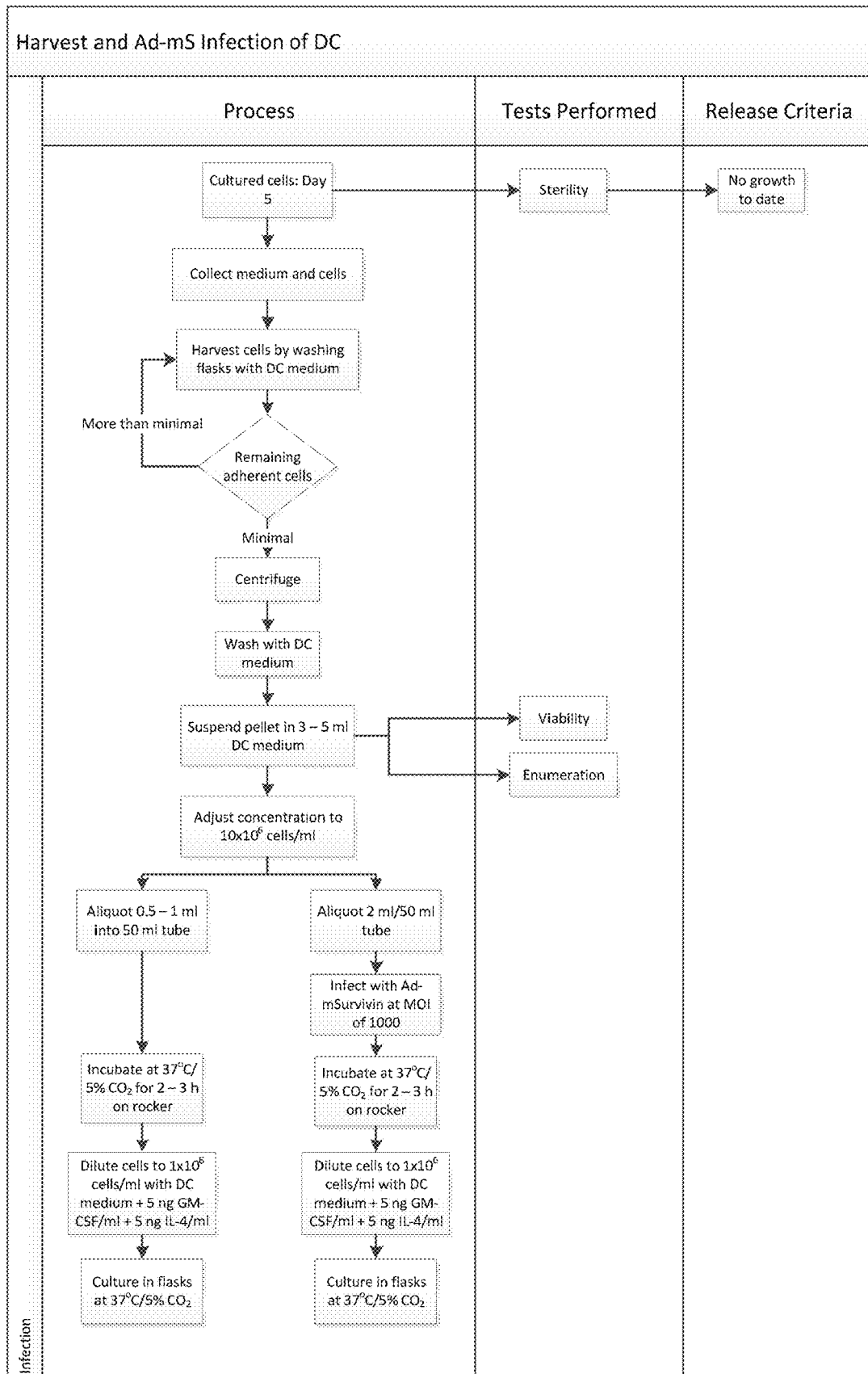

FIG. 19. Flow chart showing processes for harvesting and infection of dendritic cells with Ad-mSurvivin.

Figure 20:
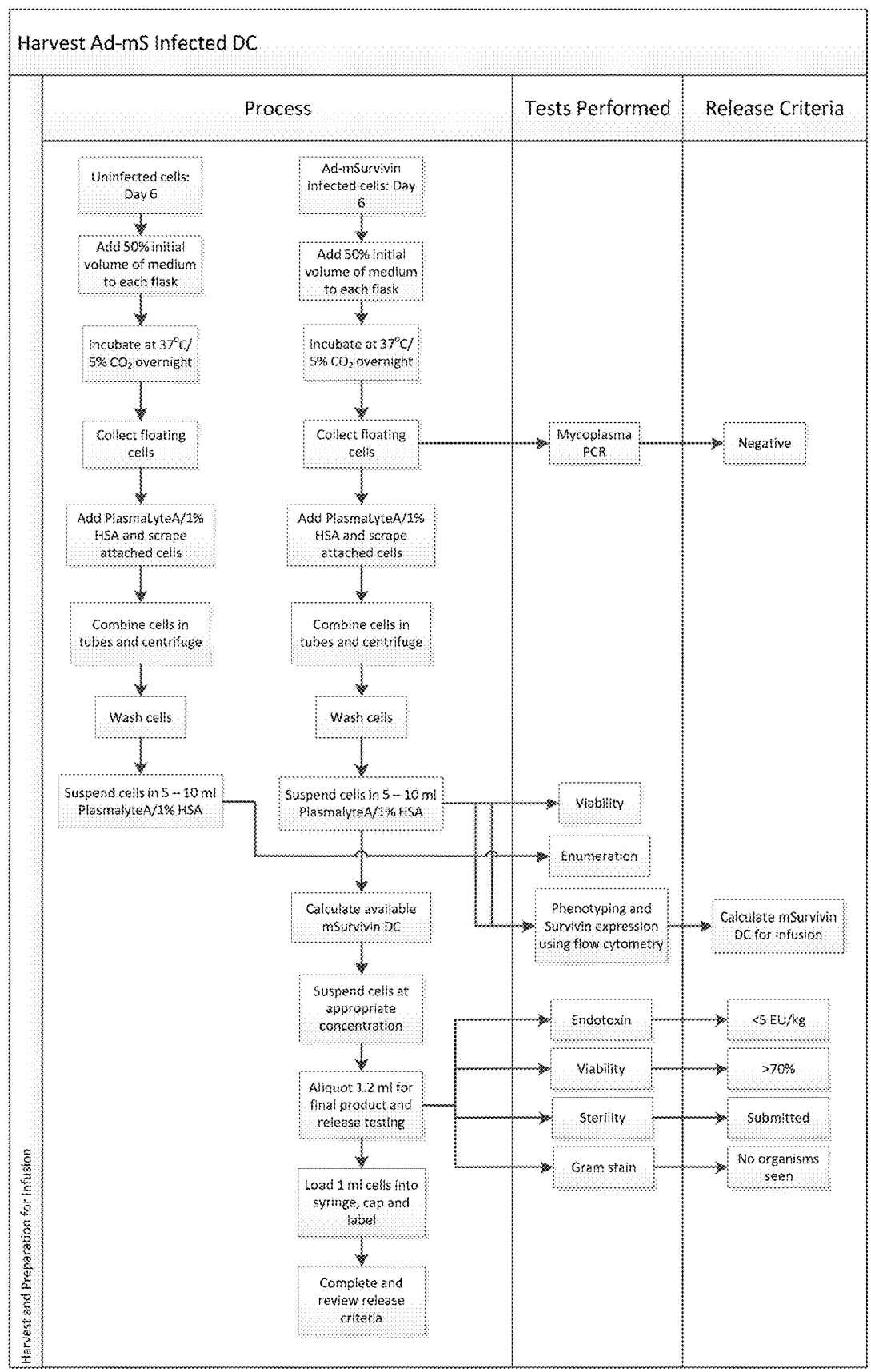

FIG. 20. Flow chart showing processes for harvesting of Ad-mSurvivin infected dendritic cells and preparation for infusion.

Figure 21:
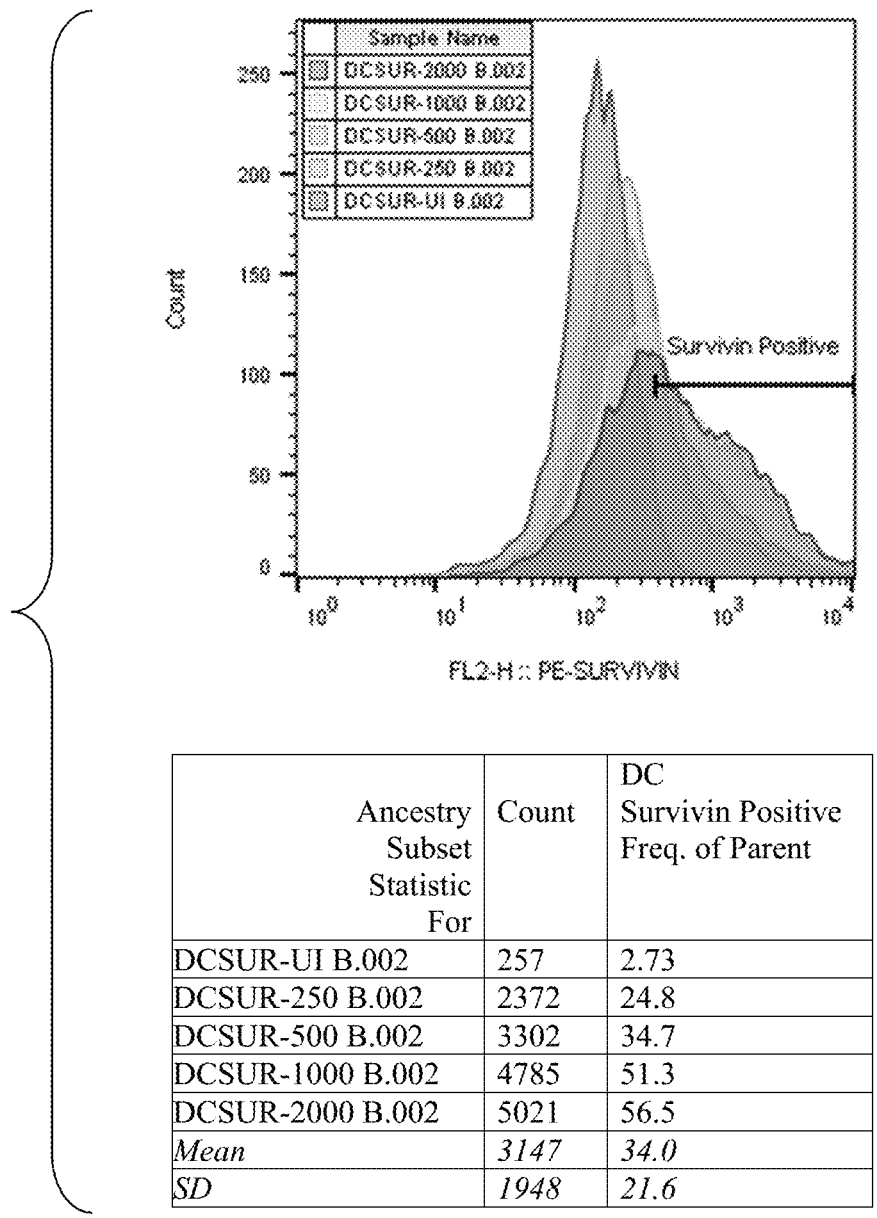

FIG. 21. Optimization of dendritic cell infection. FIG. 21 shows a range of multiplicities of infection (MOI; IFU/cell), centered on an MOI of 1,000.

BRIEF DESCRIPTION OF THE SEQUENCES

SEQ ID NO:1 is the full-length amino acid sequence of the human wild-type survivin with amino acid positions 34 and 84 in bold and underlined:

MGAPTLPPAWQPFLKDHRISTFKNWPFLEGCACTPERMAEAGFIHCPTEN

EPDLAQCFFCFKELEGWEPDDDPIEEHKKHSSGCAFLSVKKQFEELTLGE

FLKLDRERAKNKIAKETNNKKKEFEETAKKVRRAIEQLAAMD
(UniProtKB Reference No. 015392).

SEQ ID NO:2 is an embodiment of a full-length double mutant of human survivin with amino acid substitutions at positions 34 (T→Xaa) and 84 (C→Xaa) indicated in bold and underlined, wherein Xaa at position 34 is any amino acid other than threonine and Xaa at position 84 is any amino acid other than cysteine:

MGAPTLPPAWQPFLKDHRISTFKNWPFLEGCACXaaPERMAEAGFIHCPT

ENEPDLAQCFFCFKELEGWEPDDDPIEEHKKHSSGXaaAFLSVKKQFEEL

TLGEFLKLDRERAKNKIAKETNNKKKEFEETAKKVRRAIEQLAAMD.

SEQ ID NO:3 is an embodiment of a full-length double mutant of human survivin (T34A and C84A) with amino acid substitutions at positions 34 (T→A) and 84 (C→A) indicated in bold and underlined:

MGAPTLPPAWQPFLKDHRISTFKNWPFLEGCAC<u>A</u>PERMAEAGFIHCPTEN

EPDLAQCFFCFKELEGWEPDDDPIEEHKKHSSG<u>A</u>AFLSVKKQFEELTLGE

FLKLDRERAKNKIAKETNNKKKEFEETAKKVRRAIEQLAAMD.

SEQ ID NO:4 is the sequence of a forward primer for the C84A survivin mutant.

SEQ ID NO:5 is the sequence of a forward primer for the C84A survivin mutant.

SEQ ID NO:6 is the sequence of a forward primer for the T34A survivin mutant.

SEQ ID NO:7 is the sequence of a forward primer for the T34A survivin mutant.

SEQ ID NO:8 is an insert sequence.

DETAILED DESCRIPTION OF THE INVENTION

An antigen presenting cell displaying a variant survivin polypeptide was produced through transfection of dendritic cells (DCs) with a double mutant (T34A and C84A) full length survivin protein adenovirus construct and confirmed by Western blot. Co-culture of MM patient-derived DCs with CD4+CD25− peripheral T cells ex vivo resulted in a significant increase in both the frequency and absolute number of survivin-reactive CD4+ T cells, with a fold expansion range of 0-270× and median of 42×. Additionally, T cells expanded with DCs presenting this variant survivin protein were survivin specific by IFN-gamma ELISpot analysis when re-stimulated with survivin peptide pools, producing approximately three times as many spots as an irrelevant peptide control.

The invention concerns variant survivin polypeptides, nucleic acid molecules encoding them, and antigen presenting cells (APCs), and compositions containing the foregoing, useful as vaccines for the treatment of existing malignancies and preventing or delaying the onset of malignancies, and for raising or inducing immune responses (e.g., a survivin-reactive CD4+ T cell response) in human or non-human animal subjects. Accordingly, an aspect of the invention is directed to an APC comprising a variant survivin polypeptide or a nucleic acid sequence encoding the variant survivin polypeptide, wherein the variant survivin polypeptide comprises at least consecutive amino acids 16-87 (N-terminal zinc-binding baculovirus inhibitor of apoptosis protein repeat (BIR) domain) of the human wild-type survivin polypeptide (SEQ ID NO:1) modified to have an amino acid at position 34 which is other than threonine and an amino acid at position 84 which is other than cysteine, relative to the human wild-type survivin polypeptide, and wherein the variant survivin polypeptide:

(a) comprises a 142-amino acid sequence having at least 80% sequence identity to the human wild-type survivin polypeptide (SEQ ID NO:1), or (b) is a subsequence (fragment) of the human wild-type survivin polypeptide (SEQ ID NO:1).

Preferably, the APC presents portions of the variant survivin polypeptide on its surface.

In some embodiments, one or both of the amino acids at position 34 and at position 84 are nonpolar amino acids. In some embodiments, one or both of the amino acids at position 34 and at position 84 are alanine.

In some embodiments, the variant survivin polypeptide comprises the full-length human wild-type survivin polypeptide having an amino acid at position 34 which is other than threonine, and an amino acid at position 84 which is other than cysteine, as set forth as SEQ ID NO:2.

In some embodiments, the variant survivin polypeptide further includes at least consecutive amino acids 6-10, consecutive amino acids 89-97 (linker region), and consecutive amino acids 97-141 (coiled coil domain) of the human wild-type survivin polypeptide (SEQ ID NO:1).

As used herein, the term "antigen presenting cell" (APC) refers to professional antigen presenting cells (APC), which are selected from among dendritic cells, macrophages, and B cells. In some embodiments, the antigen presenting cell is a dendritic cell. In some embodiments, the APC is a mammalian cell. In some embodiments, the APC is a human cell.

Another aspect of the invention concerns a composition comprising a variant survivin polypeptide of the invention, a nucleic acid molecule encoding the polypeptide, or APCs of the invention (APCs comprising the variant survivin polypeptide or encoding nucleic acid sequence); and a pharmaceutically acceptable carrier. The composition may include further ingredients, such as an adjuvant or other anti-cancer agents, such as a chemotherapeutic or immunotherapeutic agent, or an antigen (e.g., a tumor-associated antigen).

When used in any of the methods or composition of the invention, an adjuvant may be of any class such as alum salts and other mineral adjuvants, bacterial products or bacteria-derived adjuvants, tensoactive agents (e.g., saponins), oil-in-water (o/w) and water-in-oil (w/o) emulsions, liposome adjuvants, cytokines (e.g., IL-2, GM-CSF, IL-12, and IFN-gamma), and alpha-galactosylceramide analogs. Nonlimiting examples of adjuvants include Montanide emulsions, QS21, Freund's complete or incomplete adjuvant, aluminum phosphate, aluminum hydroxide, *Bacillus* Calmette-Guerin (BCG), and alum. In one embodiment, the adjuvant is an agent that enhances the immune system's response against the variant survivin polypeptide. The adjuvant may be administered in the same composition as the variant survivin polypeptide, expression vector, or APC, or in a composition separate from the variant survivin polypeptide, expression vector, or APC.

Another aspect of the invention concerns a method for treating a malignancy, comprising administering to a subject in need of treatment an effective amount of antigen presenting cells of the invention. In some embodiments, the malignancy is myeloma or other hematologic malignancy.

The APCs may be autologous, homologous (allogeneic), or heterologous to the subject (recipient) to which the APCs are to be administered. The subject may be a human or non-human animal. In some embodiments, the subject is a human or non-human mammal.

Optionally, the method further comprises administering another treatment to the subject before, during, or after administration of the APCs. In some embodiments, one or more additional anti-cancer agents are administered to the subject before, during, or after administration of the APCs. In some embodiments, a chemotherapeutic drug, immunomodulator, adjuvant, anemia drug (e.g., erythropoietin), radiation therapy, stem cell transplant, or a combination of two or more of the foregoing is administered to the subject before, during, or after administration of the APCs.

In some embodiments, the method does not include administration of an anti-CD25 antibody. In some embodiments, the method does not include administration of a humanized IgG1 monoclonal antibody that binds specifically to the alpha subunit (p55 alpha, CD25, or Tac subunit) of the human high-affinity interleukin-2 (IL-2) receptor.

The APCs (and compositions comprising the APCs) may be administered to the subject by any route, locally or systemically. In some embodiments, the APCs are administered by intradermal injection, such as at an anatomical site that drains to the axillary and/or inguinal lymph node basins of the subject. The APCs may be administered one or more times at regular or irregular intervals. In some embodiments, the APCs are administered multiple times over a period of days.

In some embodiments, the method further comprises administering an adjuvant before, during, or after administration of the APCs to the subject. If administered to the subject simultaneously with the APCs, the adjuvant may be in the same composition as the APCs, or in a separation composition.

The methods of the invention may further include administration of additional treatments before, during, or after administration of the APCs to the subject. Additional treatments may involve a treatment such as radiation or administration of an agent such a small molecule or biologic agent such as cells (autologous, allogeneic, or xenogeneic cell transplantation). Optionally, cells may be preserved (e.g., cryopreserved) prior to administration.

In some embodiments, the method further comprises conducting hematopoietic cell transplantation (hematopoietic stem cells or progenitor cells, e.g., from bone marrow, peripheral blood, or cord blood) on the subject. In some embodiments, the cell transplant is an autologous hematopoietic cell. In some embodiments, administration of the APCs straddles administration of the hematopoietic cell transplantation, i.e., administered before and after the hematopoietic cell transplantation. The method may further comprise conducting stem cell mobilization on the subject (e.g., with G-CSF) and collecting the hematopoietic cells from the subject prior to autologous hematopoietic cell transplantation. The method may further comprise, prior to said administering, collecting mononuclear cells from the subject for production of the antigen presenting cells to be administered to the subject. Optionally, cells may be cryopreserved prior to administration.

In some embodiments, the method further comprises administering a chemotherapeutic agent (e.g., melphalan) before, during, or after said administering of the APCs.

Another aspect of the invention concerns a method for producing antigen presenting cells producing a variant survivin polypeptide, comprising transfecting antigen presenting cells or their precursors with an expression construct comprising a nucleic acid sequence encoding a variant survivin polypeptide, wherein the variant survivin polypeptide comprises at least consecutive amino acids 16-87 (N-terminal zinc-binding baculovirus inhibitor of apoptosis protein repeat (BIR) domain) of the human wild-type survivin polypeptide (SEQ ID NO:1) modified to have an amino acid at position 34 which is other than threonine and an amino acid at position 84 which is other than cysteine, relative to the human wild-type survivin polypeptide, and wherein the variant survivin polypeptide:

(a) comprises a 142-amino acid sequence having at least 80% sequence identity to the human wild-type survivin polypeptide (SEQ ID NO:1), or (b) is a subsequence (fragment) of the human wild-type survivin polypeptide (SEQ ID NO:1).

In some embodiments, the expression construct is a viral vector, non-viral vector, or naked DNA. Examples of viral vectors that may be used include, but are not limited to, adenovirus, adeno-associated virus, poxvirus, lentivirus, alphavirus, herpesvirus, retrovirus, and vaccinia virus. Prior to transfection, mononuclear cells may be obtain from the subject (e.g., by apheresis) for production of myeloid dendritic cells. Optionally, mononuclear cells are cryopreserved. The method may include culturing the cells and collecting the resulting APCs prior to said transfecting. In some embodiments, the mononuclear cells are cultured in chemically defined, serum-free hematopoietic cell medium, GM-CSF, and IL-4; and collecting the resulting antigen presenting cells said transfecting.

Methods for making double mutant survivin constructs such as TC34,84AA have been described and can be used to produce APCs of the invention (see, for example, Zhang et al., "A survivin double point mutant has potent inhibitory effect on the growth of hepatocellular cancer cells", *Cancer Biology & Therapy*, April 2008, 7(4):547-554, and Cheung et al. "Survivin—biology and potential as a therapeutic target in oncology", OncoTargets and Therapy, 2013, 6:1453-1462, which are incorporated herein by reference in their entirety).

For example, the following materials and methods can be utilized:

1. Cloning of T34A/C84A survivin mutant:

Template; pcDNA3.0-WT-SURVIVIN (CLONING SITE; EcoRI site)

Mutation was established by QuikChange Site-Directed Mutagenesis kit (STRATAGENE); mutation primers are as follows;

```
Primer for C84A mutant:
                                      (SEQ ID NO: 4)
5-CATAAAAAGCATTCGTCCGGTGCCGCTTTCCTTTCTGTCAAGAAG-3

(SEQ ID NO: 5)
5-CTTCTTGACAGAAAGGAAAGCGGCACCGGACGAATGCTTTTTATG-3

Primer for T34A mutant:
                                      (SEQ ID NO: 6)
5-GAGGGCTGCGCCTGCGCCCCGGAGCGGATGGCC-3

(SEQ ID NO: 7)
5-GGCCATCCGCTCCGGGGCGCAGGCGCAGCCCTC-3
```

2. Establishment of Shuttle Vector:

Subcloning Hind III/XbaI fragment of pcDNA3.0 T34A/C84A survivin mutant into Hind III/XbaI site of pShuttle-CMV (7462 bp) for non GFP svv mutant or pAdTrack-CMV (9220 bp) for GFP svv mutant.

Insert sequence:

```
                                      (SEQ ID NO: 8)
AAGCTTGGTACCGAGCTCGGATCCACTAGTAACGGCCGCCAGTGTGCTGG

AATTCATCTGTCGACTGCTACCGCCAGATTTGAATCGCGGGACCCGTTGG

CAGAGGTGGCGGCGGCGGCATGGGTGCCCCGACGTTGCCCCCTGCCTGGC

AGCCCTTTCTCAAGGACCACCGCATCTCTACATTCAAGAACTGGCCCTTC

TTGGAGGGCTGCGCCTGCGCCCCGGAGCGGATGGCCGAGGCTGGCTTCAT

CCACTGCCCCACTGAGAACGAGCCAGACTTGGCCCAGTGTTTCTTCTGCT

TCAAGGAGCTGGAAGGCTGGGAGCCAGATGACGACCCCATAGAGGAACAT

AAAAAGCATTCGTCCGGTGCCGCTTTCCTTTCTGTCAAGAAGCAGTTTGA
```

-continued

```
AGAATTAACCCTTGGTGAATTTTTGAAACTGGACAGAGAAAGAGCCAAGA

ACAAAATTGCAAAGGAAACCAACAATAAGAAGAAAGAATTTGAGGAAACT

GCGAAGAAAGTGCGCCGTGCCATCGAGCAGCTGGCTGCCATGGATTGAGG

CCTCTGGCCGGAGCTGCCTGGTCCCAGAGTGGCTGCACCACTTCCAGGGT

TTATTCCCTGGTGCCACCAGCCTTCCTGTGGGCCCCTTAGCAATGTCTTA

GGAAAGGAGATCAACATTTTCAAATTAGATGTTTCAACTGTGCTCTTGTT

TTGTCTTGAAAGTGGCACCAGAGGTGCTTCTGCCTGTGCAGCGGGTGCTG

CTGGTAACAGTGGCTGCTTCTCTCTCTCTCTCTTTTTTGGGGGCTCAT

TTTTGCTGTTTTGATTCCCGGGGGATCCTAACATCGATAAAATAAAAGAT

TTTATTTAGTCTCCAGAAAAAGGGGGAATGAAAGACCCCACCTGTAGGT

TTGGCAAGCTAGCTTAAGTAACGCCATTTTGCAAGGCATGGAAAAATACA

TAACTGAGAATAGAGAAGTTCAGATCAAGGTCAGGAACAGATGGAACAGC

TGAATATGGGCCAAACAGGATATCTGTGGTAAGCAGTTCCTGCCCCGGCT

CAGGCCAAGAACAGATGGAACAGCTGAATATGGGCCAAACAGGATATCTG

TGGTAAGCAGTTCCTGCCCCGGCTCAGGCCAAGAACAGATGGTCCCAGAT

TGCGGTCCAGCCCTCAGCAGTTTCTAAGATAGATATCCGA
```

3. Homologous Recombination with Adenovirus Backbone Construct:

Homologous recombination was done between pShuttle-CMV—svv mutant or pAdTrack-CMV-svv mutant and pAdEasy-2(30767 bp) in BJ5183 cell (*E. coli*).

In order to better understand the survivin-specific immune response and identify vaccination strategies against myeloma and other cancers, the present inventors sought to characterize the survivin specific CD4+ T cell response using survivin-derived peptide pools.

In healthy donors and myeloma patients the present inventors have quantified the peripheral blood CD4+ T cell precursor frequency reactive against survivin (26). Survivin expression in myeloma patients' tumors correlates with decreased survivin-reactive CD4+ T cells. A full-length mutant survivin protein vaccine induces CD4+ responses independent of the survivin specific CD4+ precursor frequency. The inventors' results have several important implications.

Healthy donors have detectable T cells responsive against survivin which do not require in vitro expansion or cloning techniques to quantify. Prior reports employed methodology including multiple priming and stimulation steps to grow out clonal cells against survivin or vaccination to promote expansion in vivo. The presence of survivin-reactive T cells in healthy donors is not entirely surprising since survivin protein expression is limited in adult tissues.

Myeloma patients have decreased survivin specific CD4+ cells compared to healthy donors. The expression of tumor survivin inversely correlates to the magnitude of the survivin-specific T cell precursor frequency. Clearly, these T cells are unsuccessful at mediating spontaneous tumor rejection in these myeloma patients. It may be inferred that this is due to suppression or deletion of survivin-responsive T cells. Mechanisms for evasion of a survivin specific immune response are yet to be determined; however, candidates include the active suppression by regulatory T cells (Tregs) or myeloid derived suppressor cells (MDSC), tumor microenvironment cell adhesion-mediated immune resistance (27), or anergy of survivin-specific T cells due to insufficient antigen presentation (28).

Myeloma patients harbor tumor-specific Tregs which blunt T effector responses against myeloma (29), however Treg function may be impaired (30). Peripheral blood Tregs expand as myeloma progresses (31), although bone marrow Tregs are decreased compared to healthy controls (32). Considering these conflicting results, investigation into the precursor frequency of survivin specific Tregs is warranted. Myeloma patient MDSCs can both suppress T cell activity and promote tumor growth, while the myeloma cells themselves may promote MDSC generation (33). Granulocytic-MDSC increase with myeloma progression (34) and MDSC are increased in peripheral blood and bone marrow compared with healthy controls (33). An in vivo model of immunogenic myeloma suggested MDSC involvement at early stages of myeloma progression, since there was a CD8+ dependent reduction in tumor growth when MDSC were excluded from accumulating in the bone marrow (35). Additional efforts should be taken to quantify Treg and MDSC suppression of anti-myeloma T cells at the level of the microenvironment.

The interplay between myeloma cells and the bone marrow niche provides a tumor survival advantage via multiple cytokines, growth factors, and cell adhesion-mediated drug resistance (36). Multiple factors such as IL-6, IDO, IL-17, TGF-beta, or VEGF may also act within the tumor environment to alter immune responses (37-39). Recent evidence suggests that marrow stromal cells can induce inhibitory PD-L1 expression on myeloma cells (40) and protect myeloma cells from T cell cytotoxicity (27). Multiple mechanisms control peripheral tolerance, however direct induction of lymphocyte tolerance is termed anergy (41). Classical clonal anergy results from the insufficient delivery of cognate antigen or co-stimulatory signals to the T cell which directly results in dysfunction (42). In myeloma patients chronic antigen exposure (43), tumor up-regulation of PD-L1 (40), or T cell expression of PD-1 (44) and CTLA-4 (45) may all play a role in T cell dysfunction against survivin or other tumor associated antigens. Additional study of the relationship between marrow stroma, microenvironmental factors, T cell inhibitory signals and the spontaneous anti-tumor T cell response against myeloma is needed.

The use of a full-length mutant survivin vaccine allows expansion of survivin-specific CD4+ T cells regardless of the precursor frequency of the reactive CD4+ survivin cells. The survivin protein vaccine utilizes DCs transduced with an adenoviral construct containing a full-length mutant survivin (46). This vaccine elicits a survivin-specific immune response when used in vitro to stimulate cells from healthy donors and prostate cancer patients (47). In murine models, this vaccine generates a potent multi-epitope survivin-specific response and mediates both in vitro and in vivo antitumor immunity (25). A full-length protein vaccine is desirable for several reasons. It does not require HLA typing, thereby maximizing patient eligibility. Presentation of multiple antigens will maximize immunogenicity and CD4+ and CD8+ immune responses should be allowable. The inventors have demonstrated herein that the vaccine is able to expand CD4+ T cells reactive against survivin. Importantly, this is possible regardless of the precursor frequency of survivin-reactive T cells. This implies that the vaccine may induce survivin specific CD4+ immune responses even when the survivin specific CD4+ T cell precursor frequency is below the level of detection of the current assay. In summary, accurate methodology and understanding of the CD4+ T cell response against survivin is necessary for the development of cancer immunotherapies against survivin-expressing tumors. The inventors have, for the first time, quantified the circulating, CD4+ precursor frequency against survivin in healthy donors and myeloma patients. This response is lower in myeloma patients compared to healthy donors, and inversely correlates to tumor survivin expression. The use of a full-length mutant survivin vaccine expands survivin-reactive CD4+ cells independent of the survivin-reactive CD4+ precursor frequency.

Mammalian species which benefit from the disclosed compositions and methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient", "subject", and "individual" are used interchangeably and are intended to include such human and non-human species unless specified to be human or non-human.

Subjects in need of treatment using the methods of the present invention (e.g., having a malignancy) can be identified using standard techniques known to those in the medical or veterinary professions, as appropriate. A subject having a malignancy may be symptomatic or asymptomatic.

Patient responsiveness to treatment for a particular disorder can be based on a measurable parameter that is indicative of patient improvement after receiving a therapeutic treatment.

The terms "cancer" and "malignancy" are used herein interchangeably to refer to or describe the physiological condition in mammals that is typically characterized by unregulated cell growth. The cancer may be drug-resistant or drug-sensitive. The cancer may be primary or metastatic. The cancer may represent early, middle, or late stage disease, and be acute or chronic. Preferably, the cancer is one that expresses survivin at an abnormal or aberrantly high level relative to the corresponding normal cell or tissue type (see, for example, those cancers identified in Fukuda S and L M Pelus, *Mol Cancer Ther,* 2006, 5(5):1087-1098; and Pennati M et al., *Carcinogenesis,* 2007, 28(6):1133-1139, which are each incorporated herein by reference in their entirety). Examples of cancers that over-express survivin include but are not limited to esophageal, lung, central nervous system, breast, colorectal, bladder, gastric, prostate, pancreatic, laryngeal, uterine, hepatocellular, renal, melanoma, soft tissue sarcoma, and hematologic malignancies such as lymphoma, acute leukemia, or myelodysplastic syndrome (MDS).

Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer. In some embodiments, the cancer is melanoma, MDS, ovarian cancer, breast cancer, or multiple myeloma.

In some embodiments, the cancer is liver cancer. In other embodiments, the cancer is a cancer other than liver cancer.

Other non-limiting examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas. Examples of cancer types that may be treated with the compositions and methods of the invention are listed in Table 1.

TABLE 1

| Examples of Cancer Types | |
| --- | --- |
| Acute Lymphoblastic Leukemia, Adult | Hairy Cell Leukemia |
| Acute Lymphoblastic Leukemia, Childhood | Head and Neck Cancer |
| | Hepatocellular (Liver) Cancer, Adult (Primary) |
| Acute Myeloid Leukemia, Adult | Hepatocellular (Liver) Cancer, Childhood (Primary) |
| Acute Myeloid Leukemia, Childhood | |
| Adrenocortical Carcinoma | Hodgkin's Lymphoma, Adult |
| Adrenocortical Carcinoma, Childhood | Hodgkin's Lymphoma, Childhood |
| AIDS-Related Cancers | Hodgkin's Lymphoma During Pregnancy |
| AIDS-Related Lymphoma | Hypopharyngeal Cancer |
| Anal Cancer | Hypothalamic and Visual Pathway Glioma, Childhood |
| Astrocytoma, Childhood Cerebellar | |
| Astrocytoma, Childhood Cerebral | Intraocular Melanoma |
| Basal Cell Carcinoma | Islet Cell Carcinoma (Endocrine Pancreas) |
| Bile Duct Cancer, Extrahepatic | Kaposi's Sarcoma |
| Bladder Cancer | Kidney (Renal Cell) Cancer |
| Bladder Cancer, Childhood | Kidney Cancer, Childhood |
| Bone Cancer, Osteosarcoma/Malignant Fibrous Histiocytoma | Laryngeal Cancer |
| | Laryngeal Cancer, Childhood |
| Brain Stem Glioma, Childhood | Leukemia, Acute Lymphoblastic, Adult |
| Brain Tumor, Adult | Leukemia, Acute Lymphoblastic, Childhood |
| Brain Tumor, Brain Stem Glioma, Childhood | Leukemia, Acute Myeloid, Adult |
| | Leukemia, Acute Myeloid, Childhood |
| Brain Tumor, Cerebellar Astrocytoma, Childhood | Leukemia, Chronic Lymphocytic |
| | Leukemia, Chronic Myelogenous |
| Brain Tumor, Cerebral | Leukemia, Hairy Cell |

TABLE 1-continued

Examples of Cancer Types

Astrocytoma/Malignant Glioma, Childhood
Brain Tumor, Ependymoma, Childhood
Brain Tumor, Medulloblastoma, Childhood
Brain Tumor, Supratentorial Primitive Neuroectodermal Tumors, Childhood
Brain Tumor, Visual Pathway and Hypothalamic Glioma, Childhood
Brain Tumor, Childhood
Breast Cancer
Breast Cancer, Childhood
Breast Cancer, Male
Bronchial Adenomas/Carcinoids, Childhood
Burkitt's Lymphoma
Carcinoid Tumor, Childhood
Carcinoid Tumor, Gastrointestinal
Carcinoma of Unknown Primary
Central Nervous System Lymphoma, Primary
Cerebellar Astrocytoma, Childhood
Cerebral Astrocytoma/Malignant Glioma, Childhood
Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see Mycosis Fungoides and Sézary Syndrome
Endometrial Cancer
Ependymoma, Childhood
Esophageal Cancer
Esophageal Cancer, Childhood
Ewing's Family of Tumors
Extracranial Germ Cell Tumor, Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid Tumor
Germ Cell Tumor, Extracranial, Childhood
Germ Cell Tumor, Extragonadal
Germ Cell Tumor, Ovarian
Gestational Trophoblastic Tumor
Glioma, Adult
Glioma, Childhood Brain Stem
Glioma, Childhood Cerebral Astrocytoma
Glioma, Childhood Visual Pathway and Hypothalamic
Skin Cancer (Melanoma)
Skin Carcinoma, Merkel Cell
Small Cell Lung Cancer
Small Intestine Cancer
Soft Tissue Sarcoma, Adult
Soft Tissue Sarcoma, Childhood
Squamous Cell Carcinoma, see Skin Cancer (non-Melanoma)
Squamous Neck Cancer with Occult Primary, Metastatic
Stomach (Gastric) Cancer
Stomach (Gastric) Cancer, Childhood
Supratentorial Primitive Neuroectodermal Tumors, Childhood
T-Cell Lymphoma, Cutaneous, see Mycosis Fungoides and Sézary Syndrome
Testicular Cancer
Lip and Oral Cavity Cancer
Liver Cancer, Adult (Primary)
Liver Cancer, Childhood (Primary)
Lung Cancer, Non-Small Cell
Lung Cancer, Small Cell
Lymphoma, AIDS-Related
Lymphoma, Burkitt's
Lymphoma, Cutaneous T-Cell, see Mycosis Fungoides and Sézary Syndrome
Lymphoma, Hodgkin's, Adult
Lymphoma, Hodgkin's, Childhood
Lymphoma, Hodgkin's During Pregnancy
Lymphoma, Non-Hodgkin's, Adult
Lymphoma, Non-Hodgkin's, Childhood
Lymphoma, Non-Hodgkin's During Pregnancy
Lymphoma, Primary Central Nervous System
Macroglobulinemia, Waldenström's
Malignant Fibrous Histiocytoma of Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with Occult Primary
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer
Nasopharyngeal Cancer, Childhood
Neuroblastoma
Non-Hodgkin's Lymphoma, Adult
Non-Hodgkin's Lymphoma, Childhood
Non-Hodgkin's Lymphoma During Pregnancy
Non-Small Cell Lung Cancer
Oral Cancer, Childhood
Oral Cavity Cancer, Lip and
Oropharyngeal Cancer
Osteosarcoma/Malignant Fibrous Histiocytoma of Bone
Ovarian Cancer, Childhood
Ovarian Epithelial Cancer
Ovarian Germ Cell Tumor
Ovarian Low Malignant Potential Tumor
Pancreatic Cancer
Pancreatic Cancer, Childhood
Pancreatic Cancer, Islet Cell
Paranasal Sinus and Nasal Cavity Cancer
Parathyroid Cancer
Penile Cancer
Pheochromocytoma
Pineoblastoma and Supratentorial Primitive Neuroectodermal Tumors, Childhood
Pituitary Tumor
Plasma Cell Neoplasm/Multiple Myeloma
Pleuropulmonary Blastoma
Pregnancy and Breast Cancer
Pregnancy and Hodgkin's Lymphoma
Pregnancy and Non-Hodgkin's Lymphoma
Primary Central Nervous System Lymphoma
Prostate Cancer
Rectal Cancer
Renal Cell (Kidney) Cancer
Renal Cell (Kidney) Cancer, Childhood
Renal Pelvis and Ureter, Transitional Cell Cancer
Retinoblastoma

TABLE 1-continued

Examples of Cancer Types

| | |
|---|---|
| Thymoma, Childhood | Rhabdomyosarcoma, Childhood |
| Thymoma and Thymic Carcinoma | Salivary Gland Cancer |
| Thyroid Cancer | Salivary Gland Cancer, Childhood |
| Thyroid Cancer, Childhood | Sarcoma, Ewing's Family of Tumors |
| Transitional Cell Cancer of the Renal Pelvis and Ureter | Sarcoma, Kaposi's |
| | Sarcoma, Soft Tissue, Adult |
| Trophoblastic Tumor, Gestational | Sarcoma, Soft Tissue, Childhood |
| Unknown Primary Site, Carcinoma of, Adult | Sarcoma, Uterine |
| | Sezary Syndrome |
| Unknown Primary Site, Cancer of, Childhood | Skin Cancer (non-Melanoma) |
| | Skin Cancer, Childhood |
| Unusual Cancers of Childhood | |
| Ureter and Renal Pelvis, Transitional Cell Cancer | |
| Urethral Cancer | |
| Uterine Cancer, Endometrial | |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

In some embodiments, the malignancy is a myeloma. The myeloma may be stage I, stage II, or stage III based on Durie-Salmon staging, and/or Group A or Group B based on kidney function. For example, a subject could be classified as Stage IIB. Another staging system that may be utilized is the International Staging system (ISS), which is based on the albumin level (more or less than 3.5 mg/dL) and B2-microglobulin level (<3.5; 3.5-5 or >5 mg/L). The myeloma may be of any ISS stage, and/or of various types such as monoclonal gammopathy of undetermined significance (MGUS), asymptomatic (smoldering/indolent), or symptomatic (active) myeloma.

In some embodiments, the malignancy is one that overexpresses survivin.

As used herein, the term "tumor" refers to all neoplastic cell growth and proliferation, whether malignant or benign, and all pre-cancerous and cancerous cells and tissues. For example, a particular cancer may be characterized by a solid mass tumor or non-solid tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography) or magnetic resonance imaging (MRI), or by needle aspirations. The use of these latter techniques is more common in early detection. Molecular and phenotypic analysis of cancer cells within a tissue can usually be used to confirm if the cancer is endogenous to the tissue or if the lesion is due to metastasis from another site. Some tumors are unresectable (cannot be surgically removed due to, for example the number of metastatic foci or because it is in a surgical danger zone). The treatment and prognostic methods of the invention can be utilized for early, middle, or late stage disease, and acute or chronic disease.

Compositions and Treatments

Various methods may be used to deliver the variant survivin polypeptide, or deliver a nucleic acid sequence encoding the variant polypeptide, in order to produce an antigen presenting cell (APC), such as a dendritic cell, of the invention. Preferably, the APC presents portions of the variant survivin polypeptide on its self surface.

Examples of methods that may be utilized to deliver the variant survivin polypeptide or encoding nucleic acid molecules to produce the APCs of the invention include, but are not limited to, viral vectors, such as retro virus, adenovirus, adeno-associated virus, lentivirus, vesicular stomatitis virus, or herpes simplex virus; nanoparticles; naked or packed protein; peptide pools of variant survivin polypeptides; gene editing systems such as TALEN (Transcription Activator-Like Effector Nucleases) or CRISPR (Clustered Regulatory Interspaced Short Palindromic Repeats)/Cas9 systems (see, for example, Nemudryi A A et al., *Acta Nature*, 2014 July-September, 6(3):19-40, which is incorporated herein by reference); DNA (naked or packaged); mRNA (naked or packaged); electroporation; sonoporation; gene gun, gold or other metal particles; magnetofication; hydrodynamic delivery; DNA plasmid; siiRNA, oligonucleotides, lipoplexes; lipoproteins, homing nucleases; polymersomes; polyplexes; transposon (e.g., sleeping beauty transposon, see for example, Ivies Z et al., *Hum Gene Ther* 2011, 22(9):1043-1051, which is incorporated herein by reference in its entirety); dendrimer; macromolecule; inorganic nanoparticle; quantum dot, cell penetrating peptide (also known as a peptide transduction domain) such as HIV TAT protein, Antennapedia transduction domain, transportan, or polyarginine (see, for example, Copolovici D M et al., *ACS Nano*, 2014, 8(3):1972-1994; Wagstaff K M et al., *Curr Meth Chem*, 2006, 13(12):1371-87, and Trabulo S et al., *Pharmaceuticals*, 2010, 3:961-993, which are incorporated herein by reference in their entirety); virosome; hybridizing virus; bacteriophage; or gene targeting.

Methods for making dendritic cell vaccines with other tumor antigens and their use for cancer immunotherapy are known and may be used with the variant survivin molecules described herein (see, for example, Palucka K et al., *Nature Reviews Cancer*, 2012, 12:265-277, which is incorporated herein by reference in its entirety).

Viral or non-viral gene delivery methods may be used to transfect cells such as APCs with nucleic acids encoding the variant survivin polypeptide.

Examples of viral vectors that may be used to deliver nucleic acids include but are not limited to adenovirus (AV), adeno-associated virus (AAV), poxvirus, lentivrus, alphavirus, herpesvirus, retrovirus, and vaccinia virus.

Non-viral methods for gene delivery include, but are not limited to, naked DNA injection, inorganic particles, synthetic or natural biodegradable particles, as well as physical methods such as needle injection, ballistic DNA injection, electroporation, sonoporation, photoporation, magnetofectoin, and hydroporation. Examples of inorganic particles include calcium phosphate, silica, gold, and magnetic particles. Examples of synthetic or natural biodegradable particles include polymeric-based non-viral vectors such as poly(lactic-co-glycolic acid (PLGA), poly lactic acid (PLA), poly(ethylene imine4) (PEI), chitosan, dendrimers, and polymethacrylates; cationic lipid-based non-viral vectors such as cationic liposomes, cationic emulsions, and solid lipid nanoparticles; and peptide-based non-viral vectors such as poly-L-lysine.

Optionally, APCs such as dendritic cells comprising a variant survivin polypeptide (presenting portions of the variant survivin polypeptide) can be co-administered, simultaneously or consecutively, with one or more other agents to a subject. Anti-cancer agents that may be administered include but are not limited to those listed Table 2.

Co-administration can be carried out simultaneously (in the same or separate formulations) or consecutively with the additional agent administered before and/or after one or more compounds disclosed herein.

Thus, the APCs, whether administered separately, or as a pharmaceutical composition, can include various other components. Examples of acceptable components or adjuncts which can be employed in relevant circumstances include antioxidants, free radical scavenging agents, peptides, growth factors, antibiotics, bacteriostatic agents, immunosuppressives, anticoagulants, buffering agents, anti-inflammatory agents, anti-angiogenics, anti-pyretics, time-release binders, anesthetics, steroids, and corticosteroids. Such components can provide additional therapeutic benefit, act to affect the therapeutic action of the APCs and variant survivin polypeptide, or act towards preventing any potential side effects which may be posed as a result of administration of the compounds.

Additional agents that can be co-administered to target cells in vitro or in vivo, such as in a subject, in the same or as a separate formulation, include those that modify a given biological response, such as immunomodulators. The additional agents may be, for example, small molecules, polypeptides (proteins, peptides, or antibodies or antibody fragments), or nucleic acids (encoding polypeptides or inhibitory nucleic acids such as antisense oligonucleotides or interfering RNA). For example, proteins such as tumor necrosis factor (TNF), interferon (such as alpha-interferon and beta-interferon), nerve growth factor (NGF), platelet derived growth factor (PDGF), and tissue plasminogen activator can be administered. Biological response modifiers, such as lymphokines, interleukins (such as interleukin-1 (IL-1), interleukin-2 (IL-2), and interleukin-6 (IL-6)), granulocyte macrophage colony stimulating factor (GM-CSF), granulocyte colony stimulating factor (G-CSF), or other growth factors can be administered. In one embodiment, the methods and compositions of the invention incorporate one or more anti-cancer agents, such as cytotoxic agents, chemotherapeutic agents, anti-signaling agents, and anti-angiogenic agents.

In some embodiments, the compositions of the invention include at least one additional anti-cancer agent (e.g., a chemotherapeutic agent). In some embodiments of the methods of the invention, at least one additional anti-cancer agent is administered with the compound of the invention. In some embodiments, the anti-cancer agent is selected from among suberoylanilide hydroxamic acid (SAHA) or other histone deacetylase inhibitor, arsenic trioxide, doxorubicin or other anthracycline DNA intercalating agent, and etoposide or other topoisomerase II inhibitor.

In some embodiments, the compositions can include, and the methods can include administration of, one or more proteasome inhibitors (e.g., bortezomib), inhibitors of autophagy (e.g., chloroquine), alkylating agents (e.g., melphalan, cyclophosphamide), MEK inhibitors (e.g., PD98509), FAK/PYK2 inhibitors (e.g., PF562271), or EGFR inhibitors (e.g., erlotinib, gefitinib, cetuximab, panitumumab, zalutumumab, nimotuzumab, matuzumab), or a combination of two or more of the foregoing.

Thus, immunotherapeutics, whether administered separately, or as a pharmaceutical composition, can include various other components as additives. Examples of acceptable components or adjuncts which can be employed in relevant circumstances include antioxidants, free radical scavenging agents, peptides, growth factors, antibiotics, bacteriostatic agents, immunosuppressives, anticoagulants, buffering agents, anti-inflammatory agents, anti-angiogenics, anti-pyretics, time-release binders, anesthetics, steroids, and corticosteroids. Such components can provide additional therapeutic benefit, act to affect the therapeutic action of the compounds of the invention, or act towards preventing any potential side effects which may be posed as a result of administration of the compounds. The immunotherapeutic agent can be conjugated to a therapeutic agent or other agent, as well.

As used herein, the term "immunotherapy" refers to the treatment of disease via the stimulation, induction, subversion, mimicry, enhancement, augmentation or any other modulation of a subject's immune system to elicit or amplify adaptive or innate immunity (actively or passively) against cancerous or otherwise harmful proteins, cells or tissues. Immunotherapies (i.e., immunotherapeutic agents) include cancer vaccines, immunomodulators, monoclonal antibodies (e.g., humanized monoclonal antibodies), immunostimulants, dendritic cells, and viral therapies, whether designed to treat existing cancers or prevent the development of cancers or for use in the adjuvant setting to reduce likelihood of recurrence of cancer. Examples of cancer vaccines include GVAX, Stimuvax, DCVax and other vaccines designed to elicit immune responses to tumor and other antigens including MUC1, NY-ESO-1, MAGE, p53 and others. Examples of immunomodulators include 1MT, Ipilimumab, Tremelimumab and/or any drug designed to de-repress or otherwise modulate cytotoxic or other T cell activity against tumor or other antigens, including, but not restricted to, treatments that modulate T-Reg cell control pathways via CTLA-4, CD80, CD86, MHC, B7-DC, B7-H1, B7-H2, B7-H3, B7-H4, CD28, other TCRs, PD-1, PDL-1, CD80, ICOS and their ligands, whether via blockade, agonist or antagonist. Examples of immunostimulants include corticosteroids and any other anti- or pro-inflammatory agent, steroidal or non-steroidal, including, but not restricted to, GM-CSF, interleukins (e.g., IL-2, IL-7, IL-12), cytokines such as the interferons, and others. Examples of dendritic cell (DC) therapies include modified dendritic cells and any other antigen presenting cell, autologous or xeno, whether modified by multiple antigens, whole cancer cells, single antigens, by mRNA, phage display or any other modification, including but not restricted to ex vivo-generated, antigen-loaded dendritic cells (DCs) to induce antigen-specific T-cell immunity, ex vivo gene-loaded DCs to induce humoral immunity, ex vivo-generated antigen-loaded DCs induce tumour-specific immunity, ex vivo-generated immature DCs to induce tolerance, including but not limited to Provenge and others. Examples of viral therapies include oncolytic viruses or virus-derived genetic or other material designed to elicit anti-tumor immunity and inhibitors of infectious viruses associated with tumor development, such as drugs in the Prophage series. Examples of monoclonal antibodies include Alemtuzumab, Bevacizumab, Cetuximab, Gemtuzumab ozogamicin, Rituximab, Trastuzumab, Radioimmunotherapy, Ibritumomab tiuxetan, Tositumomab/iodine tositumomab regimen. An immunotherapy may be a monotherapy or used in combination with one or more other therapies (one or more other immunotherapies or non-immunotherapies).

As used herein, the term "cytotoxic agent" refers to a substance that inhibits or prevents the function of cells and/or causes destruction of cells in vitro and/or in vivo. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, toxins such as small molecule toxins or enzymatically active toxins of bacterial, fungal, plant or animal origin, and antibodies, including fragments and/or variants thereof.

As used herein, the term "chemotherapeutic agent" is a chemical compound useful in the treatment of cancer, such as, for example, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON, GTx, Memphis, TN), and anti-androgens such as flutamide, nilutamide, bicalutamide, leuprolide, and goserelin, etc. Examples of anti-cancer agents, including chemotherapeutic agents, that may be used in conjunction with the compounds of the invention are listed in Table 2. In a preferred embodiment, the chemotherapeutic agent is one or more anthracyclines. Anthracyclines are a family of chemotherapy drugs that are also antibiotics. The anthracyclines act to prevent cell division by disrupting the structure of the DNA and terminate its function by: (1) intercalating into the base pairs in the DNA minor grooves; and (2) causing free radical damage of the ribose in the DNA. The anthracyclines are frequently used in leukemia therapy. Examples of anthracyclines include daunorubicin (CERUBIDINE), doxorubicin (ADRIAMYCIN, RUBEX), epirubicin (ELLENCE, PHARMORUBICIN), and idarubicin (IDAMYCIN).

TABLE 2

Examples of Anti-Cancer Agents

| | |
|---|---|
| 13-cis-Retinoic Acid | Mylocel |
| 2-Amino-6-Mercaptopurine | Letrozole |
| | Neosar |
| 2-CdA | Neulasta |
| 2-Chlorodeoxyadenosine | Neumega |
| 5-fluorouracil | Neupogen |
| 5-FU | Nilandron |
| 6-TG | Nilutamide |
| 6-Thioguanine | Nitrogen Mustard |
| 6-Mercaptopurine | Novaldex |
| 6-MP | Novantrone |
| Accutane | Octreotide |

TABLE 2-continued

Examples of Anti-Cancer Agents

| | |
|---|---|
| Actinomycin-D | Octreotide acetate |
| Adriamycin | Oncospar |
| Adrucil | Oncovin |
| Agrylin | Ontak |
| Ala-Cort | Onxal |
| Aldesleukin | Oprevelkin |
| Alemtuzumab | Orapred |
| Alitretinoin | Orasone |
| Alkaban-AQ | Oxaliplatin |
| Alkeran | Paclitaxel |
| All-transretinoic acid | Pamidronate |
| Alpha interferon | Panretin |
| Altretamine | Paraplatin |
| Amethopterin | Pediapred |
| Amifostine | PEG Interferon |
| Aminoglutethimide | Pegaspargase |
| Anagrelide | Pegfilgrastim |
| Anandron | PEG-INTRON |
| Anastrozole | PEG-L-asparaginase |
| Arabinosylcytosine | Phenylalanine Mustard |
| Ara-C | Platinol |
| Aranesp | Platinol-AQ |
| Aredia | Prednisolone |
| Arimidex | Prednisone |
| Aromasin | Prelone |
| Arsenic trioxide | Procarbazine |
| Asparaginase | PROCRIT |
| ATRA | Proleukin |
| Avastin | Prolifeprospan 20 with Carmustine implant |
| BCG | Purinethol |
| BCNU | Raloxifene |
| Bevacizumab | Rheumatrex |
| Bexarotene | Rituxan |
| Bicalutamide | Rituximab |
| BiCNU | Roveron-A (interferon alfa-2a) |
| Blenoxane | Rubex |
| Bleomycin | Rubidomycin hydrochloride |
| Bortezomib | Sandostatin |
| Busulfan | Sandostatin LAR |
| Busulfex | Sargramostim |
| C225 | Solu-Cortef |
| Calcium Leucovorin | Solu-Medrol |
| Campath | STI-571 |
| Camptosar | Streptozocin |
| Camptothecin-11 | Tamoxifen |
| Capecitabine | Targretin |
| Carac | Taxol |
| Carboplatin | Taxotere |
| Carmustine | Temodar |
| Carmustine wafer | Temozolomide |
| Casodex | Teniposide |
| CCNU | TESPA |
| CDDP | Thalidomide |
| CeeNU | Thalomid |
| Cerubidine | TheraCys |
| cetuximab | Thioguanine |
| Chlorambucil | Thioguanine Tabloid |
| Cisplatin | Thiophosphoamide |
| Citrovorum Factor | Thioplex |
| Cladribine | Thiotepa |
| Cortisone | TICE |
| Cosmegen | Toposar |
| CPT-11 | Topotecan |
| Cyclophosphamide | Toremifene |
| Cytadren | Trastuzumab |
| Cytarabine | Tretinoin |
| Cytarabine liposomal | Trexall |
| Cytosar-U | Trisenox |
| Cytoxan | TSPA |
| Dacarbazine | VCR |
| Dactinomycin | Velban |
| Darbepoetin alfa | Velcade |
| Daunomycin | VePesid |
| Daunorubicin | Vesanoid |
| Daunorubicin hydrochloride | Viadur |
| | Vinblastine |
| Daunorubicin liposomal | Vinblastine Sulfate |
| DaunoXome | Vincasar Pfs |

TABLE 2-continued

Examples of Anti-Cancer Agents

| | |
|---|---|
| Decadron | Vincristine |
| Delta-Cortef | Vinorelbine |
| Deltasone | Vinorelbine tartrate |
| Denileukin diftitox | VLB |
| DepoCyt | VP-16 |
| Dexamethasone | Vumon |
| Dexamethasone acetate | Xeloda |
| dexamethasone sodium phosphate | Zanosar |
| | Zevalin |
| Dexasone | Zinecard |
| Dexrazoxane | Zoladex |
| DHAD | Zoledronic acid |
| DIC | Zometa |
| Diodex | Gliadel wafer |
| Docetaxel | Glivec |
| Doxil | GM-CSF |
| Doxorubicin | Goserelin |
| Doxorubicin liposomal | granulocyte - colony stimulating factor |
| Droxia | Granulocyte macrophage colony stimulating factor |
| DTIC | |
| DTIC-Dome | Halotestin |
| Duralone | Herceptin |
| Efudex | Hexadrol |
| Eligard | Hexalen |
| Ellence | Hexamethylmelamine |
| Eloxatin | HMM |
| Elspar | Hycamtin |
| Emcyt | Hydrea |
| Epirubicin | Hydrocort Acetate |
| Epoetin alfa | Hydrocortisone |
| Erbitux | Hydrocortisone sodium phosphate |
| Erwinia L-asparaginase | Hydrocortisone sodium succinate |
| Estramustine | Hydrocortone phosphate |
| Ethyol | Hydroxyurea |
| Etopophos | Ibritumomab |
| Etoposide | Ibritumomab Tiuxetan |
| Etoposide phosphate | Idamycin |
| Eulexin | Idarubicin |
| Evista | Ifex |
| Exemestane | IFN-alpha |
| Fareston | Ifosfamide |
| Faslodex | IL - 2 |
| Femara | IL-11 |
| Filgrastim | Imatinib mesylate |
| Floxuridine | Imidazole Carboxamide |
| Fludara | Interferon alfa |
| Fludarabine | Interferon Alfa-2b (PEG conjugate) |
| Fluoroplex | Interleukin-2 |
| Fluorouracil | Interleukin-11 |
| Fluorouracil (cream) | Intron A (interferon alfa-2b) |
| Fluoxymesterone | Leucovorin |
| Flutamide | Leukeran |
| Folinic Acid | Leukine |
| FUDR | Leuprolide |
| Fulvestrant | Leurocristine |
| G-CSF | Leustatin |
| Gefitinib | Liposomal Ara-C |
| Gemcitabine | Liquid Pred |
| Gemtuzumab ozogamicin | Lomustine |
| Gemzar | L-PAM |
| Gleevec | L-Sarcolysin |
| Lupron | Meticorten |
| Lupron Depot | Mitomycin |
| Matulane | Mitomycin-C |
| Maxidex | Mitoxantrone |
| Mechlorethamine | M-Prednisol |
| Mechlorethamine Hydrochlorine | MTC |
| | MTX |
| Medralone | Mustargen |
| Medrol | Mustine |
| Megace | Mutamycin |
| Megestrol | Myleran |
| Megestrol Acetate | Iressa |
| Melphalan | Irinotecan |
| Mercaptopurine | Isotretinoin |
| Mesna | Kidrolase |
| Mesnex | Lanacort |
| Methotrexate | L-asparaginase |
| Methotrexate Sodium | LCR |
| Methylprednisolone | |

While APCs in the compositions and methods of the invention can be administered to subjects as isolated agents, it is preferred to administer these cells as part of a pharmaceutical composition. The subject invention thus further provides compositions comprising the described APCs in association with at least one pharmaceutically acceptable carrier. The pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

The compositions, variant survivin polypeptides, nucleic acid molecules encoding variant survivin polypeptides, expression constructs, and APCs administered in accordance with the methods of the invention can be formulated according to known methods for preparing pharmaceutically useful compositions. Formulations are described in a number of sources which are well known and readily available to those skilled in the art. For example, *Remington's Pharmaceutical Science* (Martin, E. W., 1995, Easton Pennsylvania, Mack Publishing Company, 19$^{th}$ ed.) describes formulations which can be used in connection with the subject invention. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts of compounds may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compositions of the invention, APCs, and others agents used in the methods of the invention may be locally administered at one or more anatomical sites, such as sites of unwanted cell growth (such as a tumor site, e.g., injected or topically applied to the tumor), optionally in combination with a pharmaceutically acceptable carrier such as an inert diluent. Compositions of the invention, APCs, and other agents used in the methods of the invention may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the agents may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the compositions and agents may be incorporated into sustained-release preparations and devices.

The active agents (e.g., APCs comprising variant survivin polypeptide) may also be administered intradermally, intravenously, or intraperitoneally by infusion or injection. In some embodiments, the APCs are administered by intradermal injection, such as at an anatomical site that drains to the axillary and/or inguinal lymph node basins of the subject. Solutions of the active agents can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the APCs of the invention which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating the compositions, APCs, and other agents in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compositions and agents may be applied in pure-form, i.e., when they are liquids. However, it will generally be desirable to administer them topically to the skin as compositions, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the peptide can be dissolved or dispersed at effective levels, optionally with the aid of non-toxic surfactants. Additives such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the peptides to the skin are disclosed in Jacquet et al. (U.S. Pat. No. 4,608,392), Geria (U.S. Pat. No. 4,992,478), Smith et al. (U.S. Pat. No. 4,559,157) and Woltzman (U.S. Pat. No. 4,820,508).

Useful dosages of the pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Accordingly, the present invention includes a pharmaceutical composition comprising APCs comprising variant survivin polypeptides or encoding nucleic acid sequences in combination, optionally, with a pharmaceutically acceptable carrier. Pharmaceutical compositions adapted for oral, topical or parenteral administration, comprising an amount of a compound of the invention constitute a preferred embodiment of the invention. The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition. Advantageously, in some embodiments, administration of the compounds of the invention does not induce weight loss or overt signs of toxicity in the subject.

Depending upon the disorder or disease condition to be treated (e.g., a malignancy such as myeloma), a suitable dose(s) may be that amount that will reduce proliferation or growth of the target cell(s), or induce cell death. In the context of cancer, a suitable dose(s) is that which will result in a concentration of the active agent in cancer tissue, such as a malignant tumor, which is known to achieve the desired response. The preferred dosage is the amount which results in maximum inhibition of cancer cell growth, without unmanageable side effects. Administration of APCs and other agents can be continuous or at distinct intervals, as can be determined by a person of ordinary skill in the art.

To provide for the administration of such dosages for the desired therapeutic treatment, in some embodiments, pharmaceutical compositions of the invention can comprise between about 0.1% and 45%, and especially, 1 and 15%, by weight of the total of one or more of the agents of the invention based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Dendritic Cell Preparation

Antigen presenting cells (APC) are important in eliciting an effective immune response. APC not only present antigens to T cells with antigen-specific receptors, but also provide the signals necessary for T cell activation. Such signals remain incompletely defined, but are known to involve a variety of cell surface molecules as well as cytokines or growth factors. The factors necessary for the activation of naive or unprimed T cells may be different from those required for the re-activation of previously primed memory T cells. Although monocytes and B cells have been shown to be competent APC, their antigen presenting capacities appear to be limited to the re-activation of previously sensitized T cells. Hence, they are not capable of directly activating functionally naive or unprimed T cell populations. On the other hand, dendritic cells are capable of both activating naive and previously primed T cells.

Dendritic cells have a distinctive morphology and a widespread tissue distribution, including blood. The cell surface of dendritic cells is unusual, with characteristic veil-like projections. Mature dendritic cells are generally identified as CD3−, CD11c+, CD19−, CD83+, CD86+ and HLA-DR+.

Dendritic cells process and present antigens, and stimulate responses from naive and unprimed T cells and memory T cells. In particular, dendritic cells have a high capacity for sensitizing MHC-restricted T cells and are very effective at presenting antigens to T cells, both self-antigens during T cell development and tolerance, and foreign antigens during an immune response. In addition to their role in antigen presentation, dendritic cells also directly communicate with non-lymph tissue and survey non-lymph tissue for an injury signal (e.g., ischemia, infection, or inflammation) or tumor growth. Once signaled, dendritic cells initiate an immune response by releasing cytokines that stimulate activity of lymphocytes and monocytes.

Due to their effectiveness at antigen presentation, dendritic cells may be used as an immunostimulatory agent, both in vivo and ex vivo. The use of isolated dendritic cells as immunostimulatory agents has been limited, however, due to the low frequency of dendritic cells in peripheral blood and the low purity of dendritic cells isolated by prior methods. In particular, the frequency of dendritic cells in human peripheral blood has been estimated at about 0.1% of the white cells. Similarly, there is limited accessibility of dendritic cells from other tissues, such as lymphoid organs. The low frequency of dendritic cells has increased interest in isolating cell population enriched in dendritic cell precursors, and culturing these precursors ex vivo or in vitro to obtain enriched populations of immature or mature dendritic cells. Because the characteristics of dendritic cell precursors remain incompletely defined, methods typically used for isolating dendritic cell precursors do not result in purified fractions of the desired precursors, but instead generally produce mixed populations of leukocytes enriched in dendritic cell precursors. Several cell types have been identified as having the potential to function as dendritic cell precursors. Blood-derived CD14+ monocytes, especially those that express on their surface the receptor for the growth factor granulocyte-monocyte colony stimulating factor (GM-CSF) are known dendritic cell precursors. Other blood-derived dendritic cell precursors can be isolated by first removing monocytes and other "non-dendritic cell precursors." (See, e.g., U.S. Pat. Nos. 5,994,126 and 5,851,756.). Other known dendritic cell precursors include bone marrow-derived cells that express the CD34 cell surface marker.

Cell populations enriched in dendritic cell precursors have been obtained by various methods and may be utilized with the invention, such as, for example, density gradient separation, fluorescence activated cell sorting, immunological cell separation techniques, e.g., panning, complement lysis, rosetting, magnetic cell separation techniques, nylon wool separation, and combinations of such methods. (See, e.g., O'Doherty et al., *J. Exp. Med.* 178:1067-76 (1993); *Young and Steinman, J. Exp. Med.* 171:1315-32 (1990); Freudenthal and Steinman, *Proc. Natl. Acad. Sci. USA* 87:7698-702 (1990); Macatonia et al., *Immunol.* 67:285-89 (1989); Markowicz and Engleman, *J. Clin. Invest.* 85:955-61 (1990) all incorporated herein by reference in their entirety). Methods for immuno-selecting dendritic cells include, for example, using antibodies to cell surface markers associated with dendritic cell precursors, such as anti-CD34 and/or anti-CD14 antibodies coupled to a substrate. (See, e.g., Bernhard et al., *Cancer Res.* 55:1099-104 (1995); Caux et. al., *Nature* 360:258-61 (1992)).

In one typical example method, leukocytes are isolated by a leukapheresis procedure. Additional methods are typically used for further purification to enrich for cell fractions thought to contain dendritic cells and/or dendritic cell precursors. Similarly, methods such as differential centrifugation (e.g., isolation of a buffy coat), panning with monoclonal antibodies specific for certain cell surface proteins (e.g., positive and negative selection), and filtration also produce a crude mixture of leukocytes containing dendritic cell precursors.

Another reported method for isolating proliferating dendritic cell precursors is to use a commercially treated plastic substrate (e.g., beads or magnetic beads) to selectively remove adherent monocytes and other "non-dendritic cell precursors." (See, e.g., U.S. Pat. Nos. 5,994,126 and 5,851,756). The adherent monocytes and non-dendritic cell precursors are discarded while the non-adherent cells are retained for ex vivo culture and maturation. In another method, apheresis cells were cultured in plastic culture bags to which plastic, i.e., polystyrene or styrene, microcarrier beads were added to increase the surface area of the bag. The cells were cultured for a sufficient period of time for cells to adhere to the beads and the non-adherent cells were washed from the bag. (Maffei, et al., *Transfusion* 40:1419-1420 (2000); WO 02/44338, incorporated herein by reference).

Subsequent to essentially all of the reported methods for the preparation of a cell population enriched for dendritic cell precursors, the cell populations are typically cultured ex vivo or in vitro for differentiation of the dendritic cell precursors or maintenance, and/or expansion of the dendritic cells. Briefly, ex vivo differentiation of monocytic dendritic cell precursors has involved culturing the mixed cell populations enriched for dendritic cell precursors in the presence of combinations of cellular growth factors, such as cytokines. For example, monocytic dendritic cell precursors require granulocyte/monocyte colony-stimulating factor (GM-CSF) in combination with at least one other cytokine selected from, for example, either Interleukin 4 (IL-4), Interleukin 15 (IL-15), Interleukin 13 (IL-13), interferon α (IFN-α), and the like, to differentiate the cells into an optimal state for antigen uptake, processing, and/or presentation. The numbers of dendritic cells from non-monocytic dendritic cell precursors, such as those obtained by removal of monocytes and other non-dendritic precursor cells (adsorption to a plastic surface) or selection for CD34+ cells, have also been expanded by culture in the presence of certain cytokines. Either GM-CSF alone or a combination of GM-CSF and IL-4 have been used in methods to produce dendritic cell populations from such proliferating dendritic cell precursors for therapeutic use.

The effectiveness of such ex vivo differentiation, maintenance and/or expansion has been limited, however, by the quality of the starting population enriched in dendritic cells and dendritic cell precursors. Under some culture conditions, populations of dendritic cells and dendritic cell precursors that are heavily contaminated with neutrophils, macrophages and lymphocytes, or combinations thereof, can be overtaken by the latter cells, resulting in a poor yield of dendritic cells. Culture of dendritic cells containing large numbers of neutrophils, macrophages and lymphocytes, or combinations thereof, are less suitable for use as immunostimulatory preparations.

Immature or mature dendritic cells, once obtained, may optionally be exposed to a target antigen(s) (such as the variant survivin polypeptide) and maturation agents to provide activated mature dendritic cells. In general, the antigen has been added to a cell population enriched for immature or mature dendritic cells under suitable culture conditions. In the case of immature dendritic cells, the cells are then allowed sufficient time to take up and process the antigen, and express antigenic peptides on the cell surface in association with either WIC class I or class II markers. Antigen can be presented to immature dendritic cells on the surface of cells, in purified form, in a semi-purified form, such as an isolated protein or fusion protein (e.g., a GM-CSF-antigen fusion protein), as a membrane lysate, as a liposome-protein complex, and other methods. In addition, as mature dendritic cells are not capable of taking up and processing antigen, antigenic peptides that bind to WIC class I or WIC class II molecules can be added to mature dendritic cells for presentation.

APCs such as dendritic cells can be administered to a subject to stimulate an immune response by bolus injection, by continuous infusion, sustained release from implants, or other suitable techniques known in the art. The APCs also can be co-administered with physiologically acceptable carriers, excipients, buffers and/or diluents. Further, APCs can be used to activate T cells, e.g., cytotoxic T cells, ex vivo using methods well known to the skilled artisan. The antigen specific cytotoxic T cells can then be administered to a patient to treat, for example, a growing tumor, or a bacterial or viral infection. These compositions can be used by themselves or as an adjuvant to other therapies, such as, for example, surgical resection, chemotherapy, radiation therapy, and combinations thereof, as well as other therapeutic modalities appropriate for the condition being treated.

Definitions

The terms "comprising", "consisting of" and "consisting essentially of" are defined according to their standard meaning. The terms may be substituted for one another throughout the instant application in order to attach the specific meaning associated with each term.

The terms "isolated" or "biologically pure" refer to material that is substantially or essentially free from components which normally accompany the material as it is found in its native state. Thus, compounds in accordance with the invention preferably do not contain materials normally associated with the peptides in their in situ environment.

As used in this specification, the singular forms "a", "an", and "the" include plural reference unless the context clearly dictates otherwise. Thus, for example, a reference to "a compound" includes more than one such compound. A reference to "a cell" includes more than one such cell, and so forth.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. Eds. (1991) IRL Press)), each of which are incorporated herein by reference in their entirety.

Some embodiments of the antigen presenting cells comprise a nucleic acid sequence encoding a variant survivin polypeptide, wherein the variant survivin polypeptide comprises at least consecutive amino acids 16-87 (N-terminal zinc-binding baculovirus inhibitor of apoptosis protein repeat (BIR) domain) of the human wild-type survivin polypeptide (SEQ ID NO:1) modified to have an amino acid at position 34 which is other than threonine and an amino acid at position 84 which is other than cysteine, relative to the human wild-type survivin polypeptide, and wherein the variant survivin polypeptide:

(a) comprises a 142-amino acid sequence having at least 80% sequence identity to the human wild-type survivin polypeptide (SEQ ID NO:1), or (b) is a subsequence (fragment) of the human wild-type survivin polypeptide (SEQ ID NO:1).

In some embodiments, the variant survivin polypeptide is a full length variant of the survivin polypeptide (e.g., comprising or consisting of SEQ ID NO:1), which allows for the presentation of multiple peptide epitopes and recognition by a more diverse immune repertoire across patient populations.

In some embodiments, the variant survivin polypeptide is a subsequence (fragment) of the human wild-type polypeptide (SEQ ID NO:1). According to the subject invention, a subsequence or "fragment" is a polypeptide that is one or more amino acids less than the full length sequence, such as the full length human sequence. Fragments contain one or more amino acid deletions relative to the full-length wild-type sequence. Deletions may occur at either end of the polypeptide, or within the polypeptide amino acid sequence. In some embodiments, the fragment is 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, or 141 consecutive amino acids. Polypeptides according to the instant invention may also contain non-natural amino acids, as will be described below.

A "variant" or "modified" survivin polypeptide (or polypeptide variant) is to be understood to designate polypeptides exhibiting, in relation to the natural polypeptide, certain modifications. These modifications can include a deletion, addition, or substitution of at least one amino acid, a truncation, an extension, a chimeric fusion, a mutation, or polypeptides exhibiting post-translational modifications. Among the homologous polypeptides, those whose amino acid sequences exhibit between at least (or at least about) 80.00% to 99.99% (inclusive) identity to the full length, native, or naturally occurring polypeptide are another aspect of the invention. The aforementioned range of percent identity is to be taken as including, and providing written description and support for, any fractional percentage, in intervals of 0.01%, between 80.00% and, up to, including 99.99% (e.g., 80, 81, 82, 83, 84, 85, 86, 87, 88, 89, 90, 91, 92, 93, 94, 95, 96, 97, 98, or 99%) sequence identity. These percentages are purely statistical and differences between two polypeptide sequences can be distributed randomly and over the entire sequence length.

Preferably, fragments (subsequences) and variants (sequences with less than 100% sequence identity) of the human double mutant survivin polypeptide (e.g., SEQ ID NO:2 and SEQ ID NO:3) retain the ability to induce the same or similar immune in a subject (e.g., a CD4+ immune response).

The L-form of an amino acid residue is represented by a capital single letter or a capital first letter of a three-letter symbol, and the D-form, for those amino acids having D-forms, is represented by a lower case single letter or a lower case three letter symbol. Glycine has no asymmetric carbon atom and is simply referred to as "Gly" or G. Symbols for the amino acids are as follows: (Single Letter Symbol; Three Letter Symbol Amino Acid) A; Ala; Alanine: C; Cys; Cysteine: D; Asp; Aspartic Acid: E; Glu; Glutamic Acid: F; Phe; Phenylalanine: G; Gly; Glycine: H; His; Histidine: I; Ile; Isoleucine: K; Lys; Lysine: L; Leu; Leucine: M; Met; Methionine: N; Asn; Asparagine: P; Pro; Proline: Q; Gln; Glutamine: R; Arg; Arginine: S; Ser; Serine: T; Thr; Threonine: V; Val; Valine: W; Trp; Tryptophan: Y; Tyr; Tyrosine.

Amino acid "chemical characteristics" are defined as: Aromatic (F, W, Y); Aliphatic-hydrophobic (L, I, V, M); Small polar (S, T, C); Large polar (Q, N); Acidic (D, E); Basic (R, H, K); Non-polar: Proline; Alanine; and Glycine.

In order to extend the life of the polypeptides according to the invention, it may be advantageous to use non-natural amino acids, for example in the D-form, or alternatively amino acid analogs, for example sulfur-containing forms of amino acids in the production of "variant polypeptides". Alternative means for increasing the life of polypeptides can also be used in the practice of the instant invention. For example, polypeptides of the invention, and fragments thereof, can be recombinantly modified to include elements that increase the plasma, or serum half-life of the polypeptides of the invention. These elements include, and are not limited to, antibody constant regions (see for example, U.S. Pat. No. 5,565,335, hereby incorporated by reference in its entirety, including all references cited therein), or other elements such as those disclosed in U.S. Pat. Nos. 6,319, 691, 6,277,375, or 5,643,570, each of which is incorporated by reference in its entirety, including all references cited within each respective patent. Alternatively, the polynucleotides and genes of the instant invention can be recombinantly fused to elements, well known to the skilled artisan, that are useful in the preparation of immunogenic constructs for the purposes of vaccine formulation.

The term "sequence identity" indicates a quantitative measure of the degree of homology between two amino acid sequences or between two nucleic acid sequences of equal length. If the two sequences to be compared are not of equal length, they must be aligned to give the best possible fit, allowing the insertion of gaps or, alternatively, truncation at the ends of the polypeptide sequences or nucleotide sequences.

With respect all embodiments of the invention relating to nucleotide sequences, the percentage of sequence identity between one or more sequences may also be based on alignments using any suitable software such as the clustalW software (http:/www.ebi.ac.uk/clustalW/index.html) with default settings. For nucleotide sequence alignments these settings are: Alignment=3Dfull, Gap Open 10.00, Gap Ext. 0.20, Gap separation Dist. 4, DNA weight matrix: identity (IUB). Alternatively, and as illustrated in the examples, nucleotide sequences may be analysed using any suitable software such as DNASIS Max and the comparison of the sequences may be done at http://www.paralicin.orci/. This service is based on the two comparison algorithms called Smith-Waterman (SW) and ParAlign. The first algorithm was published by Smith and Waterman (1981) and is a well established method that finds the optimal local alignment of two sequences. The other algorithm, ParAlign, is a heuristic method for sequence alignment; details on the method is published in Rognes (2001). Default settings for score matrix and Gap penalties as well as E-values were used.

When referring to complementary sequences, the following base pairing rules can be applied, G pairs to C and U, A pairs to T and U. "Nucleic acids sequence" and "polynucleotide sequence" are interchangeable terms in the context of the present invention.

The term "vector" refers to a DNA molecule used as a vehicle to transfer recombinant genetic material into a host cell. The four major types of vectors are plasmids, bacteriophages and other viruses, cosmids, and artificial chromosomes. The vector itself is generally a DNA or RNA sequence that consists of an insert (a heterologous nucleic acid sequence, transgene) and a larger sequence that serves as the "backbone" of the vector. The purpose of a vector which transfers genetic information to the host is typically to isolate, multiply, or express the insert in the target cell.

Vectors called expression vectors (expression constructs) are specifically adapted for the expression of the heterologous sequences in the target cell, and generally have a promoter sequence that drives expression of the heterologous sequences. Simpler vectors called transcription vectors are only capable of being transcribed but not translated: they can be replicated in a target cell but not expressed, unlike expression vectors. Transcription vectors are used to amplify the inserted heterologous sequences. The transcripts may subsequently be isolated and used as templates suitable for in vitro translation systems.

The choice of vector employed in embodiments of the present invention depends on the specific application of the vector encoding the polypeptides or polynucleotide of the invention. In some embodiments, the vector is a viral vector. In other embodiments, the vector is a non-viral vector.

The term "operatively linked" refers to the connection of elements being a part of a functional unit such as a gene or an open reading frame (e.g., encoding a variant survivin polypeptide described herein). Accordingly, by operatively linking a promoter to a nucleic acid sequence encoding a variant survivin polypeptide the two elements becomes part of the functional unit—a gene. The linking of the expression control sequence (promoter) to the nucleic acid sequence enables the transcription of the nucleic acid sequence directed by the promoter. Expression control sequences can be linked to a nucleic acid sequence encoding the variant survivin polypeptide with an expression construct. By operatively linking two heterologous nucleic acid sequences encoding a polypeptide the sequences becomes part of the functional unit—an open reading frame encoding a fusion protein comprising the amino acid sequences encoding by the heterologous nucleic acid sequences. By operatively linking two amino acids sequences, the sequences become part of the same functional unit—a polypeptide. Operatively linking two heterologous amino acid sequences generates a hybrid (fusion) polypeptide. Thus, fusions of a variant survivin polypeptide and another heterologous polypeptide can be produced, or multimers of variant survivin polypeptides can be produced. Optionally, fused polypeptides can be separated by cleavage sites intended to be targeted for cleavage, e.g., in vivo.

Materials and Methods for Examples 1-5

Sample Collection.

Healthy donor blood samples were provided as buffy coats from One Blood (St. Petersburg, Florida). Multiple myeloma patient blood and bone marrow aspirate was collected at Moffitt Cancer Center (Tampa, Florida) after informed consent to an IRB approved sample collection study (MCC 16617). Mononuclear cells were isolated from blood and bone marrow using density gradient centrifugation over Ficoll-Paque PLUS (GE Healthcare, Little Chalfont, UK).

Tumor Cell Isolation.

CD138+ plasma cells were selected from mononuclear bone marrow cells of multiple myeloma patients using magnetic column separation. Cells were incubated with CD138+ microbeads (Miltenyi, Germany) for 15 minutes, washed and eluted over an MS or LS column (Miltenyi). CD138+ cells retained in the column were collected and purity of >90% was verified by flow cytometry.

Dendritic Cell Generation and Peptide Pool Loading.

Dendritic cells (DCs) were generated by suspending 7-11×10$^6$ PBMCs/mL in serum-free XVIVO-15 media (Lonza, Allendale, NJ) followed by 3 hour culture in a 25 cm$^2$ cell culture flask (Corning, Corning, NY). Cells were then washed twice in PBS to remove non-adherent cells. Adherent cells were cultured in serum-free X-VIVO media supplemented with 1000 units/ml each of GM-CSF and IL-4 (R&D Systems, Minneapolis, MN) for six days. DCs were then collected, washed and counted. DCs were loaded with the indicated peptide pool by incubating for one hour at 37° C. in 100 µl XVIVO-15 media supplemented with 1 µg/peptide/ml then used for experiments. PEPMIX™ Peptide pools were synthesized by the manufacturer (JPT, Germany). The survivin peptide pool consists of 33 peptides derived from a peptide scan (15 mers with 11 aa overlap) through Baculoviral IAP repeat-containing protein 5 (Survivin). Positive control peptide pools included CEFT MHCII (14 peptides each corresponding to a defined HLA class II restricted T-cell epitope from Cytomegalovirus, Epstein-Barr virus, Influenza virus or *Clostridium tetani*) and HCMVA (pp65) sourced from the 65 kDa lower matrix phosphoprotein of human cytomegalovirus (strain AD169). The HIV-1 peptide pool (123 peptides selected from Con B gag motifs of HIV), or vehicle only, were used as negative controls as indicated.

T Cell Isolation.

For all experiments, CD4+CD25− T cells were isolated by using magnetic beads from a CD4 negative selection kit supplemented by CD25+ microbeads per the manufacturer's protocol (Miltenyi). PBMCs were incubated for 10 minutes with a biotin-antibody cocktail including CD8, CD14, CD15, CD16, CD19, CD36, CD56, CD123, TCR γ/δ, and CD235a (Glycophorin A) followed by a 15 minute incubation with both anti-biotin and anti-CD25 microbeads. Labeled cells were passed through an LS column and the negative fraction was collected for use in T cell assays.

Proliferation Assay.

[$^3$H]thymidine incorporation assay was performed as previously described (23). Briefly, CD4+CD25− T cells were suspended in X-VIVO-15 (Lonza) media supplemented with 10% human serum (SeraCare, Milford, MA) and penicillin/streptomycin, then seeded into a 96 well flat bottom plate in a ratio of 10:1 with loaded or unloaded DCs. Wells were supplemented with 10 units/ml of IL-2 (R&D Systems) on day 0 and cultured at 37° C. for six days. On day 6 wells were pulsed with radioactive thymidine (PerkinElmer Waltham, MA) for 6 hours then harvested using a Filtermate cell harvester (PerkinElmer). Thymidine incorporation was quantified using a TopCount NXT scintillation counter (PerkinElmer). To calculate the stimulation index 1×10$^5$ CD4+CD25− T cells were stimulated with 1×10$^4$ autologous DCs loaded with survivin (DC:survivin) in a 96 well flat bottom tissue culture plate for 6 days. Proliferation for each well was determined as described above. The stimulation index for each well was calculated against T cells similarly stimulated using unloaded autologous DCs (>=10 replicates per donor). Stimulation Index=[1×10$^5$ CD4+CD25− T cells stimulated with 1×10$^4$ DC:survivin (numerator)]/[Mean of >=10 DC:null stimulated T cell controls (denominator)].

Limiting Dilution Analysis.

The precursor frequencies of survivin-specific CD4+ T cells were determined by limiting dilution analysis as previously described (24). Briefly, CD4+CD25− cells were seeded into 96 well plates in a two-fold descending serial dilution ranging from 100,000 cells/well to 3,125 cells/well in a flat bottom plate and 5,000 to 80 cells/well in a round bottom plate with a total of 10 replicate wells at each concentration. These cells were cocultured with a fixed number of DCs (1×10$^4$ for flat bottom plates or 2×10$^3$ for round bottom) which were either loaded with the survivin peptide pool (DC:survivin) or unloaded (DC:unloaded).

Control wells contained the top concentration of T cells/well for that plate or DCs alone (1×10$^4$ or 2×10$^3$). Cells were cultured at 37° C. for six days in XVIVO-15 media supplemented with 10% human AB serum (SeraCare) and 10 units/ml IL-2 (R&D Systems). On day 6 [$^3$H]thymidine incorporation assay was performed. Publically available extreme limiting dilution analysis software from Walter+ Eliza Hall Bioinformatics (bioinfwehi.edu.au/software/elda/index.html) was used to calculate the frequency and 95% confidence interval (95% CI) of replicating T cells. Wells were considered to be positive if cpm was greater than the mean plus three times the standard deviation of the mean of all unloaded DC control wells (10 or more replicates) at that same T cell concentration.

IFNγ ELISA.

Supernatant was collected from each well and developed using an IFNγ ELISA kit (eBiosciences, San Diego, CA) per the manufacturer's protocol. Briefly, ELISA plates (9018, Corning Costar) were incubated overnight at 4° C. with 1004, purified anti-human IFNγ. Plates were washed and incubated with assay diluent for one hour at room temperature to block the wells from non-specific binding. Plates were washed and incubated for two hours at room temperature with cell culture supernatant or a standard curve created by performing a 2-fold serial dilution of a 500 pg/ml standard. Plates were washed and incubated at room temperature for one hour with 100 µl biotin-conjugated anti-human IFNγ. Plates were then washed again and incubated for 30 minutes at room temperature with 100 µl/well Avidin-HRP. Plates were washed and developed with 100 W TMB substrate solution for 15 minutes. The reaction was stopped by adding 50 µl/well of 1 M phosphoric acid. The ELISA plates were analyzed at 450 nanometers using a Versamax microplate reader equipped with SoftMax Pro 5 software (Molecular Devices, Sunnyvale, CA).

Quantitative PCR.

Messenger RNA was extracted from healthy donor PBMCs or multiple myeloma patient tumor cells by Trizol reaction per the manufacturer's protocol (Invitrogen, Grand Island, NY). mRNA was quantified and assessed for purity using a Nanodrop ND-1000 spectrophotometer (Thermo Scientific, Waltham, MA). cDNA was created using a High Capacity cDNA reverse transcription kit according to the manufacturer's protocol (Applied Biosystems, Waltham, MA). qPCR was performed using an Applied Biosystems 7900 HT Fast Real-Time PCR system in MicroAmp optical 96-well reaction plates using Taqman universal PCR master mix and primer-probe sets for BIRC5 (survivin) and GAPDH genes (Applied Biosystems). Data were analyzed using SDSv2.2.2 software from Applied Biosystems.

Dendritic Cell Transfection.

Following plastic adherent generation, DCs were re-suspended in 500 µL serum-free XVIVO-15 media supplemented with GM-CSF and IL-4 and transfected with 20,000 viral particles/cell of adenovirus expressing double mutant full length survivin (T34A and C84A) for 2 hours at 37° C. (25). After 2 hours, 2×10$^5$ DCs/well were seeded into 24 well plates and supplemented with 1.5 ml of complete culture media (XVIVO-15+10% human serum (SeraCare)+Penicillin/Streptomycin) for an additional 24 hours.

T Cell Expansion.

2×10$^6$ CD4+CD25− T cells/well isolated by magnetic bead negative selection were seeded into 24 well plates containing DCs transfected with survivin adenovirus, peptide pool loaded DCs or unloaded DCs in complete culture media (CCM) supplemented with 10 units/ml IL-2 (R&D Systems). Cells were cultured for 12 days then T cells were collected, washed, counted and re-suspended in CCM without cytokines and rested for 48 hours before use in limiting dilution analysis.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Human CD4+ T Cells Exhibit a Survivin Specific Response

Figure 1A:
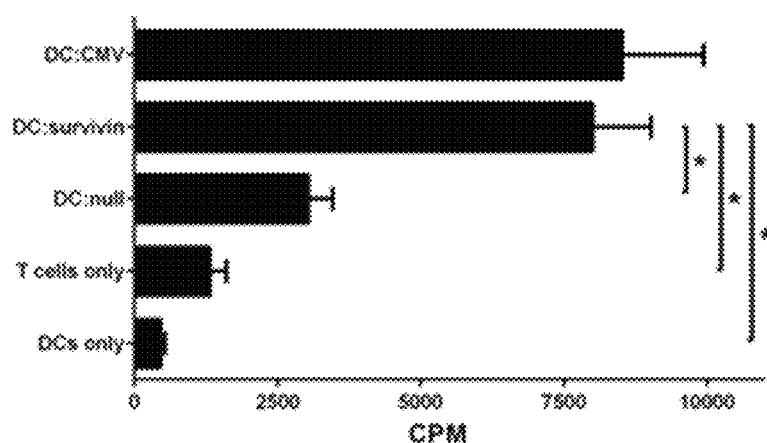
FIGS. 1A-1C. Healthy donor CD4+CD25− T cells proliferate and secrete IFN-gamma in response to survivin peptide pools presented by autologous dendritic cells. $1\times10^5$ Purified CD4+CD25− cells were stimulated for 6 days with $1\times10^4$ autologous DCs loaded with CMV peptide pool (DC:CMV) positive control, survivin peptide pool (DC:survivin), or unloaded (DC:null) negative control. Proliferation (FIG. 1A) and IFN-gamma secretion (FIG. 1B) were elicited by DC:survivin, figures represent the mean of three independent experiments from different healthy donors and error bar represents standard error of the mean. For 10 consecutive evaluable healthy donors, a stimulation index was calculated (FIG. 1C) [$1\times10^5$ CD4+CD25− T cells stimulated with $1\times10^4$ DC:survivin (numerator)/Mean of $>=10$ DC:null stimulated T cell controls (denominator)]. Box and whiskers represents multiple stimulation indices (Line=Mean, Box=25%-75% CI, Whiskers=minimum and maximum) for each donor. *p<0.05.
Figure 1B:
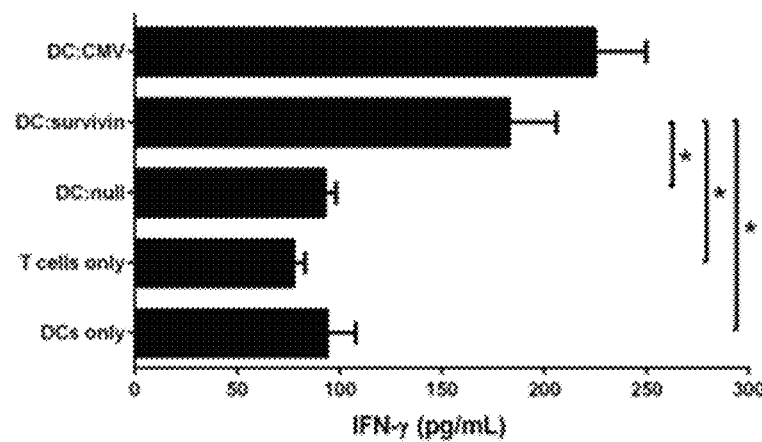
Figure 1C:
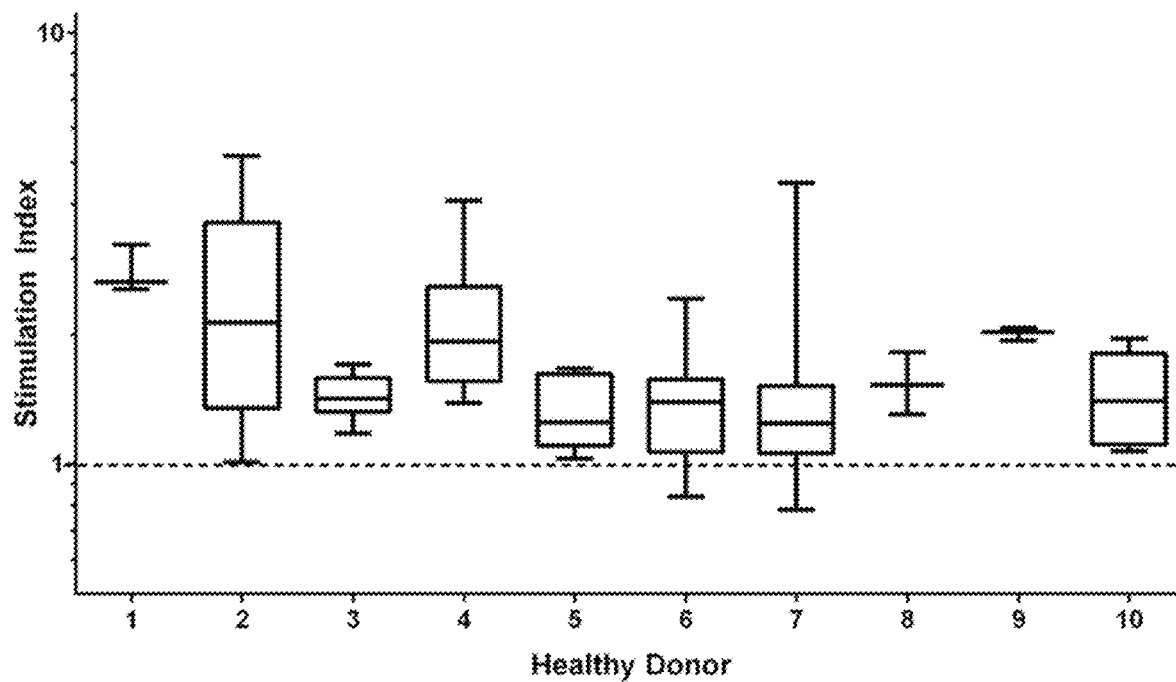

The response of unprimed conventional human CD4+CD25− T cells against survivin was evaluated by quantifying proliferation and IFN-gamma cytokine release against a peptide pool (JPT) derived from survivin. Because the peptides are not restricted to a single HLA type, testing of human T cells does not require HLA typing and stratification since the likelihood of detecting a response is magnified by the pool of peptides. CD4+CD25− T cells from healthy patients proliferate in response to survivin peptide pools loaded onto autologous monocyte derived dendritic cells, similar to responses against common viral antigens (FIG. 1A). After 6 days of co-culture, IFN-gamma was detectable within the supernatant (FIG. 1B). To evaluate the reactivity of healthy donor CD4+ cells against survivin the inventors determined the stimulation index for 10 consecutive healthy donors (3-12 replicates per donor). CD4+ proliferative response against survivin was detectable in all 10 healthy donors tested (FIG. 1C). Not every well containing 100,000 CD4+ cells exhibited proliferative responses exceeding the autologous mixed lymphocyte response.

Figure 2A:
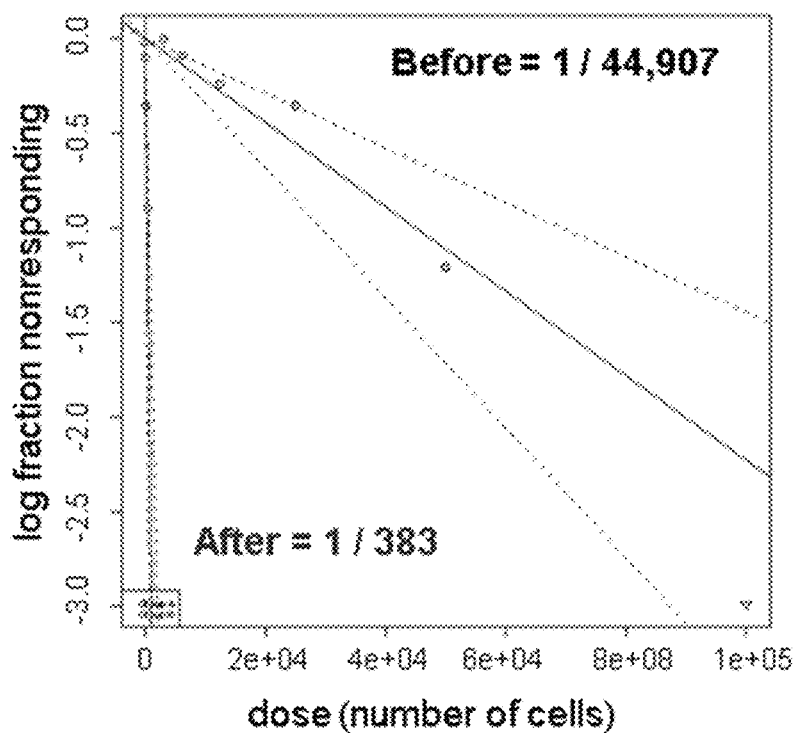
FIGS. 2A and 2B. Limiting dilution analysis (LDA) determines the frequency of survivin-reactive CD4+CD25− T cells in normal human blood. Serially diluted, purified CD4+CD25− T cells were stimulated with autologous DC:survivin in the presence of exogenous IL-2. Each LDA was performed with a minimum of 10 replicates per cell concentration.
Figure 2B:
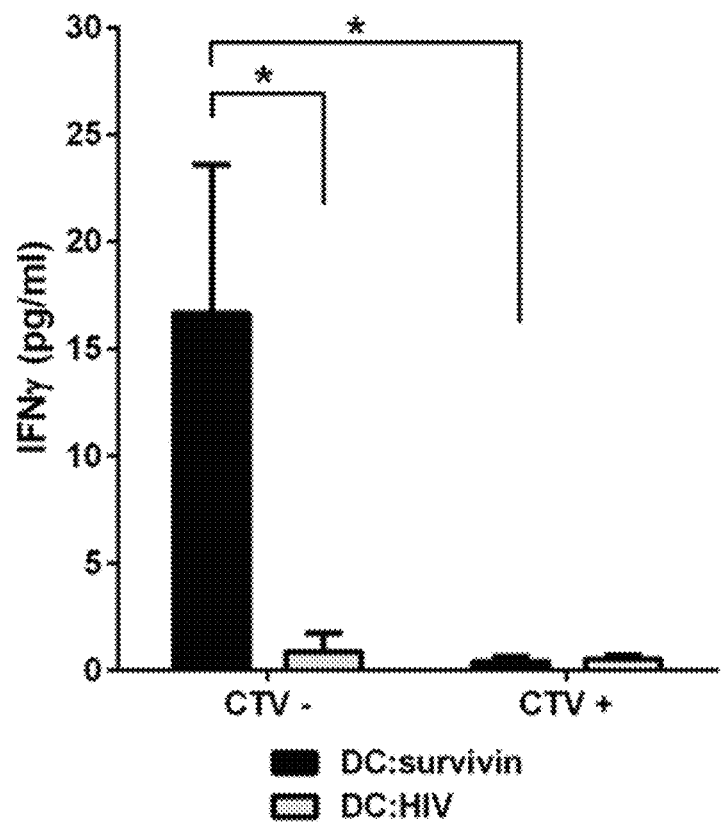

Example 2—Limiting Dilution Analysis Quantifies the Frequency of Survivin-Reactive CD4+ T Cells To quantify the precursor frequency of survivin-specific T cells the inventors performed limiting dilution analysis (LDA) of CD4+CD25− T cells against a fixed dendritic cell concentration (FIG. 2A, Before). To validate that the proliferation measured in the LDA was indeed due to reactivity specifically against survivin, CD4+CD25− T cells were concurrently expanded, under the same conditions, for 12 days. Repeat LDA showed the frequency of survivin-responsive T cells increased approximately 100-fold (FIG. 2A, After), and the absolute survivin-specific cell number increased 200-fold (data not shown). The inventors next confirmed that T cells expanded using DC:survivin were able to secrete IFN-gamma in response to survivin. Before initial DC:survivin stimulation, CD4+CD25+ cells were labeled with the proliferative marker cell trace violet (CTV). Following 12 days of expansion with DC:survivin, CD4+ cells were flow sorted into CTV− (replicated) and CTV+ (non-replicated) populations. Replicated T cells showed a significant secretion of IFN-gamma (FIG. 2B) upon re-challenge with DC:survivin as compared to DCs loaded with an irrelevant HIV protein peptide pool (DC:HIV). Non-replicated CD4+ T cells did not respond to either peptide pool stimulus.

Figure 3A:
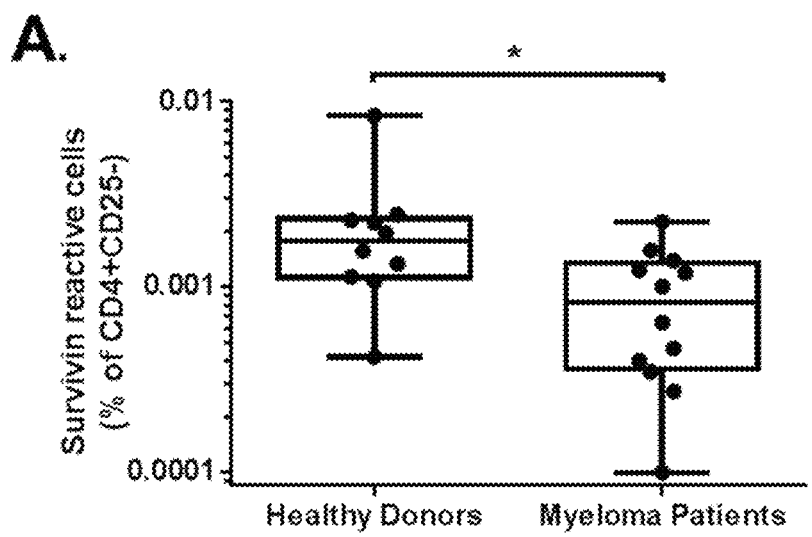
FIGS. 3A-3C. Myeloma patients harbor survivin specific CD4+CD25− T cells which respond to survivin peptide pool loaded autologous DCs.
Figure 3B:
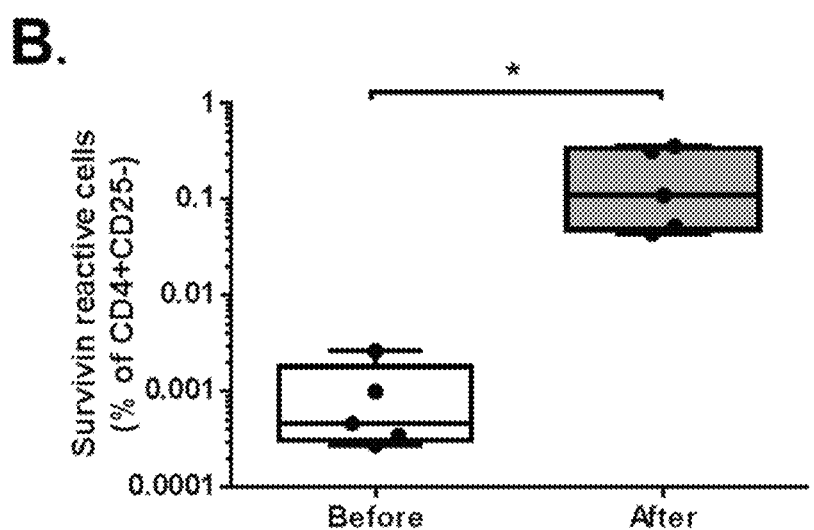
Figure 3C:
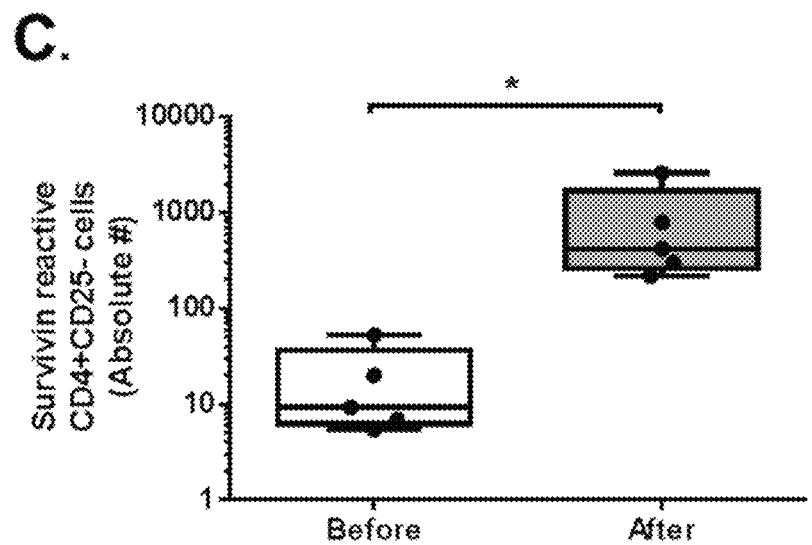

Example 3—Multiple Myeloma Patients have Fewer Survivin-Reactive CD4+ T Cells than Healthy Blood Donors It was previously shown that myeloma patients can harbor CD4 and CD8 T cells reactive against survivin; however, this required multiple stimulation and expansion steps, precluding a precise quantification of the circulating T cell precursor frequency. The inventors next evaluated the precursor frequency of survivin-reactive T cells in the peripheral blood of 10 consecutive healthy donors and 12 consecutive multiple myeloma patients. Myeloma patients had a significantly lower precursor frequency of survivin-reactive CD4+CD25− cells (range 0% to 2.2×10-3%) compared to healthy donors (range 1.1×10-3 to 8.4×10-3%) (FIG. 3A). Similar to healthy donors, myeloma patient CD4+CD25− T cells expand in response to DC:survivin stimulation (FIGS. 3B-3C).

Figure 4A:
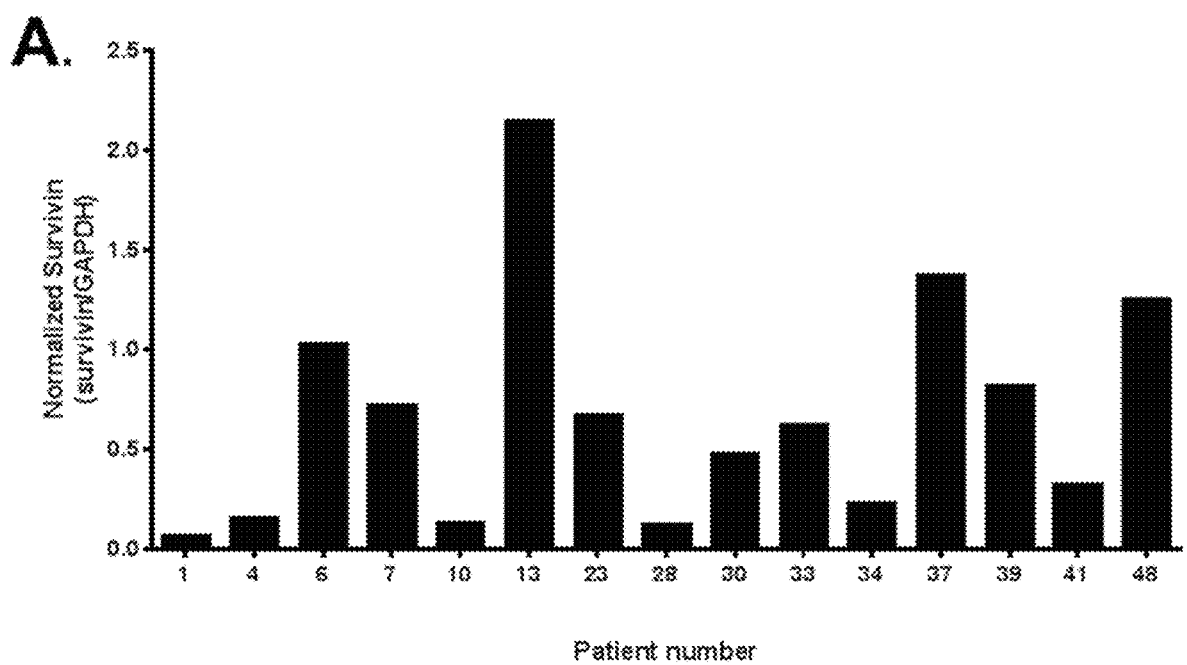
FIGS. 4A and 4B. Multiple myeloma tumors express survivin mRNA transcripts which inversely correlate with survivin-reactive CD4+ T cell frequency.
Figure 4B:
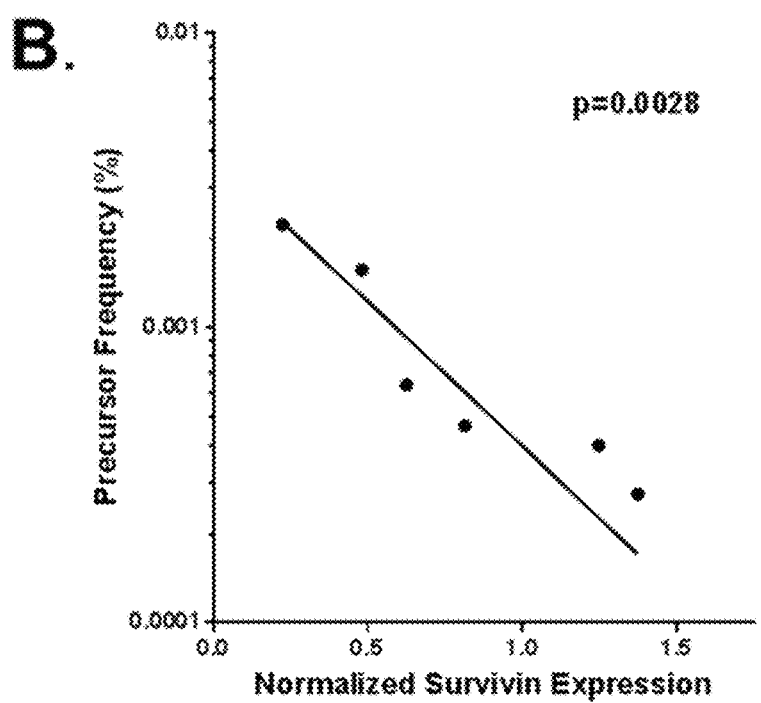

Example 4—Multiple Myeloma Tumor Survivin Expression Inversely Correlates with Survivin-Reactive CD4+ T Cell Frequency Purified CD138+ primary multiple myeloma patient tumor cells from patients' bone marrow aspirates express survivin mRNA at a frequency similar to that described by others (FIG. 4A). Survivin protein also can be detected by IHC from concordant bone marrow biopsies (data not shown). Survivin-specific precursor frequency and survivin mRNA transcripts were evaluated for 6 consecutive MM patients having adequate samples. There is an inverse correlation between a patient's survivin-reactive CD4+CD25− precursor frequency and their tumor's survivin expression by PCR (FIG. 4B).

Figure 5A:
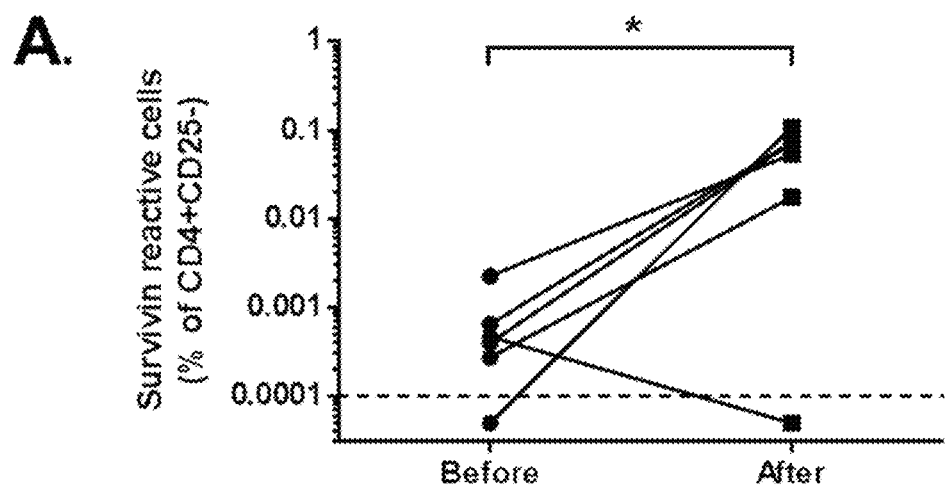
FIGS. 5A and 5B. A full length survivin protein vaccine expands survivin-specific CD4+ cells even in patients with a low survivin-reactive precursor frequency.
Figure 5B:
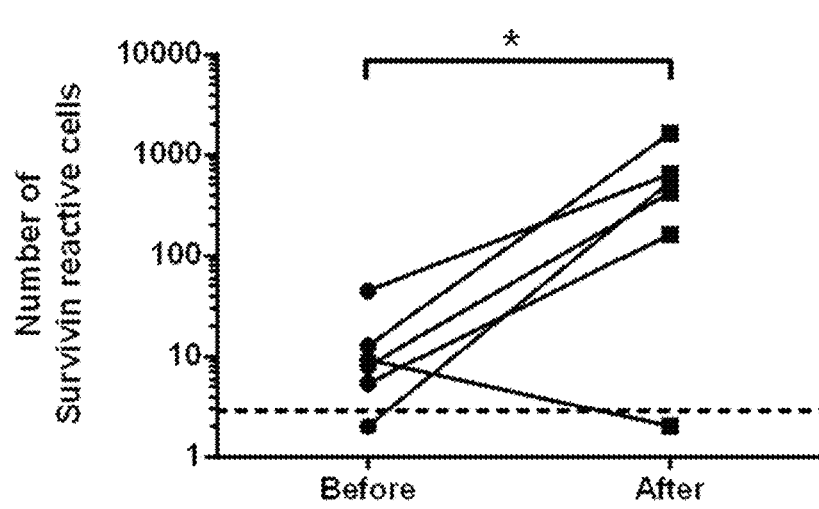
Figure 6:
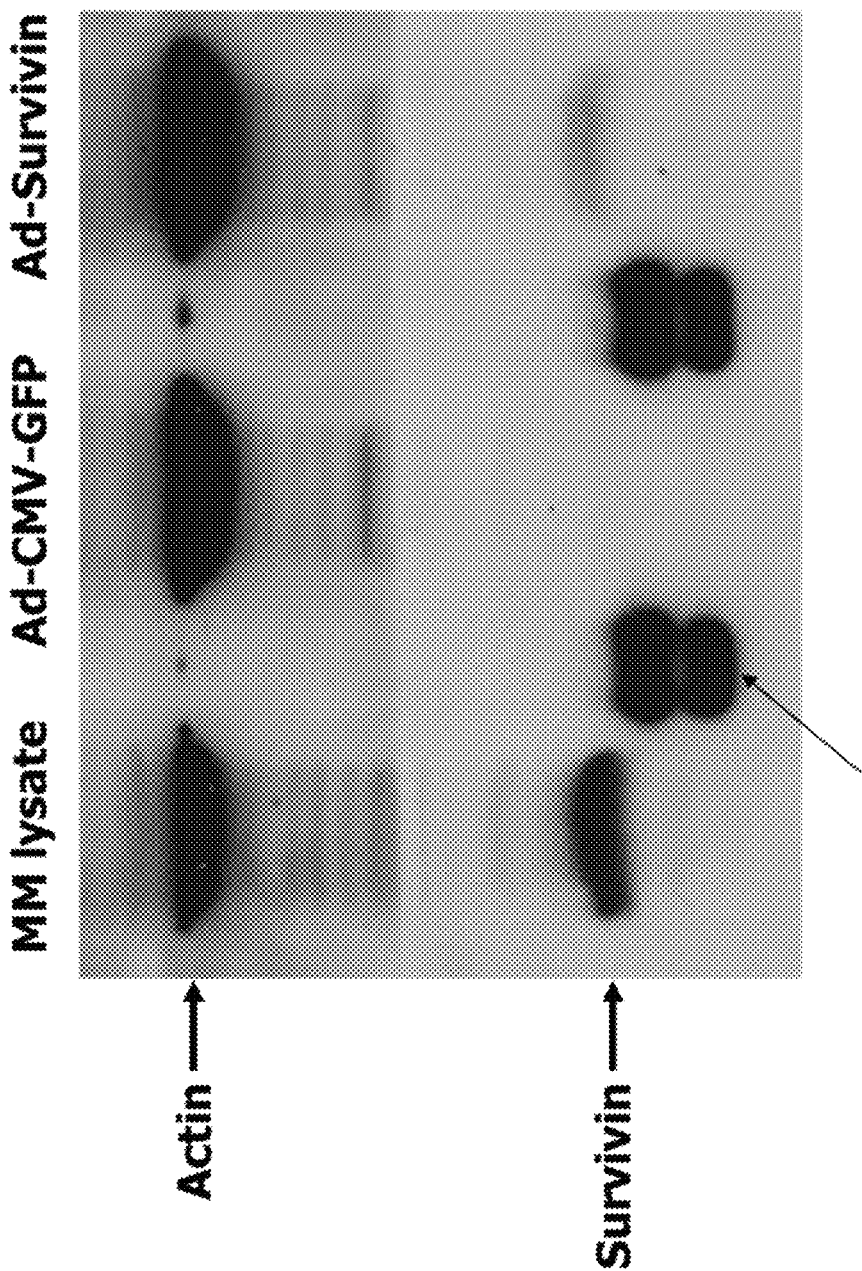
FIGS. 6-8.
Figure 7:
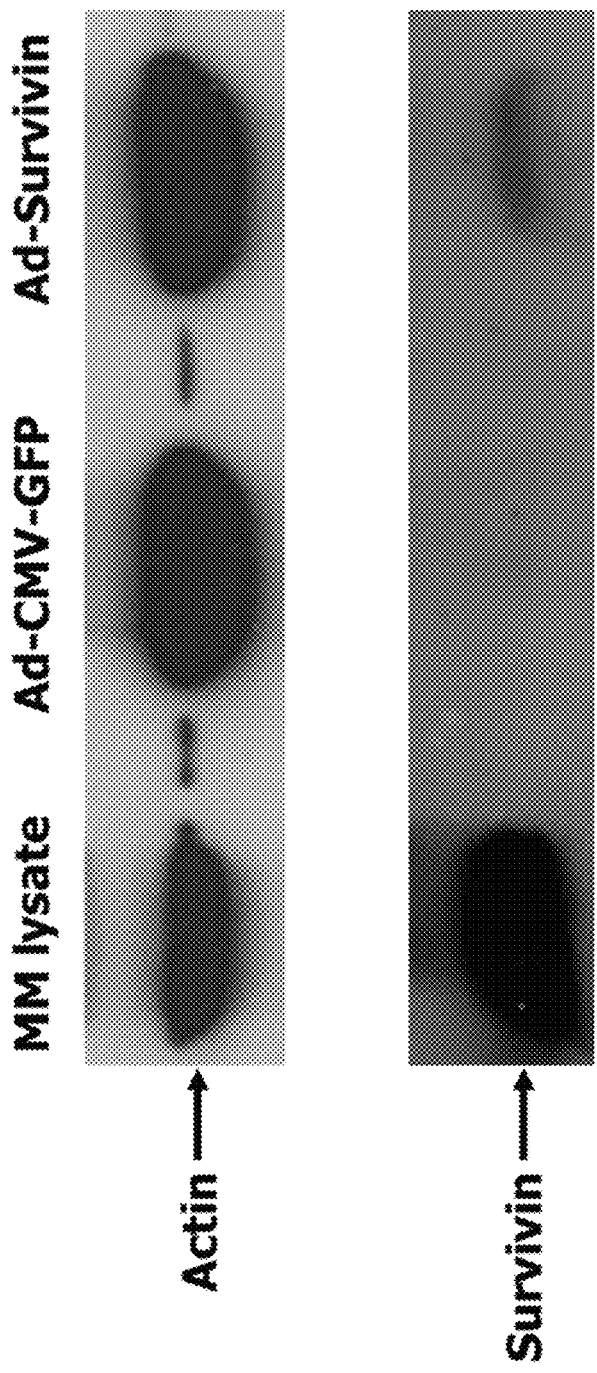
Figure 8:
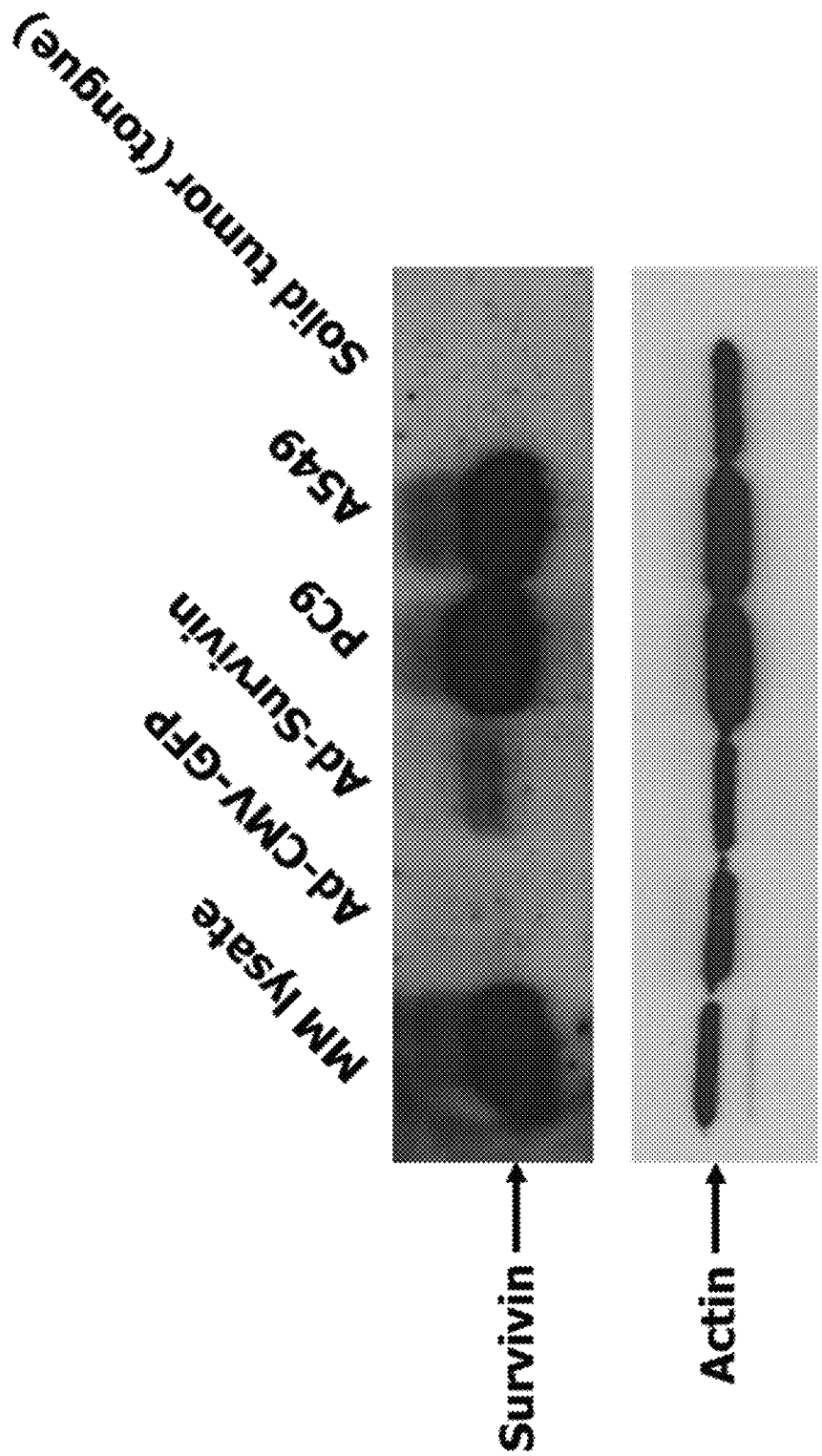
Figure 9:
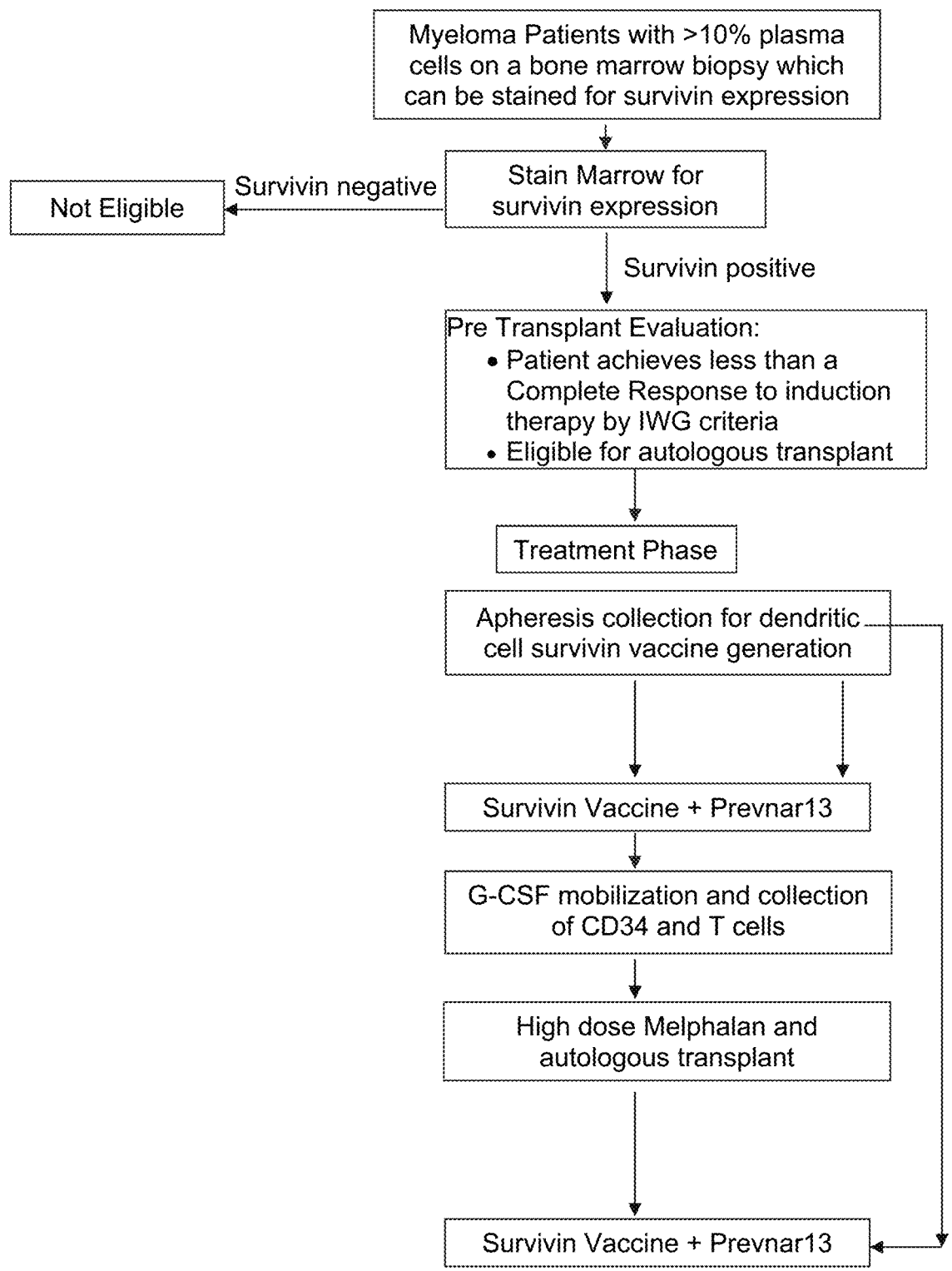
FIG. 9. Treatment schema using survivin variant polypeptide and Prevnar 13 (Prevnar 13, Pneumococcal 13-valent Conjugate Vaccine (Diphtheria CRM197 Protein)) with autologous hematopoietic transplant.

Example 5—a Full-Length Survivin Protein Vaccine Elicits CD4+ T Cell Responses in Myeloma Patients Despite Low Baseline Survivin-Reactive CD4+ Precursor Frequencies The inventors tested the ability of a full-length survivin protein vaccine to expand myeloma CD4+CD25− T cells that are reactive against survivin peptide pool loaded autologous DCs. The previously characterized vaccine consists of an adenoviral construct (Ad-ms), which upon infection of autologous DCs (DC:Ad-ms), leads to expression and antigen presentation of a mutated survivin protein. This approach allows for preservation of multiple epitopes, which upon DC antigen presentation are more likely to capture and expand survivin-reactive T cells than single or oligo-peptide survivin vaccines. The survivin-reactive frequency was determined before and after myeloma patient CD4+CD25− T cells were co-cultured with autologous DCs infected with Ad-ms (FIG. 5A). Survivin-reactive CD4+ T cell frequency and absolute number of survivin-reactive T cells (FIG. 5B) was increased after co-culture (fold expansion range 0-270×, median=42×). The vaccine was able to expand survivin-reactive cells even from myeloma patients with a low pre co-culture survivin-specific precursor frequency (near or below the limit of detection of the LDA assay). The survivin-reactive precursor frequency of CD4+CD25− cells was not predictive of the number of survivin-reactive cells obtained after expansion (r=0.429, p=0.4194 by Spearman correlation analysis).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

References for Examples 1-5

1. Ambrosini G, Adida C, Altieri D C. A novel anti-apoptosis gene, survivin, expressed in cancer and lymphoma. Nat Med. 1997; 3:917-21.
2. Kawasaki H, Altieri D C, Lu C D, Toyoda M, Tenjo T, Tanigawa N. Inhibition of apoptosis by survivin predicts shorter survival rates in colorectal cancer. Cancer Res. 1998; 58:5071-4.
3. Swana H S, Grossman D, Anthony J N, Weiss R M, Altieri D C. Tumor content of the antiapoptosis molecule survivin and recurrence of bladder cancer. N Engl J Med. 1999; 341:452-3.
4. Tanaka K, Iwamoto S, Gon G, Nohara T, Iwamoto M, Tanigawa N. Expression of survivin and its relationship to loss of apoptosis in breast carcinomas. Clin Cancer Res. 2000; 6:127-34.
5. Stauber R H, Mann W, Knauer S K. Nuclear and cytoplasmic survivin: molecular mechanism, prognostic, and therapeutic potential. Cancer Res. 2007; 67:5999-6002.
6. Nakagawa Y, Abe S, Kurata M, Hasegawa M, Yamamoto K, Inoue M, et al. IAP family protein expression correlates with poor outcome of multiple myeloma patients in association with chemotherapy-induced overexpression of multidrug resistance genes. Am J Hematol. 2006; 81:824-31.
7. Romagnoli M, Trichet V, David C, Clement M, Moreau P, Bataille R, et al. Significant impact of survivin on myeloma cell growth. Leukemia. 2007; 21:1070-8.
8. Grube M, Moritz S, Obermann E C, Rezvani K, Mackensen A, Andreesen R, et al. CD8+ T cells reactive to survivin antigen in patients with multiple myeloma. Clin Cancer Res. 2007; 13:1053-60.
9. Idenoue S, Hirohashi Y, Torigoe T, Sato Y, Tamura Y, Hariu H, et al. A potent immunogenic general cancer vaccine that targets survivin, an inhibitor of apoptosis proteins. Clin Cancer Res. 2005; 11:1474-82.
10. Schmitz M, Diestelkoetter P, Weigle B, Schmachtenberg F, Stevanovic S, Ockert D, et al. Generation of survivin-specific CD8+ T effector cells by dendritic cells pulsed with protein or selected peptides. Cancer Res. 2000; 60:4845-9.
11. Xiang R, Mizutani N, Luo Y, Chiodoni C, Zhou H, Mizutani M, et al. A DNA vaccine targeting survivin combines apoptosis with suppression of angiogenesis in lung tumor eradication. Cancer Res. 2005; 65:553-61.
12. Becker J C, Andersen M H, Hofmeister-Muller V, Wobser M, Frey L, Sandig C, et al. Survivin-specific T-cell reactivity correlates with tumor response and patient survival: a phase-II peptide vaccination trial in metastatic melanoma. Cancer Immunol Immunother. 2012; 61:2091-103.
13. Hung K, Hayashi R, Lafond-Walker A, Lowenstein C, Pardoll D, Levitsky H. The central role of CD4(+) T cells in the antitumor immune response. J Exp Med. 1998; 188:2357-68.
14. Hirschhorn-Cymerman D, Budhu S, Kitano S, Liu C, Zhao F, Zhong H, et al. Induction of tumoricidal function in CD4+ T cells is associated with concomitant memory and terminally differentiated phenotype. J Exp Med. 2012; 209:2113-26.
15. Casati C, Dalerba P, Rivoltini L, Gallino G, Deho P, Rini F, et al. The apoptosis inhibitor protein survivin induces 15. tumor-specific CD8+ and CD4+ T cells in colorectal cancer patients. Cancer Res. 2003; 63:4507-15.
16. Piesche M, Hildebrandt Y, Zettl F, Chapuy B, Schmitz M, Wulf G, et al. Identification of a promiscuous HLA D R-restricted T-cell epitope derived from the inhibitor of apoptosis protein survivin. Human immunology. 2007; 68:572-6.
17. Wang X F, Kerzerho J, Adotevi O, Nuyttens H, Badoual C, Munier G, et al. Comprehensive analysis of HLA-D R- and HLA-DP4-restricted CD4+ T cell response specific for the tumor-shared antigen survivin in healthy donors and cancer patients. J Immunol. 2008; 181:431-9.
18. Tanaka M, Butler M O, Ansen S, Imataki O, Berezovskaya A, Nadler L M, et al. Induction of HLA-DP4-restricted anti-survivin Th1 and Th2 responses using an artificial antigen-presenting cell. Clin Cancer Res. 2011; 17:5392-401.
19. Widenmeyer M, Griesemann H, Stevanovic S, Feyerabend S, Klein R, Attig S, et al. Promiscuous survivin peptide induces robust CD4+ T-cell responses in the majority of vaccinated cancer patients. Int J Cancer. 2012; 131:140-9.
20. Levitsky H I, Lazenby A, Hayashi R J, Pardoll D M. In vivo priming of two distinct antitumor effector populations: the role of MEW class I expression. J Exp Med. 1994; 179:1215-24.
21. Corthay A, Skovseth D K, Lundin K U, Rosjo E, Omholt H, Hofgaard P O, et al. Primary antitumor immune response mediated by CD4+ T cells. Immunity. 2005; 22:371-83.
22. Gerdemann U, Katari U, Christin A S, Cruz C R, Tripic T, Rousseau A, et al. Cytotoxic T lymphocytes simultaneously targeting multiple tumor-associated antigens to treat EBV negative lymphoma. Mol Ther. 2011; 19:2258-68.
23. Locke F L, Zha Y Y, Zheng Y, Driessens G, Gajewski T F. Conditional deletion of PTEN in peripheral T cells augments TCR-mediated activation but does not abrogate CD28 dependency or prevent anergy induction. J Immunol. 2013; 191:1677-85.
24. Veerapathran A, Pidala J, Beato F, Yu X Z, Anasetti C. Ex vivo expansion of human Tregs specific for alloantigens presented directly or indirectly. Blood. 2011; 118: 5671-80.
25. Nagaraj S, Pisarev V, Kinarsky L, Sherman S, Muro-Cacho C, Altieri D C, et al.
Dendritic cell-based full-length survivin vaccine in treatment of experimental tumors. J Immunother. 2007; 30:169-79.
26. Weber G, Caruana I, Rouce R H, Barrett A J, Gerdemann U, Leen A M, et al. Generation of tumor antigen-specific T cell lines from pediatric patients with acute lymphoblastic leukemia—implications for immunotherapy. Clin Cancer Res. 2013; 19:5079-91.
27. de Haart S J, van de Donk N W, Minnema M C, Huang J H, Aarts-Riemens T, Bovenschen N, et al. Accessory cells of the microenvironment protect multiple myeloma from T-cell cytotoxicity through cell adhesion-mediated immune resistance. Clin Cancer Res. 2013; 19:5591-601.
28. Locke F L, Nishihori T, Alsina M, Kharfan-Dabaja M A. Immunotherapy strategies for multiple myeloma: the present and the future. Immunotherapy. 2013; 5:1005-20.
29. Han S, Wang B, Cotter M J, Yang L J, Zucali J, Moreb J S, et al. Overcoming immune tolerance against multiple myeloma with lentiviral calnexin-engineered dendritic cells. Mol Ther. 2008; 16:269-79.
30. Prabhala R H, Neri P, Bae J E, Tassone P, Shammas M A, Allam C K, et al. Dysfunctional T regulatory cells in multiple myeloma. Blood. 2006; 107:301-4.
31. Beyer M, Kochanek M, Giese T, Endl E, Weihrauch M R, Knolle P A, et al. In vivo peripheral expansion of naive CD4+CD25high FoxP3+ regulatory T cells in patients with multiple myeloma. Blood. 2006; 107:3940-9.
32. Noonan K, Marchionni L, Anderson J, Pardoll D, Roodman G D, Borrello I. A novel role of IL-17-producing lymphocytes in mediating lytic bone disease in multiple myeloma. Blood. 2010; 116:3554-63.
33. Gorgun G T, Whitehill G, Anderson J L, Hideshima T, Maguire C, Laubach J, et al. Tumor-promoting immune-suppressive myeloid-derived suppressor cells in the multiple myeloma microenvironment in humans. Blood. 2013; 121:2975-87.
34. Favaloro J, Liyadipitiya T, Brown R, Yang S, Suen H, Woodland N, et al. Myeloid derived suppressor cells are numerically, functionally and phenotypically different in patients with multiple myeloma. Leuk Lymphoma. 2014: 1-8.
35. Ramachandran I R, Martner A, Pisklakova A, Condamine T, Chase T, Vogl T, et al. Myeloid-derived suppressor cells regulate growth of multiple myeloma by inhibiting T cells in bone marrow. J Immunol. 2013; 190:3815-23.
36. Shain K H, Dalton W S. Environmental-mediated drug resistance: a target for multiple myeloma therapy. Expert review of hematology. 2009; 2:649-62.
37. Bonanno G, Mariotti A, Procoli A, Folgiero V, Natale D, De Rosa L, et al. Indoleamine 2,3-dioxygenase 1 (IDO1) activity correlates with immune system abnormalities in multiple myeloma. Journal of translational medicine. 2012; 10:247.
38. Prabhala R H, Pelluru D, Fulciniti M, Prabhala H K, Nanjappa P, Song W, et al. Elevated IL-17 produced by TH17 cells promotes myeloma cell growth and inhibits immune function in multiple myeloma. Blood. 2010; 115:5385-92.
39. Dhodapkar K M, Barbuto S, Matthews P, Kukreja A, Mazumder A, Vesole D, et al. Dendritic cells mediate the induction of polyfunctional human IL17-producing cells (Th17-1 cells) enriched in the bone marrow of patients with myeloma. Blood. 2008; 112:2878-85.
40. Tamura H, Ishibashi M, Yamashita T, Tanosaki S, Okuyama N, Kondo A, et al. Marrow stromal cells induce B7-H1 expression on myeloma cells, generating aggressive characteristics in multiple myeloma. Leukemia. 2013; 27:464-72.
41. Zheng Y, Zha Y, Driessens G, Locke F, Gajewski T F. Transcriptional regulator early growth response gene 2 (Egr2) is required for T cell anergy in vitro and in vivo. J Exp Med. 2012; 209:2157-63.
42. Fields P E, Gajewski T F, Fitch F W. Blocked Ras activation in anergic CD4+ T cells. Science. 1996; 271: 1276-8.
43. Brown R, Murray A, Pope B, Sze D, Gibson J, Ho P J, et al. B7+ T cells in myeloma: an acquired marker of prior chronic antigen presentation. Leuk Lymphoma. 2004; 45:363-71.
44. Rosenblatt J, Glotzbecker B, Mills H, Vasir B, Tzachanis D, Levine J D, et al. PD-1 blockade by CT-011, anti-PD-1 antibody, enhances ex vivo T-cell responses to autologous dendritic cell/myeloma fusion vaccine. J Immunother. 2011; 34:409-18.

45. Brown R D, Pope B, Yuen E, Gibson J, Joshua D E. The expression of T cell related costimulatory molecules in multiple myeloma. Leuk Lymphoma. 1998; 31:379-84.
46. Mesri M, Wall N R, Li J, Kim R W, Altieri D C. Cancer gene therapy using a survivin mutant adenovirus. The Journal of clinical investigation. 2001; 108:981-90.
47. Pisarev V, Yu B, Salup R, Sherman S, Altieri D C, Gabrilovich D I. Full-length dominant-negative survivin for cancer immunotherapy. Clin Cancer Res. 2003; 9:6523-33.
48. Lim S H, Badros A, Lue C, Barlogie B. Distinct T-cell clonal expansion in the vicinity of tumor cells in plasmacytoma. Cancer. 2001; 91:900-8.

Example 6—T Cells Specific for Survivin are Decreased in Myeloma Patients Compared to Healthy Donors Multiple myeloma is the second most common hematologic malignancy in adults with approximately 20,000 patients diagnosed per year in the United States.[1] The disease is characterized by the proliferation of clonal plasma cells preferentially in the bone marrow, resulting in anemia, osteolytic bone disease and the detection of a monoclonal gammopathy in the majority of the patients.[2] The current standard therapy consists of induction therapy with immunomodulatory drugs or proteasome inhibitor based-regimens, followed by autologous stem cell transplants in those patients with responsive disease.[3-6] These treatment modalities induce high rates of complete remission and significantly improved survival. However, molecular remissions are rare, and a significant proportion of patients are unable to achieve a complete response (CR) to induction therapy both before and after transplant. Inevitably all patients relapse and die due to disease progression.[7] Therefore, the development of novel interventions for patients with resistant disease and to target minimal residual disease after autologous bone marrow transplantation is greatly needed.

Survivin is a small inhibitor of apoptosis protein that functions as a mitotic regulator and an apoptosis inhibitor.[8] The role of survivin in the regulation of mitosis is linked to multiple spindle microtubule functions and mitotic checkpoints.[9] Survivin is known to interfere with caspase 9 processing, the upstream initiation of the intrinsic pathway of apoptosis.[10] Survivin is abundantly expressed in development, but is undetectable in most adult tissues, except for thymocytes, CD34 bone marrow derived stem cells, and colonic epithelial cells.[11] In contrast, survivin is over expressed in almost all cancers including lung, colon, breast pancreas, stomach, liver, ovary, prostate, melanoma and hematologic malignancies.[12-16] High survivin expression in cancer has been shown to carry poor prognosis and has been consistently associated with advanced disease, drug resistance, early relapses and decreased survival.[17]

Multiple studies have shown survivin over expression in myeloma cells lines and primary cells and a correlation of its expression to poor prognosis and drug resistance. Li et al. examined the RNA and protein expression of survivin in bone marrow of healthy individuals and multiple myeloma patients.[18] Survivin protein was not detected in healthy individuals while it was expressed in 41.4% of newly diagnosed myeloma patients and 58.3% of relapsed refractory patients. Their study also suggested a better response rate in patients without survivin expression and these findings have been supported by other investigators.[7]

In a study by Romagnoli et al[19] a significant correlation was found between survivin expression and myeloma progression with high survivin expression in patients with relapsed and extramedullary myeloma when compared to a cohort of newly diagnosed patients. In cell lines they were able to show that silencing of survivin expression sensitizes the myeloma cells to cytotoxic chemotherapy such as doxorubicin, dexamethasone and melphalan. Grube et al.[20] provided evidence of T cell reactivity against survivin antigen in myeloma patients suggesting that immunotherapeutic strategies using survivin as a target antigen may be useful in myeloma.

Multiple myeloma patients treated at Moffitt Cancer Center have tumors expressing survivin protein and mRNA. The inventors evaluated 28 patients' bone marrow biopsies for the presence of tumor specific survivin expression. All biopsies were done as part of the pre-transplant evaluation (post induction chemotherapy) and all had measurable disease in the marrow (>5% CD138+ cells). Using methods described in section 5.1, 9 of 28 patients (32%) were survivin positive, a rate similar to that described by others (FIG. 15A). In a separate cohort of 15 patients, the inventors purified CD138+ cells from bone marrow aspirates. Quantitative PCR was performed revealing survivin expression significantly greater than healthy donor PBMC controls in 60% of patients, and very high expression in 33% (FIG. 15B). This preliminary data shows that our patient population with less than a CR after induction therapy does express both survivin protein and mRNA.

Figure 10A:
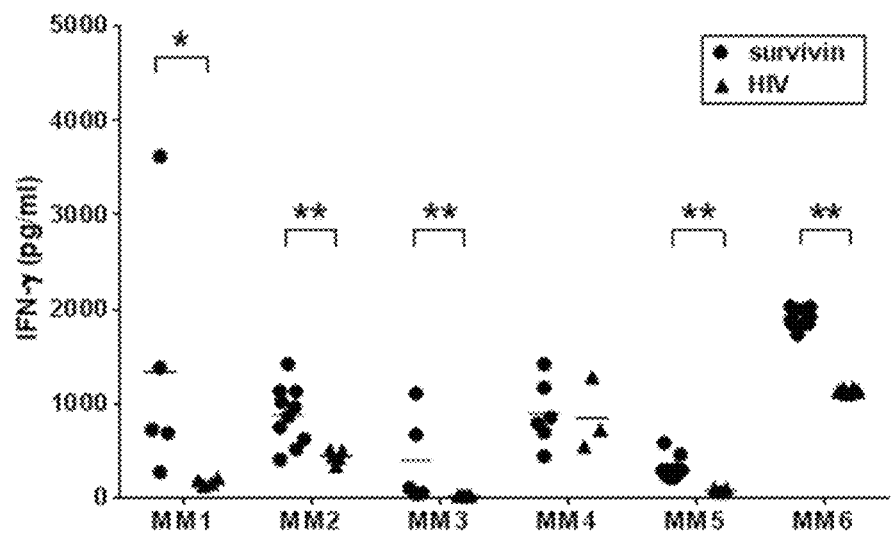
FIGS. 10A and 10B. Survivin peptide pools co-cultured with myeloma patient PBMCs elicit IFN-gamma release and proliferation. Myeloma patient PBMCs were collected by apheresis before autologous transplant, then were co-cultured with survivin peptide pool or a negative control pool (HIV). After 6 days of co-culture in the presence of IL-7 and IL-15, supernatant was collected for IFN-gamma ELISA (FIG. 10A), or proliferation was measured by 8 hour thymidine incorporation (FIG. 10B).
Figure 10B:
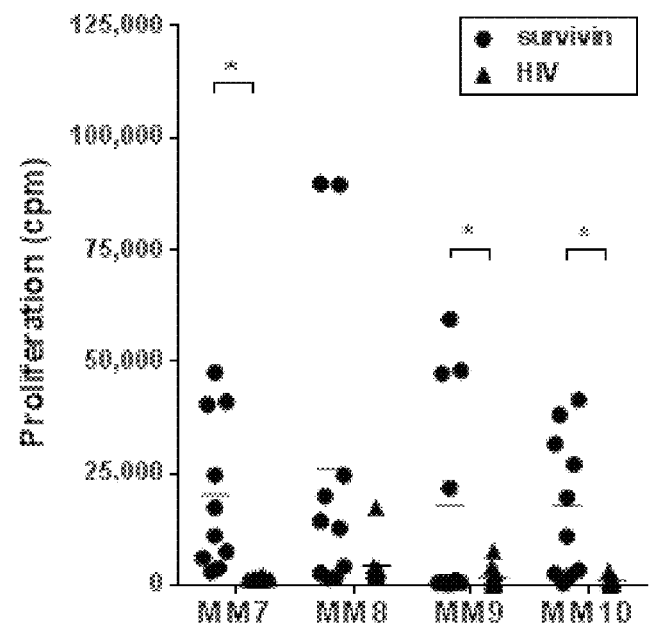
Figure 11A:
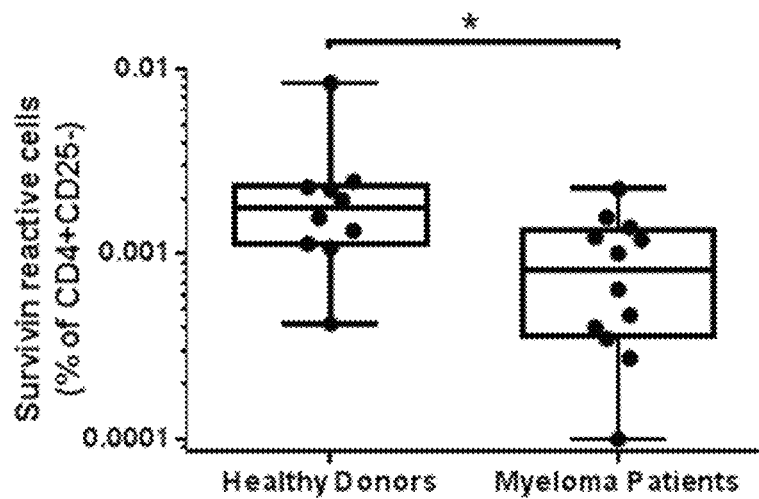
FIGS. 11A and 11B. Myeloma patients' survivin specific CD4+CD25− T cells can be directly quantified and inversely correlate with tumor survivin mRNA expression.

Survivin specific T cells exist in multiple myeloma patients (FIGS. 10A-10B). The inventors evaluated the precursor frequency of survivin reactive T cells in the peripheral blood of 10 consecutive healthy donors and 12 consecutive multiple myeloma patients. Myeloma patients had a significantly lower precursor frequency of survivin reactive CD4+CD25− cells (range 0% to $2.2 \times 10{-3}$%) compared to healthy donors (range $1.1 \times 10{-3}$ to $8.4 \times 10{-3}$%) (FIG. 11A).

Our pre-cursor frequency assay utilizes T cell limiting dilution analysis with stimulation by autologous DC loaded with a survivin peptide pool, or unloaded as a control. The pool consists of 15mers with an overlap of 11 amino acids spanning the entire survivin protein, synthesized, purified, and analyzed by liquid crystallography by the manufacturer, JPT (Germany). Patients need not be stratified by HLA type, since the likelihood of detecting a response is magnified by the pool of peptides.[21,22] This approach does not limit immune monitoring to patients with a certain HLA type, and will allow for measurement of functional survivin specific CD4 or CD8 T cells in patients vaccinated using a whole survivin protein.

Figure 11B:
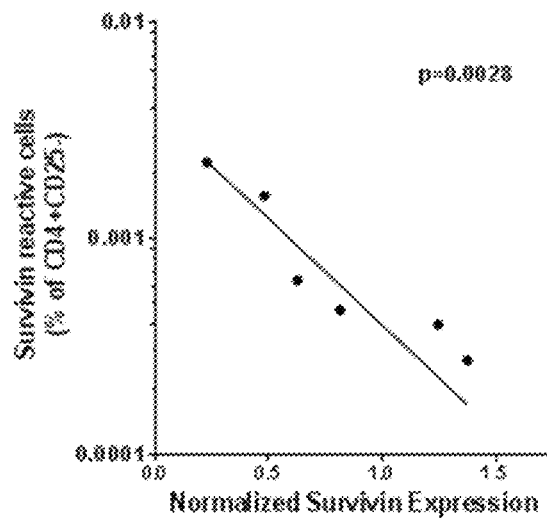

Example 7—Multiple Myeloma Tumor Survivin Expression Inversely Correlates with Survivin Reactive CD4+ T Cell Frequency Survivin specific T cell precursor frequency and tumor survivin mRNA transcripts were evaluated for 6 consecutive MM patients having adequate samples. There is an inverse correlation between a patient's survivin reactive CD4+ CD25− precursor frequency and their tumor's survivin expression by PCR (FIG. 11B).

Example 8—a Full Length Survivin Protein Vaccine Elicits T Cell Responses in Myeloma Patients Despite Low Baseline Survivin Reactive T Cell Precursor Frequencies The inventors tested the ability of a full length survivin protein vaccine to expand survivin reactive T cells from myeloma patients.

The previously described vaccine consists of an adenoviral construct (Ad-ms), which upon infection of autologous DCs (DC:Ad-ms), leads to expression and antigen presentation of a mutated survivin protein. This approach allows for preservation of multiple epitopes, which upon DC antigen presentation are more likely to capture and expand survivin reactive T cells than single or oligo-peptide survivin vaccines.

The survivin reactive frequency was determined before and after myeloma patient CD4+CD25− T cells were co-cultured with autologous DCs infected with Ad-ms. Survivin reactive CD4+ T cell frequency (not shown) and absolute number of survivin reactive T cells (FIG. 12A) was increased after co-culture (fold expansion range 0-270×, median=42×). The vaccine was able to expand survivin reactive cells even from myeloma patients with a low pre co-culture survivin specific precursor frequency (near or below the limit of detection of the LDA assay). The survivin reactive precursor frequency of CD4+CD25− cells was not predictive of the number of survivin reactive cells obtained after expansion (r=0.429, p=0.4194 by Spearman correlation analysis).

Importantly CD3+ T cells expanded using the vaccine do not secrete IFN-gamma in response to irrelevant HIV protein peptide pools loaded on autologous DCs but do exhibit significant responses against survivin (FIG. 12B).

Both survivin antagonists and survivin peptide vaccines have been tested. Survivin antagonists developed for clinical testing include an antisense molecule (LY218130B), and transcriptional repressors (YM155 and EM1421).[23,24] Tolcher et al. completed a Phase I study of YM155 in patients with advanced solid malignancies or lymphoma. In this study, Forty-one patients received this small molecule inhibitor of survivin at doses ranging from 1.8-6.0 mg/m2/day for 168-h CIVI every 3 weeks. Overall the most common grade 1-2 toxicities were stomatitis, pyrexia, and nausea, whereas grade 3 and 4 toxicities were rare. The dose limiting toxicity was reversible renal insufficiency at 6.0 mg/m2. There was no myelosupression observed. Responses were seen in three patients with Non-Hodgkin's lymphoma, two patients with refractory prostate cancer and one patient with non-small cell lung cancer.[25]

Survivin is a good candidate for immunotherapy due to its key role in cancer survival and the fact that is over expressed in cancer tissues but not in most normal tissues. However, the fact that survivin is expressed in CD 34 hematopoietic stem cells raised concerns about potential toxicity when used clinically. Nagaraj et al[26] evaluated this risk by using dendritic cells transduced with an adenovirus encoding mutant human survivin in preclinical studies. Immunization of mice with this vaccine resulted in generation of CD8 Tells recognizing multiple epitopes from mouse survivin and these responses provided significant antitumor effect against EL-4 lymphoma, MC-38 carcinoma, and MethA sarcoma. No effects on the bone marrow hematopoietic progenitor cells were observed suggesting that this is a safe and clinically feasible approach to target survivin. Other investigators have also tested the efficacy of targeting survivin with a DNA vaccine given to mice with NSCLC.[27] This vaccine encoded survivin and a chemokine known to be overexpressed in the tumor blood vessels. The vaccine elicited an effective CD8 T cell response against survivin and this resulted in eradication of pulmonary metastasis of NSCLC in mice.

The first survivin vaccine tested in the clinic was generated from autologous dendritic cells (DCs) and tested in patients with non-small cell lung cancer (NSCLC) by Hirschowitz et al.[28] In this study, 16 patients with NSCLC were treated with autologous DC vaccines generated from CD 14+ precursors, pulsed with apoptotic bodies of an allogeneic NSCLS cell line that over expressed survivin. The patients were immunized intra-dermally 2 times, 1 month apart after they received initial cytoreductive therapy in the form of surgery, chemoradiation, or both. Peripheral blood was drawn serially after vaccination and immune responses measured by interferon-gamma ELISPOT. There were no unanticipated adverse events and six of 16 patients showed antigen specific responses. This study suggests that this vaccine approach is well tolerated and has biologic activity in this patient population.

Additional strategies targeting survivin using restricted peptide vaccines have demonstrated CD8 and CD4 immune responses without significant toxicities.[29-31]

Despite high expectations, immunotherapy clinical trials performed in recent years demonstrated very limited clinical efficacy.[32] It appears that cancer immunotherapy is faced with a number of challenges. They include the ability of vaccination to generate potent immune responses given the presence of numerous immunosuppressive factors, the ability of cytotoxic T cells to penetrate tumor parenchyma and recognize tumor-associated antigen, and the correct choice of antigen for immunization. It has become apparent that therapeutic cancer vaccines given as a single agent will not likely produce substantial clinical benefits. An emerging strategy is one whereby multiple pathways of tumor cell survival and drug resistance are targeted by using immunotherapy in combination with chemotherapy or radiation therapy.[33,34]

High dose chemotherapy with subsequent stem cell transplantation may represent a therapeutic strategy, termed immunotransplant, can abrogate negative effect of various immunosuppressive mechanisms. This approach can dramatically reduce tumor burden and eliminate immunosuppressive regulatory cells. If combined with vaccination it can induce cytotoxic T cells against specific antigens in the malignant cells and exploit the homeostatic T cell repopulation after high dose chemotherapy, resulting in enhanced T cell expansion and producing a robust, therapeutic immune response against myeloma. Using a murine model, Brody et al. demonstrated that vaccination prior to hematopoietic cell collection elicits strong post-transplant CD4+ and CD8+ responses which were potentiated by additional vaccination given immediately post-transplant.[35]

For myeloma patients, this concept has been tested by Rapoport et al., who combined vaccination, adoptive T cell transfer, and high-dose chemotherapy and autologous hematopoietic stem cell transplantation for patients with myeloma. In their studies, primed T cells were collected after immunization, expanded ex vivo with anti-CD3 and CD28 antibodies coated beads, and re-infused just after high dose melphalan chemotherapy and ASCT. Vaccine boosts administered soon after the T cell transfer lead to significantly higher antibody responses than vaccine boosts in patients who had not had T cell transfer. T cell transfer resulted in accelerated restoration of CD4 T cell function and allowed vaccine specific immunity in just one month following autologous SCT.[36] In their studies, stem cells were collected from peripheral blood after mobilization with cyclophosphamide, a treatment that yields few T cells in the graft.

Rapoport reported that an HLA-A2 restricted combined peptide vaccination, consisting of the survivin Sur1M2 peptide (LMLGEFLKL) and 3 hTERT peptides, could elicit an immune response in the context of autologous transplant for myeloma. In that trial 28 myeloma patients were vaccinated prior to collection of T cells by pheresis. These cells were then stimulated and expanded ex vivo. Patients then had stem cells collected from peripheral blood after mobilization with cyclophosphamide, a treatment that yields few T cells in the graft. The vaccine primed and ex vivo expanded T cells were then re-introduced into the patient during the lymphopenic period after high dose melphalan chemotherapy and transplant. Patients were then re-vaccinated after transplant to potentiate that immune response. Although patients were not stratified by tumor associated antigen expression, it was demonstrated that adoptive transfer of vaccine-primed and co-stimulated T cells increased cellular antitumor immune reconstitution, in the post-transplant setting. Reactions to the peptide vaccines were acceptable with reactions limited to muscle aches, redness, and induration at the injection site.

Despite the effectiveness of this approach at safely eliciting immune responses against tumor, an approach which does not require ex vivo T cell priming, expansion and manipulation might be preferable. Furthermore, a strategy which does not require a specific HLA type, and selects patients based upon survivin expression will maximize the patients eligible for therapy while excluding those less likely to benefit.[37]

Example 9—a Unique Immunotransplant Vaccination Schedule Induces Strong Humoral and Cellular Immune Responses for Myeloma Patients None of the previously mentioned human ASCT trials coupled immunization just before standard G-CSF primed unfractionated hematopoietic cell collection with immunization again early post-transplant, during the period of homeostatic proliferation.

The inventors hypothesized that immune responses could be generated by vaccination and immunotransplant without ex vivo T cell expansion, such as done by Rapoport. To test this, the inventors conducted a feasibility and biological activity study of Prevnar-13 (PCV-13), a pneumococcal 13-valent conjugate [diphtheria CRM197 protein] vaccination, before G-CSF mobilization and hematopoietic cell collection. Patients were again vaccinated during the lymphopenic period, 21 days after transplant. Biological endpoints of this study included antibody responses against pneumococcal serotypes and T cell responses against CRM197.

Prevnar-13 was well tolerated. IgG against vaccine-specific serotypes was significantly increased [Geometric mean IgG=0.45 (95% CI=0.33-0.66) pre- to 4.12 (95% CI=2.7-6.2) post-vaccine; p<0.001]. IgG against pneumococcal serotypes not included in the vaccine did not increase (FIGS. 13A-13B). Six of 11 vaccine-specific serotypes IgG tested were significantly increased after transplant (p<0.05) (data not shown).

Vaccination met the primary endpoint by eliciting CD4+ and CD8+ cell division and expression of intracellular IFN-gamma in response to CRM197, the Prevnar-13 adjuvant (p<0.05) (FIGS. 14A-14B). CD8+ cells had a significant increase of the cytotoxicity marker CD107a (p<0.05) (FIGS. 14C-14D).

Prevnar-13 vaccination before and 21 days after autologous transplant is safe and elicits specific antibodies, CD4+ helper, and CD8+ cytotoxic responses against pneumococcal serotypes and CRM197 adjuvant in myeloma patients. Vaccination against myeloma-associated antigens should be tested before and 21 days after auto-transplant.

Thus, combination of high-dose chemotherapy with HCT and cancer vaccines is feasible and may result in potent immune response.

For a vaccine to be efficacious, it must present tumor-specific antigens whose presence is vital for the survival of the neoplastic cell and must activate immune responses and, if necessary, overcome the state of immune tolerance associated with cancer.[32]

Human cancer cells express protein antigens that can be recognized by T cells and are not expressed in normal tissues, thus providing potential specific targets for cancer immunotherapy. Dendritic cells (DC) are the most potent known antigen-presenting cells and are essential for initiation of T cell mediated immunity; this property has prompted their recent application to therapeutic cancer vaccines. DCs express co-stimulatory molecules such as CD40, CD80, and CD86, among others, that are essential to activation of primary cellular immune responses. In this trial the inventors will utilize monocytes-derived myeloid dendritic cells to present survivin.

Survivin is a highly attractive target for cancer immunotherapy because it is essential for cancer cell survival[17] and drug resistance,[12,13] and it is over-expressed by tumors but not most normal adult cell. Overexpression of survivin results in increased expression of survivin-derived epitopes on the tumor cell surface. These epitopes in association with MHC class I molecules, represent targets for cytotoxic T cells (CTL). Previous studies have demonstrated the generation of survivin-specific CTL responses in vitro in cancer patients and in vivo in tumor-bearing mice.[38,39] One of the most effective methods to generate potent survivin-specific responses is a vaccine that utilizes dendritic cells (DC) transduced with full-length mutant survivin[40]. The use of mutant survivin eliminates the potential problem of delivering an anti-apoptotic activity associated with wild-type survivin to patients. The overexpression of full-length survivin in DCs allows for the presentation of multiple different epitopes. Finally, the use of an adenovirus backbone provides for high efficiency of DC transduction, and results in DC activation, two aspects that are crucial for the success of cancer immunotherapy.

Example 10—Immunotransplant Strategy for Vaccination Against Survivin for Myeloma Patients Survivin is an ideal myeloma tumor associated antigen
    High survivin expression is linked to progressive and refractory myeloma
    Survivin is expressed in a significant proportion of our patients
    Myeloma patients have T cells against survivin
The full length double mutant survivin vaccine was developed
    This vaccine leads to immune responses against tumors in animal models
    This vaccine leads to T cell responses against survivin in myeloma patient samples, even when there are very few survivin specific T cells
    This removes the need for HLA matching required with peptide based vaccines,
    This allows for T cells specific for numerous epitopes to be generated.
    The mutated form of survivin decreases any potential for toxicity without compromising immune responses
Numerous others have tested survivin peptide vaccines and survivin antagonists without significant toxicity, here the inventors will test the safety and biological activity of their novel approach to target survivin.

Novel schedule of vaccination and immunotransplant results in robust immune responses using a pneumonia vaccine Using the same schedule should result in robust immune responses against survivin Ex vivo manipulation of the transferred T cells is not required and our strategy of G-CSF mobilized collection of both T cells and hematopoietic stem cells allows for a more physiologic development of T cells within the patient.

This is important as the repertoire of naive to central memory to effector memory subsets is known to play a key role in the efficacy following adoptive transfer The inventors propose a novel strategy, combining the double mutant survivin-dendritic cell vaccine with high-dose-chemotherapy and autologous hematopoietic cell transplantation. Immunization of patients prior to stem cell mobilization should result in accumulation of survivin-specific T cells in vivo, that will be collected and transferred as part of HCT.

The inventors propose that this strategy combined with post-HCT survivin-dendritic cell vaccination boost will be safe and induce immune responses against survivin in myeloma patients.

Example 11—Determination of Whether Immune Responses are Induced by Survivin Vaccination in Patients with Myeloma Before and After Autologous HCT To pursue this aim, MM patients with high survivin expression will receive survivin vaccine prior to stem cell mobilization and collection, and again after autologous HCT. The hypothesize that immunization of patients to survivin before stem cell collection will prime T cells against survivin, and allow for collection of those T cells along with the stem cells. T cells that are infused with the graft will augment the immune response against myeloma, exploiting the homeostatic repopulation process that occurs after high dose therapy. Immune response to survivin will be measured by IFN-gamma ELISPOT and by limiting dilution precursor frequency analysis (proliferation). The inventors will also evaluate immune responses to other tumor-associated antigens and evaluate the immune response after the start of lenalidomide post-transplant maintenance therapy.

Survivin is undetectable in most adult tissues, except for low level expression in thymocytes, resting, activated and memory T cells, hematopoietic progenitor cells, and colonic epithelial cells. Other investigators have safely immunized against survivin peptide sequences in the setting of autologous transplant, however the inventors will monitor for unforeseen toxicities in survivin-expressing tissues. In this aim the inventors will determine the full toxicity profile for full length dendritic cell based survivin vaccination in myeloma patients. The inventors will closely monitor time and persistence of hematopoietic engraftment, T cell reconstitution, toxicity in the gastrointestinal system, and any other organ toxicity. The inventors will conduct a single arm feasibility study of 10 patients to evaluate clinical efficacy of this intervention.

Inclusion Criteria for Screening Phase

Patients with histologically confirmed Multiple Myeloma (see Appendix III) that are potentially eligible for high dose chemotherapy and autologous stem cell transplant in the future. Patients must have a bone marrow biopsy available, or one scheduled to be performed for a clinical indication. (Patients that have been treated with an induction regimen are eligible for this phase of study)

Inclusion Criteria for Treatment Phase

Patients enrolled in screening phase of study

Patients are planned for treatment with high dose melphalan and autologous HCT.

CBC with an absolute neutrophil count (ANC)≥1,000/uL, hemoglobin ≥8.0 g/dL and platelet count ≥50,000/uL.

Liver enzymes: total bilirubin less than or equal to 2 mg/dL (>2 mg/dL permitted if the patient has Gilbert's disease); AST and ALT less than 1.5× the upper limit of normal.

Exclusion Criteria for Treatment Phase

Patients with CR or stringent CR after induction therapy as defined by International Response Criteria after most recent therapy.

Patients with progressive disease at time of transplant

Pregnant or lactating woman (as evaluated by serum testing within 48 hours of administration of the first vaccine in women of child bearing potential HIV Infection Confirmed by NAT Common variable immunodeficiency Active CNS malignancy Active bacterial, fungal or viral infection Prior history of allogeneic hematopoietic cell transplantation Prior malignancy within 5 years of enrollment excluding non-melanoma skin cancer or cervical carcinoma after curative resection, not requiring chemotherapy.

History of severe allergy (e.g., anaphylaxis) to any component of Prevnar or any diphtheria-toxoid containing vaccine Enrollment Procedure Patients will be identified as potential study candidates at initial diagnosis, while receiving induction therapy, or at the time of transplant consultation. Potential trial patients will be approached, provided an explanation of the trial, and given a copy of the informed consent.

If the patient meets the criteria for the screening phase and decides to participate he/she will be asked to sign the informed consent document and enrolled in the screening phase of the study. Next a bone marrow biopsy specimen will be obtained (prior collected specimens, if obtainable, are permitted) to determine survivin expression by immunohistochemistry.

If the patient's marrow plasma cells express survivin, then this information will be shared with them by the research team. Inclusion criteria for the treatment phase will be reviewed before proceeding to the treatment phase.

Treatment Plan

Patients will receive 1 pre-transplant survivin vaccine, 7-30 days prior to stem cell apheresis collection. A second survivin vaccine will be administered on day +21 (between day +20 and +34) after HCT.

Generation of survivin vaccine

Mononuclear cells for the production of myeloid dendritic cells (DC) will be obtained through a single apheresis procedure and stored in liquid nitrogen at least 21 days after completion of induction therapy. After collection through apheresis, mononuclear cells will be cryopreserved. Just before patients are due for vaccination, cells will be thawed and placed in X-VIVO-15 medium (Biowhittaker, Walkersville, MD) in tissue culture flasks at a concentration of 1.3 to $1.7 \times 10^6$ cells/mL. After culturing for 2 hours, non-adherent cells will be removed and the flasks will be recharged with X-VIVO-15 medium supplemented with 5 ng/ml GM-CSF and 5 ng/ml of interleukin-4 (R&D systems, Minneapolis, MN, USA) and incubated for 48 hours. Thereafter, additional cytokine-supplemented medium will be added to the flasks and incubated for additional 72 hours. At the completion of incubation, the non-adherent and loosely adherent cells will be collected and used for a 2 hour infection with Ad-survivin at an optimal ratio of 15,000:1 viral particle to cell ratio. The optimal ratio to produce the highest level of survivin expression with the least amount of toxicity to dendritic cells was determined in preliminary experiments by our group and on file with the FDA. At the end of the 2-hour incubation, X-VIVO medium will be added to a final concentration of $1 \times 10^6$ cells/mL, and cells will be incubated in the flasks for an additional 46 hours, at which time the cells will be harvested, washed and analyzed.

Release Criteria: in order to release the vaccine for clinical use several criteria must be met including:

A negative Gram's staining;

An endotoxin concentration no greater than 5 EU/ml;

A mature DC phenotype and evidence of intracellular survivin expression by western blot or flow cytometry analysis.

Pre-Transplant Vaccination

At a time not greater than 30 days (and not less than 7 days) from planned stem cell apheresis collection, vaccine will be administered by intradermal injection at a site that drains to the axillary and/or inguinal lymph node basins. Patients will receive premedication with diphenhydramine. Acetaminophen may be used also as pre-medication. Steroids as a pre-treatment should be avoided.

Stem Cell Mobilization and Collection

Patients will undergo stem cell mobilization with G-CSF (granulocyte colony-stimulating factor) per institutional protocol. Plerixafor use is permitted and is at the discretion of the treating physician. A minimum of $4 \times 10^6$ CD34+ peripheral blood stem cells per kilogram of recipient's body weight must be collected prior to proceeding to autologous stem cell transplant. All patients will have at least $2 \times 10^6$ CD 34+ cells stored after transplantation. The stem cells from autologous patients will be cryopreserved and stored in Cell Core Facility until the day of transplant.

Post-Transplant Vaccination

On or between day +20 to +34 after stem cell infusion the post-transplant survivin-DC vaccine will be administered by intradermal injection at separate sites that drain to the axillary and inguinal lymph node basins. Patients will receive premedication with diphenhydramine. Acetaminophen may be used also as pre-medication. Steroids will be avoided.

Co-Immunization with 13-Valent Pneumococcal Conjugate Vaccine (PCV13, Prevnar13)

All patients will be co-immunized with Prevnar at each time they receive the survivin vaccine. This vaccine will be administered IM (0.5 cc). Since Prevnar is a T cell dependent vaccine for *Streptoccocus pneumonia*, evaluation of anti-pneumococcal immune response will serve as a positive control for a vaccine immune response. In addition Prevnar includes the CRM protein as an adjuvant and T cells responses against this adjuvant can be tested directly.

Vaccination Administration

Deferral of vaccination until resolution of the offending event will occur in the following instances:

Platelet count <20,000/microliter at the time of ID injection (survivin vaccine), or <50,000/microliter at the time of IM injection (Prevnar). These may be obtained with platelet transfusions.

The patient is febrile.

The patient is septic or is on ventilatory or vasopressor support.

Patient Monitoring for injection reaction: Vital signs will be checked prior to administration of vaccine, and 60 minutes after administration. 60 minutes after injection, the site will be examined for local reaction.

Suspension of Treatment

Patients will be removed from the treatment phase of the study for the following reasons (note that patients having already received one or more vaccine will remain on the protocol for safety evaluation):

Progressive Disease as Defined in Appendix I

Patients having serious anaphylactic/anaphylactoid reactions to the vaccination.

Patients having any serious or life-threatening reactions to any of the study treatments such that, in the opinion of the investigators, continuation in the study is not in the best interest of the patient Patients unable to harvest sufficient monocyte dendritic cell precursors to generate enough vaccines for 3 doses ability to administer the vaccine due to microbial contamination or other safety concerns Non-compliance Ineligibility for HCT Failure to collect sufficient stem cells for HCT (at least 4 million/kg BW)

Clinical and Laboratory Evaluations

Survivin Immunohistochemistry.

The tissues will be stained for Survivin, using a rabbit polyclonal antibody (Novus Biologicals, Inc.), per institutional and manufacturers protocol. The specificity of the anti-Survivin polyclonal antibody will be confirmed by using survivin over-expressing and survivin absent cell lines or tissues. Negative controls will be included by omitting survivin antibody during the primary antibody incubation step.

Immunohistochemical Data Analysis.

The Survivin stained tissues will be examined by an expert pathologist (Dr. Coppola). The positive reaction of Survivin will be scored into four grades, according to the intensity of the staining: 0, 1+, 2+, and 3+. The percentages of Survivin positive cells will also be scored into five categories: 0 (<5%), 1 (5-25%), 2 (26-50%), 3 (51-75%), and 4 (76-100%). The product of the intensity by percentage scores will be used as the final score. A product score ≤1 will be considered negative. Survivin is expressed in about 40% of myeloma patients.

Initial Study Evaluation after Induction Therapy for Myeloma

Eligibility to proceed with high dose chemotherapy and autologous HCT will be per institutional guidelines. This evaluation will be obtained within 30 days of pheresis to collect PBMC, and will be conducted per Moffitt Institutional Guidelines.

Post-transplant evaluation at day +60 ((+/−15 days), day +90 (+/−15 days), and day +180 (+/−20 days)
- Comprehensive history and physical examination (including performance status, height, weight)
- CBC with differential
- Serum biochemical screening profile (to include BUN, Serum creatinine, glucose, uric acid, sodium, potassium, total calcium, magnesium, bilirubin, total protein, albumin, alkaline phosphatase, AST, ALT, GGT, LDH).
- SPEP, UPEP, Serum free light chains, Quantitative Immunoglobulins
- Bone marrow aspiration and biopsy with cytogenetics and myeloma FISH panel (only if necessary to confirm complete remission)
- Bone survey for patients with pre-transplant bony disease (to be done at day +90 (+/−15 days))

Disease Status Evaluations
- Disease status will be evaluated at day +90 (+/−15 days), day +180 (+/−20 days), according to International Response Criteria
- Pre and post vaccinations immune response evaluations
- Immunologic responses will be measured at baseline prior to the first vaccination, after stem cell mobilization and collection, and post-transplant at day +60, +90, and +180. At each time 50 cc of peripheral blood will be collected from the patients in a heparinized tube. Immune response evaluations will consist of the following:
  - Analysis of Interferon-gamma producing T cells in ELISPOT assays in response to the DC with survivin peptide pool. The definition of a positive response will be a post-vaccination result that is higher than the pre-vaccination values AND values in cells stimulated with unloaded DCs by at least 2 times the standard deviation AND with a value of at least 10 spots per 100,000.
  - Measurement of anti-pneumoccocal IgG antibody titers and T cell responses against CRM adjuvant will be done before the first vaccine, and at day +60, +90, and +180 after transplantation.
  - Determination of the survivin specific T cell frequency using limiting dilution analysis and freely available online software. Specifically the percentage of each patient's CD4+ and CD8+ T cells which are reactive against a survivin peptide pool will be calculated at each time (baseline, day +60, +90, and +180).
  - Evaluation of immunomodulatory phenotypes by T cell subsets before and after vaccination. Patient PBMCs collected both at baseline, at the time of stem cell collection (after vaccination), and each follow-up will be stained and evaluated by flow cytometry. PD-1 expression on T cells, and PD-L1 expression in the tumor microenvironment, can predict for response to immunomodulatory drugs such as anti-PD-L 1. Peripheral blood CD4 and CD8 T cells and DCs, as well as bone marrow aspirate collected before treatment, will be stained for CD279+(PD-1); CD152+ (CTLA-4); and DCs for B7-H1 (PD-L1). A second experiment will test patient T cells co-incubated with self-DCs+Ad-mS with or without blocking antibodies against these targets (anti-PD1, anti-PD-L1, and anti-CTLA-4). T cells will be separated after 7 days and INF-gamma ELISPOT responses against survivin will determine if promising targets might be pursued.

Determination of Safety.
- Our approach for assessing potential toxicity of survivin vaccination will focus predominantly on assessing hematopoietic reconstitution, including T cell repopulation and gastrointestinal toxicity. The inventors will also monitor for autoimmune disorders involving other tissues where survivin expression has been demonstrated: these include keratinocytes and melanocytes, myocardium, liver, breast, and brain. It might not be possible to assess toxicity on uterus, ovary, and testes as these are compromised by high dose Melphalan and other cytotoxic therapies for the myeloma.

Clinical Followup
- Patients will follow up with a clinical trials coordinator and/or physician to evaluate for any acute or sub-acute toxicity according to standard of care. This includes daily assessment until neutrophil engraftment. In the absence of any complications, patients will then be followed as an outpatient at day +60 (+/−15 days), and day +90 (+/−15 days) after transplant, with the final determination of response at 6 months made at +180 (+/−20 days) days after transplant.

Toxicity Scoring
- Toxicity will be scored according to the NCI Common Toxicity Criteria 4.0 (http://ctep.cancer.gov/reporting/ctc.html) grading scale. Significant adverse events will only be scored if unexpected with melphalan based autologous transplantation (see section 7.3 and Appendix II). CTC toxicity will be assessed on +60 ((+/−15 days), +90 (+/−15 days), day +180 (+/−20 days) and results will be tabulated. Assessment of potential association of toxicity with survivin vaccination will be possible if more than one patient develops similar constellation of symptoms.

Hematopoietic Stem Cells.
- Our data in mice and clinical data from others using survivin antagonists or vaccines showed that targeting survivin did not affect hematopoietic progenitor cells. The most sensitive test to assess the potential toxicity of survivin vaccination on hematopoietic function is the time of neutrophil repopulation after HCT. Beginning on the day of HCT, patients will be monitored daily for engraftment, that is defined by an absolute neutrophil count of 500 cells per microliter that is sustained for at least 3 days. The rate of failure of neutrophil engraftment by day +21 in this population is estimated as <1%, with the longest time to neutrophil engraftment in the last 100 patients treated at the Moffitt Cancer Center being 19 days.
- After engraftment, the inventors will monitor absolute neutrophils and platelet counts, and hemoglobin at least once quarterly through one year, and assessment of hematological toxicities will be done using the NCI Common Toxicity Criteria 3.0 grading scale.
- In absence of cytotoxic therapy, grade 4 toxicity (graft loss) would be unexpected. Thus, if one patient fails to engraft by day +21, or experiences unexplained graft loss between day +21 and +180, the study will be suspended pending data review by the Protocol Monitoring Committee (PMC) at the Moffitt Cancer Center. Upon review, the PMC may re-activate the study, possibly after protocol revision of the treatment plan or patient eligibility criteria. If the study is re-activated, a second failure to engraft or a second case of unexplained graft loss will result in automatic termination of the study (see section 7.3 for stopping rules).

Any case with grade 4 hematopoietic toxicity would be evaluated and treated with supportive therapy including antibiotics, transfusions and growth factors if clinically indicated. Cases meeting criteria for severe aplastic anemia would be treated as such, employing state-of-the-art immune suppressive regimens. In absence of recovery, reinfusion of cryopreserved autologous cells would occur. For this purpose, all patients in the treatment phase of study will be required to mobilize and collect at least 4 million CD34+ cells/kg, thereby allowing to store at least 2 million CD34+ cells in case a second stem cell infusion is required.

T Cell Reconstitution

Since survivin is expressed in thymocytes and replicating T cells, the inventors will monitor T cell reconstitution after transplant by measuring CD4+ and CD8+ T cells on +90 (+/−15 days) and day +180 (+/−20 days) after transplantation in all patients who received survivin vaccine. As there are no definitive published control data after autologous transplantation for myeloma, the results will be tabulated.

Grade 4 CTC defined toxicity for CD4 lymphopenia, i.e. below 50 cells per microliter at either time point would be unexpected and considered as a possible toxicity, taking into account any post-transplant therapy outside the scope of this trial, which may have occurred.

Patients will receive appropriate antibiotic prophylaxis for opportunistic infections, as recommended by the CDC at time of study. The inventors will record the rate of infections in the first year after transplant, with this data being collected at the time of quarterly post transplant follow-up.

Reporting Serious/Unexpected Adverse Events:

Definitions

Serious adverse events (SAE): are defined as those that are fatal, life threatening require inpatient hospitalization or prolongation of existing hospitalization, results in persistent or significant disability/incapacity, or is a congenital anomaly/birth defect. SAEs will be identified by the investigators or BMT study coordinator and will be reported to the IRB and PMC according to current institutional policy.

Based upon published data for the melphalan conditioning regimen without vaccination[41], the following toxicities occur at a high rate which should be taken into consideration when reporting SAEs (incidence of grade 3-4 in parenthesis):

Any hematologic toxicity (>77%)
The use of intravenous antibiotics (41%)
Mucositis (17%)
Diarrhea (5%)
Nausea or vomiting (6%)
Infection (40%)
Hospitalization after engraftment (48%)

Unexpected adverse events: include those events not identified in their nature, severity, or frequency in the published blood and marrow transplant literature or those not included in the "Risks" section of the informed consent. These events will be identified by the investigators or BMT Research Staff and will be reported to the IRB and PMC according to current policy.

Exceptions

Exceptions to the reporting will be the following commonly anticipated events:

Hospitalizations post mobilization or post transplant for neutropenic or non-neutropenic fevers
Hospitalizations for non-life-threatening events
Hospitalizations for chemotherapy or radiation therapy (or its complications) used for the treatment of progressive disease
Extended outpatient (EOP) admissions or 23 hour observation admissions
Relapse-related deaths
Hospitalizations after relapse of primary disease Statistical Considerations Primary Endpoint and Sample Size Determination Screening Phase of Study Consenting patients with MM will be screened for survivin expression in myeloma cells by IHC of a bone marrow biopsy performed at any time. All cases will be reviewed and scored for MM survivin expression using the Allred score.[42] Survivin-positive patients (Allred score >=2) are eligible, and our preliminary data indicate this accounts for about 40% of patients at the time of AHCT (18/48 patients, data not shown). Only patients that failed to achieve a CR prior to transplant are eligible. Otherwise standard institutional criteria for autologous transplant will serve as eligibility criteria. Conservatively, the inventors anticipate the need to screen 100 patients of which 40 would be survivin positive and 10 (25%) would be eligible and consent to treatment. The inventors perform about 140 AHCT/year for MM, 70 (50%) of which are in CR at transplant, so the inventors should be able to screen 100 patients in ~1.5 years. Accrual and completion of treatment (n=10) is expected in 2.5 years Biological Endpoint and Treatment Phase Sample Size Determination The inventors propose this treatment will increase the frequency (%) of circulating survivin reactive CD4+ T cells (see Interpretation of immune response). Comparison of the pre-vaccine frequency to the post-transplant (day +60) frequency will serve as the primary endpoint.

The inventors hypothesize that survivin vaccination will increase the survivin reactive CD4+ cell frequency at day +60 compared to baseline in greater than 55% of patients. If the true response rate is <=20%, the inventors will conclude that this approach is ineffective at generating T cell responses with a probability of at least 90% (alpha=0.10). If the true response rate is >=55%, the inventors will conclude that the therapy is effective at generating T cell responses with a probability of at least 90% (beta=0.90). To reject the null hypothesis, that the response rate <=20%, the inventors will need at least 4 (of 10) patients to mount an effective IFN-gamma ELISPOT response over baseline.

This Design has the Following Two Properties:

The choice of a one-sided study with alpha=0.10 is quite common in early phase trials, as it increases the probability of not missing a potentially useful therapy. The choice of beta=0.10 is frequently recommended by CTEP statisticians, as it increases the probability that potentially useful therapies will not be deemed ineffective.

Expected Length of the Study

Approximately 140 autologous transplants for myeloma are conducted at Moffitt Cancer Center per year. The inventors estimate that 42 patients per year (30%) will agree to participate in the screening phase. To enroll the anticipated 63 patients to the screening phase the inventors estimate it will take 18 months. Including the 6 month followup the inventors anticipate the length of time it will take to complete the study will be 2 years.

Stopping Rules for Toxicities (Safety)

The most sensitive test to assess the potential toxicity of survivin vaccination on hematopoietic function is the time of neutrophil repopulation after ASCT. Beginning on the day of ASCT, patients will be monitored daily for engraftment, which is defined by an absolute neutrophil count of 500 cells per microliter that is sustained for at least 3 days. The rate of failure of neutrophil engraftment by day +21 in this population is estimated as <1%, with the longest time to neutrophil engraftment in the last 100 patients treated at the Moffitt Cancer Center being 19 days. Thus, if one patient fails to engraft by day +21, or experience unexplained graft loss between day +21 and +180, the study will be suspended pending data review.

The inventors will also perform CD34 viability assays in the cells harvested for transplantation prior to starting high dose chemotherapy. Assessment of potential association of toxicity with survivin vaccination will be possible if more than one patient develops similar constellation of symptoms. Careful assessment and monitoring of other toxicities will be done using the NCI Common Toxicity Criteria 4.0 (http://ctep.cancer.gov/reporting/ctc.html) grading scale.

Data Management:

Data related to the immunologic parameters such as doses of vaccination, clinical and immunologic responses to vaccination will be entered into the immunology database at the H. Lee Moffitt Cancer Center and will also be kept confidential. In computer-generated reports for external review, patients will only be referred to by a unique identification number. The BMT and immunology research databases are password protected and limited only to designated personnel.

Representatives of the USF IRB, the FDA, and other governmental regulatory authorities will have access to patient information as it pertains to the study. Privacy and confidentiality of the information will be protected to the extent provided by law.

Ethical and Regulatory Considerations

Informed consent: all patients will be required to sign a statement of informed consent that has been approved by the local Institutional Review Board. The principal investigator or designated co-investigator (during absence of PI) is responsible for verifying compliance with all aspects of both the protocol and the informed consent process, which must indicate that the patient has received adequate information to make such informed consent.

Women and minorities: The inventors will assure that the participation of women and minority subjects will reflect the percentage representation of these populations in our region. This study will not discriminate against any subgroup of patients. All eligible patients will be offered participation in this study.

Data and Safety Monitoring Plan

The principal investigator will have the primary responsibility for data safety and monitoring. Input will be sought from sub investigators and other members of the BMT and Thoracic Oncology Program concerning data and safety issues. The Moffitt Cancer Center Protocol Monitoring Committee (PMC) will provide oversight for monitoring. The PMC meets monthly and reviews accrual, patterns and frequencies of severe or unexpected adverse events as defined in the protocol, protocol violations and, when applicable, internal audit results.

References for Examples 6-11

1. American Cancer Society, 2007. (Accessed at www.cancer.org/.)
2. Barlogie B, Shaughnessy J, Tricot G, et al. Treatment of multiple myeloma. Blood 2004; 103:20-32.
3. Attal M, Harousseau J L. Randomized trial experience of the Intergroupe Francophone du Myelome. Semin Hematol 2001; 38:226-30.
4. Palumbo A, Miguel J S, Sonneveld P, et al. Lenalidomide: a new therapy for multiple myeloma. Cancer Treat Rev 2008; 34:283-91.
5. Rawstron A C. Minimal residual disease detection in myeloma: no more molecular remissions? Haematologica 2005; 90:1300B.
6. Richardson P G, Mitsiades C, Schlossman R, et al. Bortezomib in the front-line treatment of multiple myeloma. Expert Rev Anticancer Ther 2008; 8:1053-72.
7. Nakagawa Y, Abe S, Kurata M, et al. IAP family protein expression correlates with poor outcome of multiple myeloma patients in association with chemotherapy-induced overexpression of multidrug resistance genes. Am J Hematol 2006; 81:824-31.
8. Altieri D C. Survivin, versatile modulation of cell division and apoptosis in cancer. Oncogene 2003; 22:8581-9.
9. Knauer S K, Mann W, Stauber R H. Survivin's dual role: an export's view. Cell Cycle 2007; 6:518-21.
10. Li F, Ambrosini G, Chu E Y, et al. Control of apoptosis and mitotic spindle checkpoint by survivin. Nature 1998; 396:580-4.
11. Stauber R H, Mann W, Knauer S K. Nuclear and cytoplasmic survivin: molecular mechanism, prognostic, and therapeutic potential. Cancer Res 2007; 67:5999-6002.
12. Ambrosini G, Adida C, Altieri D C. A novel anti-apoptosis gene, survivin, expressed in cancer and lymphoma. Nat Med 1997; 3:917-21.
13. Cong X L, Han Z C. Survivin and leukemia. Int J Hematol 2004; 80:232-8.
14. Fields A C, Cotsonis G, Sexton D, Santoianni R, Cohen C. Survivin expression in hepatocellular carcinoma: correlation with proliferation, prognostic parameters, and outcome. Mod Pathol 2004; 17:1378-85.
15. Kawasaki H, Altieri D C, Lu C D, Toyoda M, Tenjo T, Tanigawa N. Inhibition of apoptosis by survivin predicts shorter survival rates in colorectal cancer. Cancer Res 1998; 58:5071-4.
16. Mori A, Wada H, Nishimura Y, Okamoto T, Takemoto Y, Kakishita E. Expression of the antiapoptosis gene survivin in human leukemia. Int J Hematol 2002; 75:161-5.
17. Andersen M H, Svane I M, Becker J C, Straten P T. The universal character of the tumor-associated antigen survivin. Clin Cancer Res 2007; 13:5991-4.
18. Li J, Zhao Y, Zhang D B, Huang B H. [Expression and clinical significance of survivin in bone marrow cells of multiple myeloma patients]. Ai Zheng 2005; 24:1522-6.
19. Romagnoli M, Trichet V, David C, et al. Significant impact of survivin on myeloma cell growth. Leukemia 2007; 21:1070-8.
20. Grube M, Moritz S, Obermann E C, et al. CD8+ T cells reactive to survivin antigen in patients with multiple myeloma. Clin Cancer Res 2007; 13:1053-60.

21. Gerdemann U, Keirnan J M, Katari U L, et al. Rapidly generated multivirus-specific cytotoxic T lymphocytes for the prophylaxis and treatment of viral infections. Mol Ther 2012; 20:1622-32.
22. Ramos C A, Narala N, Vyas G M, et al. Human papillomavirus type 16 E6/E7-specific cytotoxic T lymphocytes for adoptive immunotherapy of HPV-associated malignancies. J Immunother 2013; 36:66-76.
23. Chang C C, Heller J D, Kuo J, Huang R C. Tetra-O-methyl nordihydroguaiaretic acid induces growth arrest and cellular apoptosis by inhibiting Cdc2 and survivin expression. Proceedings of the National Academy of Sciences of the United States of America 2004; 101: 13239-44.
24. Nakahara T, Takeuchi M, Kinoyama I, et al. YM155, a novel small-molecule survivin suppressant, induces regression of established human hormone-refractory prostate tumor xenografts. Cancer research 2007; 67:8014-21.
25. Tolcher A W, Mita, Alain, Lewis, Lionel D., Garrett, Christopher, Till, Elizabeth, Daud, Adil, Patnaik, Amita, Papadopoulos, Kyri, Takimoto, Chris, Bartels, Pamela, Keating, Anne, Antonia, Scott. A Phase I and Pharmacokinetic Study of YM155, A Small Molecule Inhibitor of Survivin. In: Journal of Clinical Oncology; 2008.
26. Nagaraj S, Pisarev V, Kinarsky L, et al. Dendritic cell-based full-length survivin vaccine in treatment of experimental tumors. J Immunother 2007; 30:169-79.
27. Hirschowitz E A, Foody T, Kryscio R, Dickson L, Sturgill J, Yannelli J. Autologous dendritic cell vaccines for non-small-cell lung cancer. J Clin Oncol 2004; 22:2808-15.
28. Hirschowitz E A, Foody T, Hidalgo G E, Yannelli J R. Immunization of NSCLC patients with antigen-pulsed immature autologous dendritic cells. Lung cancer (Amsterdam, Netherlands) 2007; 57:365-72.
29. Becker J C, Andersen M H, Hofmeister-Muller V, et al. Survivin-specific T-cell reactivity correlates with tumor response and patient survival: a phase-II peptide vaccination trial in metastatic melanoma. Cancer Immunol Immunother 2012; 61:2091-103.
30. Tanaka M, Butler M O, Ansen S, et al. Induction of HLA-DP4-restricted anti-survivin Th1 and Th2 responses using an artificial antigen-presenting cell. Clin Cancer Res 2011; 17:5392-401.
31. Widenmeyer M, Griesemann H, Stevanovic S, et al. Promiscuous survivin peptide induces robust CD4+ T-cell responses in the majority of vaccinated cancer patients. Int J Cancer 2012; 131:140-9.
32. Rosenberg S A, Yang J C, Restifo N P. Cancer immunotherapy: moving beyond current vaccines. Nature medicine 2004; 10:909-15.
33. Gabrilovich D I. Combination of chemotherapy and immunotherapy for cancer: a paradigm revisited. The lancet oncology 2007; 8:2-3.
34. Liu G, Black K L, Yu J S. Sensitization of malignant glioma to chemotherapy through dendritic cell vaccination. Expert review of vaccines 2006; 5:233-47.
35. Brody J D, Goldstein M J, Czerwinski D K, Levy R. Immunotransplantation preferentially expands T-effector cells over T-regulatory cells and cures large lymphoma tumors. Blood 2009; 113:85-94.
36. Rapoport A P, Stadtmauer E A, Aqui N, et al. Restoration of immunity in lymphopenic individuals with cancer by vaccination and adoptive T-cell transfer. Nat Med 2005; 11:1230-7.
37. Rapoport A P, Aqui N A, Stadtmauer E A, et al. Combination immunotherapy using adoptive T-cell transfer and tumor antigen vaccination on the basis of hTERT and survivin after ASCT for myeloma. Blood; 117:788-97.
38. Andersen M H, Pedersen L O, Becker J C, Straten P T. Identification of a cytotoxic T lymphocyte response to the apoptosis inhibitor protein survivin in cancer patients. Cancer research 2001; 61:869-72.
39. Casati C, Dalerba P, Rivoltini L, et al. The apoptosis inhibitor protein survivin induces tumor-specific CD8+ and CD4+ T cells in colorectal cancer patients. Cancer Res 2003; 63:4507-15.
40. Pisarev V, Yu B, Salup R, Sherman S, Altieri D C, Gabrilovich D I. Full-length dominant-negative survivin for cancer immunotherapy. Clin Cancer Res 2003; 9:6523-33.
41. Palumbo A, Bringhen S, Bruno B, et al. Melphalan 200 mg/m(2) versus melphalan 100 mg/m(2) in newly diagnosed myeloma patients: a prospective, multicenter phase 3 study. Blood 2010; 115:1873-9.
42. Allred D C, Harvey J M, Berardo M, Clark G M. Prognostic and predictive factors in breast cancer by immunohistochemical analysis. Mod Pathol 1998; 11:155-68.

APPENDIX I

International Uniform Response Criteria for Multiple Myeloma (IWG)
(Leukemia (2006) 20: 1467-1473)
Summary Table

| Response Subcategory | Response Criteria |
|---|---|
| sCR | CR as defined below plus normal FLC ratio and absence of clonal cells in bone marrow by immunohistochemistry or immunofluorescence[1] |
| CR | Negative immunofixation on the serum and urine, disappearance of any soft tissue plasmacytomas, and ≤5% plasma cells in bone marrow |
| VGPR | Serum and urine M-protein detectable by immunofixation but not on electrophoresis or 90% or greater reduction in serum M-protein with urine M-protein level <100 mg per 24 hours |
| PR | ≥50% reduction of serum M-protein and reduction in 24 hour urinary M-protein by ≥90% or to <200 mg per 24 hours<br>If the serum and urine M-protein are immeasurable, a ≥50% decrease in the difference between involved and uninvolved FLC levels is required in place of the M-protein criteria.<br>If serum and urine M-protein and serum FLC are immeasurable[2], then ≥50% reduction in plasma cells is required in place of M-protein, provided baseline bone marrow plasma cell percentage was ≥30% |

APPENDIX I-continued

International Uniform Response Criteria for Multiple Myeloma (IWG)
(Leukemia (2006) 20: 1467-1473)
Summary Table

| Response Subcategory | Response Criteria |
|---|---|
| | In addition to the above listed criteria, if present at baseline, a ≥50% reduction in the size of soft tissue plasmacytomas is also required |
| SD | Not meeting criteria for CR, VGPR, PR, MR or PD |
| PD | Progressive Disease requires any one or more of the following: Increase of ≥25% from baseline in: serum M-component and/or (the absolute increase must be ≥0.5 g/dL) urine M-component and/or (the absolute increase must be ≥200 mg/24 h) Only in subjects without measurable serum and urine M-protein levels: the difference between involved and uninvolved FLC levels. The absolute increase must be >10 mg/dL. Bone marrow plasma cell percentage: the absolute % must be ≥10% Definite development of new bone lesions or soft tissue plasmacytomas or definite increase in the size of existing bone lesions or soft tissue plasmacytomas Development of hypercalcemia (corrected serum calcium >11.5 mg/dL or 2.65 mmol/L) that can be attributed solely to the plasma cell proliferative disorder |

Footnotes:
[1]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of >4:1 or <1:2.
[2]Measurable disease: serum M protein >1 g/dL, urine M-protein >200 mg/24 hr, or serum involved FLC levels >10 mg/dL with a normal κ/λ ratio.
FreeLite ™ Disease Response Criteria
CR: For those patients being followed by serum free light chain (and NO measurable serum or urine M-spike), which were immunofixation negative at enrollment, normalization of serum free light chain ratio.
PR: If only measurable parameter is serum immunoglobulins free light chain (FLC), EITHER of the following changes quality as partial response:
A 50% decrease in the difference between involved and uninvolved FLC levels; OR
A 50% decrease in the level of involved FLC AND a 50% decrease (or normalization) in the ratio of involved/uninvolved FLC
MR: 25-49% reduction in the level of the serum monoclonal paraprotein. Patients being followed by serum immunoglobulins free light chain only will not be assessed for MR category.
PD: If only measurable parameter is serum immunoglobulins free light chain (FLC), either of the following qualify as progression:
50% increase in the difference between involved and uninvolved FLC levels from the lowest response level, which must also be an absolute increase of at least 10 mg/dL; OR
50% increase in the level of involved FLC AND a 50% increase in the ratio of involved/uninvolved FLC from the lowest response level.

APPENDIX II

Common and expected toxicity associated with high dose melphalan and autologous transplant (From Palumbo et al.[41])

| Grade 3/4 adverse events | MEL200 (N = 149), no. (%) |
|---|---|
| Hematologic | |
| Grade 4 neutropenia, no. (%) | 114 (77) |
| Grade 4 neutropenia duration, d | |
| Median | 6 |
| Range | 0-15 |
| Grade 4 thrombocytopenia, no. (%) | 113 (76) |
| Grade 4 thrombocytopenia duration, d | |
| Median | 1 |
| Range | 0-20 |
| Red cell transfusion, no. (%) | 43 (29) |
| Platelet transfusion, no. (%) | 82 (56) |
| Hospitalization after engraftment | |
| No. of patients (%) | 100 (68) |
| Median, d | 3 |
| Range, d | 1-25 |
| Intravenous antibiotics | |
| No. of patients (%) | 60 (41) |
| Median, d | 7 |
| Range, d | 2-28 |
| Nonhematologic | |
| Mucositis, no. (%) | 26 (17) |
| Gastrointestinal, no. (%) | 16 (11) |
| Diarrhea | 7 |
| Vomiting | 9 |
| Infection, no. (%) | 60 (40) |
| Neutropenic fever | 26 |
| Pneumonia | 11 |
| Sepsis | 14 |
| Central venous catheter | 2 |
| Viral | 4 |
| Other | 3 |
| Thromboembolism, no. (%) | 3 (2) |
| Deep vein thrombosis | 1 |
| Pulmonary embolism | 2 |
| Renal, no. (%) | 1 (1) |
| Cardiac, no. (%) | 1 (1) |
| Pulmonary, no. (%) | 1 (1) |
| Neurologic, no. (%) | 1 (1) |
| Bleeding, no. (%) | 1 (1) |
| Coagulation, no. (%) | 0 (0) |
| At least 1 event, no. (%) | 67 (45) |

Appendix III: Criteria for Diagnosis of Multiple Myeloma & Clinical Myeloma Staging System Patients are eligible for the trial if they meet the criteria for diagnosis per the major and minor criteria, or the criteria for symptomatic myeloma.

Criteria for Diagnosis of Multiple Myeloma

Major Criteria:
1. Plasmacytomas on tissue biopsy
2. Bone marrow plasmacytosis (>30% plasma cells)
3. Monoclonal Immunoglobulin spike on serum electrophoresis: IgG >3.5 g/dL or IgA >2.0 g/dL; kappa or lambda light chain excretion >1.0 g/day on 24-hour urine protein electrophoresis Minor Criteria:
   a. Bone marrow plasmacytosis (>10-30% plasma cells)
   b. Monoclonal Immunoglobulin spike present, but of lesser magnitude than given above
   c. Lytic bone lesions
   d. Normal IgM <50 mg/dL, IgA <100 mg/dL, or IgG <600 mg/dL Any of the Following Sets of Criteria Will Confirm the Diagnosis:
   Any two major criteria
   Major criterion 1 plus minor criterion b, c or d
   Major criterion 3 plus minor criterion a or c
   Minor criteria a, b and c or a, b and d Symptomatic Multiple Myeloma[29]

Symptomatic multiple myeloma requires the presence of related organ or tissue impairment (end organ damage, including bone lesions) described below:
1—Hypercalcemia is defined as serum calcium ≥11 mg/dL (2.75 mmol/L)
2—Renal insufficiency is defined as a serum creatinine ≥2 mg/dL (173 mmol/L)
3—Anemia is defined as a hemoglobin concentration ≤10 g/dL
4—Lytic lesions on skeletal survey or other imaging modality (MRI/CT)
5—Biopsy confirmed amyloidosis Appendix V: Survivin Expression by Immunohistochemistry The tissues will be stained for Survivin, using a rabbit polyclonal antibody (Novus Bgicals, Inc.). The slides will be dewaxed by heating at 55° C. for 30 minutes and by three washes, five minutes each, with xylene. Tissues will be rehydrated by a series of five-minute washes in 100%, 95%, and 80% ethanol, and distilled water. Endogenous peroxidase activity will be blocked with 3% hydrogen peroxide for 20 minutes. After blocking with universal blocking serum (Ventana Medical Systems, Inc., Tucson, Arizona) for 30 minutes, the samples will be incubated with anti-Survivin rabbit polyclonal antibody (dilution 1:8000) at 4° C. overnight. The samples will then be incubated with biotin-labeled secondary antibody and streptavidin-horseradish peroxidase for 30 minutes each (Ventana Medical Systems). The slides will be developed with 3,3'-diaminobenzidine tetrahydrochloride substrate (Ventana Medical Systems Inc.) and counterstained with hematoxylin (Ventana Medical Systems Inc. Tucson, Arizona). The tissue samples will be dehydrated and coversliped. Standard cell conditioning (following the Ventana proprietarian recommendations) was used for antigen retrieval. The specificity of the anti-Survivin polyclonal antibody will be confirmed by using survivin overexpressing and Survivin KO cell lines. Negative control will be included by omitting Survivin antibody during the primary antibody incubation step.

Immunohistochemical data analysis. The Survivin stained tissues will be examined by an expert pathologist (DC). The positive reaction of Survivin will be scored into four grades, according to the intensity of the staining: 0, 1+, 2+, and 3+. The percentages of Survivin positive cells will also be scored into five categories: 0 (<5%), 1 (5-25%), 2 (26-50%), 3 (51-75%), and 4 (76-100%). The product of the intensity by percentage scores will be used as the final score. A product score <1 will be considered negative.

APPENDIX VI

| | | | | | | |
|---|---|---|---|---|---|---|
| Follow up schedule | | | | | | |

| Event | Day after transplant* | History | Physical Exam | Laboratory Parameters | Vaccine Injection | Toxicity Case Report Form | IWG response assessment |
|---|---|---|---|---|---|---|---|
| First day, dendritic cell collection apheresis | day −42 | X | X | X | | | |
| Vaccine #1 | day −35 | X | X | X | X | X | |
| First day, stem cell collection apheresis | day −14 | X | X | X | | X | |
| Vaccine #32 | day +7 | X | X | X | X | X | |
| Vaccine #43 | day +21 | X | X | X | X | X | |
| Immune response evaluation 1 | day +60 | X | X | X | | X | |
| Immune response evaluation 2 | day +90 | X | X | X | | X | X |
| Immune response evaluation 3 | day +180 | X | X | X | | X | X |

*The day in relation to transplant is suggested. These evaluations will occur at a time consistent with that described in the protocol for each event. For the referenced dates, a window of time compared to transplant will be acceptable as follows:
+60 (+/−15 days)
+90 (+/−15 days)
+180 (+/−20 days)

Note:
Physical exam must include lymph node examination and site of the injections.

Example 12—Safety and Biological Activity of Survivin Dendritic Cell Vaccine The experiments of Example 12 were designed to test the safety and biological activity of a survivin dendritic cell vaccine. A sample size of 10 patients with Multiple Myeloma will establish the feasibility of the approach, and allow for evaluation of the expected increased T cell response against survivin. Vaccine will be administered in two stages. After the first survivin vaccination, patients will be mobilized with G-CSF and both in vivo-primed T cells and stem cells will be collected in the same apheresis (the graft). T cells and the CD34 progenitor cells will be transferred back to the patient at the time of autologous graft infusion. Patients will receive re-vaccination on day 21 after transplant. The immune response to survivin will be assessed for 6 months and compared to the pre-vaccine response. To validate the patient's ability to mount an immune response the inventors will simultaneously vaccinate against PREVNAR13®, a pneumococcus vaccine able to elicit T cell immune responses. Immunologic responses will be measured at baseline, after stem cell mobilization/collection, 60 days, 90 days and 180 days after transplant. Peripheral blood mononuclear clles (PBMCs) will be isolated and stored in liquid N2. G-CSF cell mobilization, mononuclear cell collection, melphalan chemotherapy, and transplant infusion will all be per institutional standards.

Primary objectives for these experiments include: (1) determining the safety of an autologous dendritic cell (DC) adenovirus (Ad) vaccine expressing the mutant protein survivin (mS) (DC:AdmS) when administered to patients with myeloma before and at day +21 after autologous hematopoietic stem cell transplant; and (2) evaluating the ability of DC:AdmS to induce T cell immune responses against survivin when administered to patients with myeloma before and at day +21 after autologous hematopoietic stem cell transplant. Secondary objectives for these experiments include: (1) determining the ability of a survivin peptide pool to elicit T cell IFN-gamma production (ELISPOT, flow cytometry) or proliferation; (2) evaluating immunomodulatory phenotypes of T cell subsets before and after vaccination using flow cytometry; (3) determining the clinical response of treated patients and compare to historical controls; (4) evaluating immune responses to other tumor-associated antigens before and after vaccine; and (5) determining T cell responses against PREVNAR13® (pneumococcal 13-valent) vaccine concurrently administered at the time of survivin vaccine.

The 36 kD adenoviral (pAd) vectors, pAdTrack-CMV and pAdEasy-1 vectors, for homologous recombination in bacteria were kindly provided by B. Vogelstein (Johns Hopkins University School of Medicine, Baltimore, Maryland, USA) and have been described (Mesri et al., 2001; Luo et al., 2007). The cDNAs for Thr34→Ala survivin mutant (T34A) containing 5' HindIII and 3' XbaI sites were inserted in pAdTrack downstream of the cytomegalovirus (CMV) promoter (FIG. 16A) to generate pAd-WT or pAd-T34A. Each shuttle vector was linearized with PmeI, electroporated in *Escherichia coli* BJ5183, and colonies were selected in 50 µg/ml of kanamycin. Each pAd construct (4-10 µg) was digested with PacI, transfected in 293 cells by Lipofectamine (Life Technologies Inc., Rockville, Maryland, USA), and cultures were monitored for expression of green fluorescent protein (GFP), by fluorescence microscopy. The cell pellets were suspended in 1 ml PBS, pH 7.4, and after three cycles of freezing and thawing, 1 ml of viral lysate supernatant was used to infect 3-5×10$^6$ 293 cells. Viruses were harvested at 2-3-day intervals. To generate high-titer viral stocks, this process was repeated 3-5 times with a total of 5×10$^8$ packaging cells, and viral particles were purified by CsCl banding. Green fluorescence forming units (GFU) were estimated by serial dilution of the virus stock in transduced 293 cells. To detect a potential contamination of viral stocks with replication-competent adenoviral particles, HeLa cells (8×10$^4$) in C-6-well plates were infected with pAd-GFP or pAd-T34A at moi of 1,250 for 8 hours and grown for 3 days at 37° C. Cell extracts were prepared by freezing and thawing and supernatants were used to successively infect a second culture of HeLa cells, which was analyzed for viral transduction by GFP expression after an additional 2-day interval at 37° C. Expression of survivin protein in transduced cultures was determined by Western blot analysis, using an Ab to full-length recombinant survivin (NOVUS Biologicals Inc., Littleton, Colorado, USA). FIGS. 16A-D depict construction and expression of single mutant (T34A) pAd-survivin vectors.

Materials and Methods

Dendritic Cells (Monocyte-Derived Myeloid Dendritic Cells).

The target cells for this study are autologous dendritic cells from peripheral blood, grown in an ex vivo culture system. As a consequence of the growth conditions, the viral vector will primarily have access to dendritic cells, reducing the amount of simultaneous infection of other cell types. Other cell types that are infected are all of similar derivation to the dendritic cells, and may in fact increase the immunogenicity of the final gene transferred product.

Cell Collection Method.

The method of collection will be apheresis (unmobilized). Patients who are enrolled in this study will have a single leukopheresis procedure performed at the Moffitt Apheresis Facility. Approximately four blood volumes will be processed using the Terumo Spectra Optia® Apheresis System. Leukopheresis products will be delivered to the Cell Therapy Facility for further processing.

Donor Screening.

Donor screening will be performed according to 21 CFR Part 1271 "Eligibility Determination for Donors of Human Cells, Tissues and Cellular and Tissue-Based Products (HCT/Ps)". All autologous donors receive a complete medical/surgical history and physical. In addition, all autologous donors complete a Donor Health History Screening Questionnaire.

Tabulation of Testing.

Autologous donors are tested for the following infectious disease markers (IDMs):

HIV ½ Ab (donor)

Hepatitis B surface Ag (donor)

Hepatitis B Core Ab (donor)

Hepatitis C Ab (donor)

HIV/HCV/HBV NAT (donor)

RPR for *Treponema pallidum* (syphilis)

HTLV-I/II Ab screen (donor)

CMV IgG/IgM (donor)

Varicella zoster IgG/IgM

HSV IgG ½

Chagas
Autologous donors are tested for the following additional labs:
Sickle cell screen to assess for hemoglobinopathies
Beta HCG for females of child bearing age Product Manufacturing—Procedures.

Frozen ficolled mononuclear cells (MNC) are thawed and enriched for monocytes through plastic adherence. The monocyte enriched population of cells is cultured in the presence of GM-CSF and IL-4 for 5-6 days to induce differentiation into dendritic cells (DC). DC are harvested and infected with Ad-mSurvivin. Infected cells are cultured for an additional 2 days and harvested for patient vaccination. The target dose is $10 \times 10^6$ mSurvivin+ DC per vaccine with a maximum of $15 \times 10^6$ cells per vaccine.

Preparations of Autologous or Allogeneic Cells.

A freshly collected leukopheresis product will be subjected to density gradient separation with Ficoll-Paque PLUS using the HAEMONETICS® CELL SAVER® 5 Blood Recovery System. The CELL SAVER® 5 is a semi-automated, closed system using centrifugation and density gradient media to separate blood components into plasma, mononuclear cells (MNC) and red blood cells (RBC). The mononuclear cell fraction will be harvested and cryopreserved in 10% DMSO/2.5% human serum albumin at a concentration of $3 \times 10^8$ cells/mL. Cryopreserved cells will be stored in the vapor phase of liquid nitrogen (−190° C.) until needed for vaccine production. A flow chart showing processes for preparation of MNCs and apheresis for cryopreservation is shown in FIG. 17.

Just prior to vaccination, frozen mononuclear cells will be thawed, washed and placed in CELLGRO® DC culture medium in tissue culture flasks at a concentration of $1-2 \times 10^6$ cells/ml. After culturing for 2 hours, non-adherent cells will be removed and the flasks will be recharged with culture medium supplemented with 5 ng/ml each of GM-CSF and IL-4 and incubated for 5 days. At the completion of incubation, the non-adherent and loosely adherent cells will be collected and used for a 2-3 hour infection with Ad-mS at an optimal Multiplicity of Infection (MOI) of 1000. At the end of the 2-hour incubation, culture medium will be added to a final concentration of $1 \times 10^6$ cells/ml, and cells will be incubated in flasks for an additional 40-46 hours, at which time cells will be harvested, washed and analyzed. FIGS. 18-20 are flow charts showing processes for thawing and culturing during dendritic cell production (FIG. 18), harvest and Ad-mS infection of dendritic cells (FIG. 19), and harvesting of Ad-mS infected dendritic cells for infusion (FIG. 20).

Final Formulation:

Formulation/Infusion Buffer: PlasmaLyte-A with 1% HSA

Excipients: PlasmaLyte-A with 1% HSA

Cell Density/Concentration in the Final Product: $5-15 \times 10^6$/ml

Storage Method Prior to Use: 2-8° C.

Tabulation of Tests, Manufacturing Step, Test Methods, Criteria, and Test Sensitivity & Specificity

| Test | Manufacturing Step where Performed | Method | Criteria | Sensitivity | Specificity |
|---|---|---|---|---|---|
| Sterility | Pre-ficoll, pre-cryopreservation, thawing, pre-infection, final product | BacT/ALERT ® Aerobic and Anaerobic System | Negative | | |
| Mycoplasma | During final collection of cells from culture | Venor ™GeM Mycoplasma Detection Kit | Negative | 2-5 mycoplasma per sample volume | N/A |
| Purity (endotoxin) | Final product | Endosafe ®-PTS ™ | <5.0 EU/kg body weight per hour | 0.005-10 EU/ml | |
| Purity (other contaminants) | Immediately prior to final formulation | BD FACSCanto ™ II flow cytometry | ≥30% survivin+, CD11c+, HLA-DR+ | N/A | N/A |
| Identity | Immediately prior to final formulation | BD FACSCanto ™ II flow cytometry | ≥30% survivin+, CD11c+, HLA-DR+ | N/A | N/A |
| Potency | Immediately prior to final formulation | BD FACSCanto ™ II flow cytometry | ≥30% survivin+, CD11c+, HLA-DR+ | N/A | N/A |
| Others (cell counts) | Pre-ficoll, pre-cryopreservation, pre-plastic adherence | KX-21N Hematology Analyzer Sysmex Cell Counter | N/A | N/A | N/A |
| Others (cell viability) | Final product | Acridine Orange/Propidium Iodine staining by Cellometer | >70% | N/A | N/A |

Test Methods.

Sterility Testing (Bacterial and Fungal Testing): Required suitable sterility tests include the test described in 21 CFR 610.12 and the United States Pharmacopoeia (USP) <71> Sterility Tests (23$^{rd}$ edition, 1995). Current FDA Guidance recommends that automated sterility testing procedures are acceptable if they have been validated against established methods. Our facility has successfully validated BacT/ALERT® 3D (bioMérieux, Inc., Durham, NC) for detecting the presence or absence of microorganisms, using a 14-day incubation period, and this testing method has been used for all FDA-approved INDs at our institution.

*Mycoplasma* Testing.

*Mycoplasma* testing will be performed in-house on the product after culture at harvest but prior to cell washing. Testing will be conducted on both cells and supernatant by use of the Venor™ GeM *Mycoplasma* Detection Kit.

Purity: Pyrogenicity/Endotoxin Testing.

The Limulus Amebocyte Lysate test method (LAL), Endosafe®-PTS™ (Charles River Laboratories), will be used as a pyrogenicity test to detect endotoxin. The upper limit of acceptance criterion for endotoxin administered intravenously will be <5 EU/kg body weight/hour.

Purity: Other Cell Contaminants.

Analysis of DC immunophenotypes will be determined from cells using the following fluorescence-conjugated (FITC, PE or PerCP) mouse anti-human monoclonal antibodies: intracellular survivin, cell surface markers related to lineage (CD3, CD14, CD20, CD56) and MHC class II (HLA-DR). Appropriate isotype controls will be set up in parallel. The cells will be incubated for 20 minutes at room temperature and washed in phosphate-buffered saline (PBS) containing 0.5% bovine serum albumin. A minimum number of 20,000 events will be collected on a BD FACSCanto™ II flow cytometer using Diva v6.1.2 and Clinical v2.4 software for data acquisition and analysis. Cells that are survivin expressing dendritic cells (survivin+, CD11c+, HLA-DR+); survivin non-expressing dendritic cells (survivin−, CD11c+, HLA-DR+), and survivin producing and non-producing non-dendritic cells (survivin+/−, lineage+, HLA-DR+/−) will be enumerated. Pre-clinical studies have shown that approximately one third of the cells harvested express survivin. There is no known mechanism whereby the remaining cells may have a deleterious effect on the recipient.

Purity: Other Residual Contaminants.

It is anticipated that extensive washing with Harvest Medium (PlasmaLyte-A with 1% HSA) will remove (via dilution, centrifugation and discarding) residual proteins, viral vector and cytokines from the final infusion product. Cells will be washed free of residual culture media prior to infusion. Therefore, only trace amounts of residual reagents will be present in the final product.

Identity and Potency: Presence of Viral Vector.

The ex vivo genetically modified DC cell product, will be tested by flow cytometry to measure the presence of intracellular survivn+, CD11c+ and HLA-Dr+, which represent the target cells.

Cell Counts & Viability.

Final Cell Counts and Viability will be performed on the Cellometer® Vision using AO/PI. The lower acceptable limit for viability is 70%.

Final Product Release Criteria/Specifications
Tabulation of Final Product Release Criteria Tests, Test Methods, Criteria, Test Sensitivity & Specificity

| Test | Method | Criteria | Results Available Prior to Release |
|---|---|---|---|
| Bacteriologic sterility | BacT/ALERT ® Aerobic and Anaerobic System | Negative | No |
| Gram Stain | Facility SOP# CTF-VI-006 | No organisms seen | Yes |
| Mycoplasma | Venor™GeM Mycoplasma Detection Kit | Negative | Yes |
| Endotoxin | Endosafe ®-PTS ™ | <5.0 EU/kg body weight per hour | Yes |
| Viability | AO/PI Staining by Cellometer ® Vision | >70% viable | Yes |
| Cell Dose | KX-21N Hematology Analyzer Sysmex Cell Counter | 5-15 × $10^6$/ml | Yes |
| Cell Phenotype | BD FACSCanto ™ II flow cytometer | ≥30% survivin+, CD11c+, HLA-DR+ | Yes |

Description of Test Methods

Sterility Testing (Bacterial and Fungal Testing).

As described previously

Gram Stain.

Sterility testing results will not be available prior to infusion. Under these circumstances, a rapid microbial detection test, Gram stain, will be performed. Release criteria for sterility will be based on a negative result of the Gram stain. Should sterility testing results from the BacT/Alert® 3D method test positive, the principle investigator and IND holder will be notified. A positive result will provide information for the medical management of the subject, and trigger an investigation of the cause of the sterility failure. The sterility culture on the final formulated product will be continued to obtain the full 14-day sterility test result even after the product has been given to the patient. In all cases where product release is prior to obtaining results from a full 14-day sterility test, the investigational plan will address the actions to be taken in the event that the 14 day sterility test is determined to be positive after the product is administered to a subject.

*Mycoplasma* Testing.

As described previously

Purity: Pyrogenicity/Endotoxin Testing.

As described previously.

Viability.

As described previously

Cell Dose.

As described previously

Cell Phenotype.

Identity and Potency: As described previously.

Product Stability.

Stability testing will be performed to establish that the product is sufficiently stable for the time period required by the study. Stability testing will be performed according to "Quality of Biotechnological Products: Stability Testing of Biotechnological/Biological Products," ICH Guideline Q1A (R): "Stability Testing of New Drugs and Products". The inventors have developed the stability protocol and data for both in-process material and the final product. Data will include a measure of product sterility, identity, purity, quality, and potency. Sampling time points (including a zero-time point) and testing temperature will be determined to assign a six hour duration of storage (expiration) at 2-8° C. It will be demonstrated that the product is stable between the time of final product formulation and infusion to subjects to aid in establishing the expiration-dating period.

Cryopreserved Cells: NA

Only the original apheresis product will be cryopreserved, following preparation of a mononuclear cell preparation via ficoll density gradient separation. The apheresis product will remain frozen in the vapor phase of liquid nitrogen for a short interval (expected to be less than 30 days) prior to thaw for manufacture of the DC vaccine.

Other Intermediate Holding Steps: All intermediate holding steps will occur at 4-8° C.
In-Process Stability Testing: NA
Product Formulation to Patient Infusion: $5\text{-}15\times10^6$/ml PlasmaLyte-A with 1% HSA
Final Product Stability Testing:

Stability testing must be performed during early phases of the clinical trial to establish that the product is sufficiently stable for the time period required by the study.
Shipping Conditions:

The product will be delivered by facility personnel from the manufacturing site to the clinical site, using validated, temperature-controlled shipping containers to demonstrate that product integrity, sterility, and potency are maintained under the proposed 2-8° C. shipping conditions.
Product Tracking For all products collected by or received in the Moffitt Cell Therapy Facility a unique component identification number is assigned which allows tracking from the donor to the recipient or final distribution and from the recipient or final disposition to the donor.

Samples and aliquots of cellular therapy products used for testing are labeled with the component number to permit tracking of the sample or aliquot to the cellular therapy product and/or person from whom it was taken. There is a mechanism to identify the individual drawing the sample, the date, the time (where appropriate), and the sample source.

Every product processed by the Moffitt Cell Therapy Facility is linked to the reagents' lot numbers and equipment used in said process. The technologist responsible for each step of processing documents this in the batch process record.
Labeling Purpose: To ensure proper labeling and identification of cellular therapy products for intermediate processing, storage and/or distribution of products for autologous and allogeneic use. Labeling of all products will be conducted in a manner to prevent mislabeling or misidentification of cellular therapy products, samples, and associated records.
In-Process Labeling:

Intermediate processing steps: During intermediate processing steps, a partial label will be used when transferring a product to a secondary container and when samples are removed from the product for assays or QC testing. The label will contain with the following:
Patient Name
Medical Record Number
Product Name
Unique alphanumeric accession number
Date of collection
"For Autologous Use Only"
Final Product Labeling:
Patient Name
Medical Record Number
Product Name
Unique alphanumeric accession number
Storage Temperature
Expiration Date & Time
Date of Product Manufacture
"Caution: New Drug Limited by Federal Law to Investigational Use"
"For Autologous Use Only"
Container Closure & Integrity Final product will be transported from the Moffitt Cell Therapy Facility to the Moffitt Infusion Center in a 1 ml syringe approved for clinical use. The syringe will be capped and placed in a plastic zip lock bag and labeled as described.
Validation and Qualification of the Manufacturing Process
QA/QC Program: Described in BB-MF 13743
Manufacturing Process Validation:
Development and Optimization of Survivin Expressing Dendritic Cells The development and optimization of production of mutant survivin (Ad-mS)-expressing DC was performed in multiple phases. These steps are described below.
1. Titration of the Ad-mS Adenovirus Ad-mS virus was purchased from Vivante GMP Solutions (now part of Lonza) and received in 2010. The vp/ml was provided by the company ($1.10\times10^{12}$ vp/ml); however, the infectious units (IFU) were not determined and no functional testing was performed. The inventors titered the virus using the QuickTiter™ Adenovirus Titer Immunoassay Kit from CELL BIOLABS, INC. The working titer of the virus was found to be $7.90\times10^{10}$ IFU/ml and was used in all subsequent experiments.
2. Development of Survivin Detection Assay Preliminary work using Ad-mS DC did not have a direct method for detection of survivin expression. The inventors developed an intracellular flow cytometry assay to detect survivin expression. This was compared to immunohistochemistry staining of DC.
3. Optimization of DC Infection Our department has completed previous vaccine trials using DC infected with Adenovirus. This trial utilized 15,000 vp/DC; this viral dose is approximately 1000 IFU/cell. That experience led us to infect DC with a range of Multiplicities of Infection (MOI; IFU/cell) centered on an MOI of 1000. Based on the results in FIG. 21, an MOI of 1000 will be used for future experiments.
Biostatistics NA
PRECLINICAL STUDIES
CLINICAL STUDIES
Protocol Title:
Evaluating the Safety and Biological Activity of a Dendritic Cell Survivin Vaccine in Patients with Multiple Myeloma Undergoing Autologous Hematopoietic Cell Transplantation
Subject Population:
Multiple Myeloma patients with survivin positive plasma cells on a bone marrow biopsy
Route of Administration:
Intradermal injection to one site that will drain to one of the axillary and/or inguinal lymph node basins
Dose:
$5\text{-}15\times10^6$ dendritic cells
Frequency:
One vaccine prior to autologous transplant and one vaccine post autologous transplant
Genetic, Biochemical, and Immunological Testing:
Determine CD4+ and CD8+ survivin specific T cell frequency before and after vaccination.
Analysis of INFγ producing T cells before and after vaccination.
Measurement of anti-pneumococcal IgG antibody titers and T cell responses against CRM adjuvant before and after vaccination.
Evaluation of immunomodulatory phenotypes by T cell subsets before and after vaccination.
1. Mesri M, Wall N R, Li J, Kim R W, Altieri D C. Cancer gene therapy using a survivin mutant adenovirus. The Journal of clinical investigation. 2001; 108(7):981-90.
2. Luo J, Deng Z L, Luo X, Tang N, Song W X, Chen J, Sharff K A, Luu H H, Haydon R C, Kinzler K W, Vogelstein B, He T C. A protocol for rapid generation of recombinant adenoviruses using the AdEasy system. Nature protocols. 2007; 2(5):1236-47.

EXEMPLIFIED EMBODIMENTS

Examples of embodiments of the invention include, but are not limited to:

Embodiment 1

An antigen presenting cell comprising a variant survivin polypeptide, or a nucleic acid sequence encoding the variant survivin polypeptide, wherein the variant survivin polypeptide comprises at least consecutive amino acids 16-87 (N-terminal zinc-binding baculovirus inhibitor of apoptosis protein repeat (BIR) domain) of the human wild-type survivin polypeptide (SEQ ID NO:1) modified to have an amino acid at position 34 which is other than threonine and an amino acid at position 84 which is other than cysteine, relative to the human wild-type survivin polypeptide, and wherein the variant survivin polypeptide:
(a) comprises a 142-amino acid sequence having at least 80% sequence identity to the human wild-type survivin polypeptide (SEQ ID NO:1), or
(b) is a subsequence (fragment) of the human wild-type survivin polypeptide (SEQ ID NO:1).

Embodiment 2

The antigen presenting cell of embodiment 1, wherein one or both of the amino acids at position 34 and at position 84 are nonpolar amino acids.

Embodiment 3

The antigen presenting cell of embodiment 1, wherein one or both of the amino acids at position 34 and at position 84 are alanine.

Embodiment 4

The antigen presenting cell of any one of embodiments 1 to 3, wherein the variant survivin polypeptide comprises the full-length human wild-type survivin polypeptide having an amino acid at position 34 which is other than threonine, and an amino acid at position 84 which is other than cysteine, as set forth as SEQ ID NO:2.

Embodiment 5

The antigen presenting of any one of embodiments 1 to 3, wherein the variant survivin polypeptide further includes at least consecutive amino acids 6-10, consecutive amino acids 89-97 (linker region), and consecutive amino acids 97-141 (coiled coil domain) of the human wild-type survivin polypeptide (SEQ ID NO:1).

Embodiment 6

The antigen presenting cell of any preceding embodiment, wherein the antigen presenting cell is a dendritic cell.

Embodiment 7

The antigen presenting cell of any preceding embodiment, wherein the antigen presenting cell is a human cell.

Embodiment 8

The antigen presenting cell of any preceding embodiment, wherein the variant survivin polypeptide comprises the amino acid sequence of SEQ ID NO:2 or SEQ ID NO:3.

Embodiment 9

The antigen presenting cell of any preceding embodiment, wherein the variant survivin polypeptide consists of the amino acid sequence of SEQ ID NO:2 or SEQ ID NO:3.

Embodiment 10

The antigen presenting cell of any preceding embodiment, wherein portions of the variant survivin polypeptide are presented on the cell surface of the antigen presenting cell.

Embodiment 11

A composition comprising antigen presenting cells of any one of embodiments 1 to 10; and a pharmaceutically acceptable carrier.

Embodiment 12

The composition of embodiment 11, further comprising an adjuvant.

Embodiment 13

The composition of embodiment 11, wherein the variant survivin polypeptide comprises the amino acid sequence of SEQ ID NO:2 or SEQ ID NO:3.

Embodiment 14

The composition of embodiment 11, wherein the variant survivin polypeptide comprises the amino acid sequence of SEQ ID NO:2 or SEQ ID NO:3.

Embodiment 15

A composition comprising a variant survivin polypeptide, or a nucleic acid sequence encoding the variant survivin polypeptide; and an adjuvant,
wherein the variant survivin polypeptide comprises at least consecutive amino acids 16-87 (N-terminal zinc-binding baculovirus inhibitor of apoptosis protein repeat (BIR) domain) of the human wild-type survivin polypeptide (SEQ ID NO:1) modified to have an amino acid at position 34 which is other than threonine and an amino acid at position 84 which is other than cysteine, relative to the human wild-type survivin polypeptide, and wherein the variant survivin polypeptide:
(a) comprises a 142-amino acid sequence having at least 80% sequence identity to the human wild-type survivin polypeptide (SEQ ID NO:1), or
(b) is a subsequence (fragment) of the human wild-type survivin polypeptide (SEQ ID NO:1).

Embodiment 16

The composition of embodiment 15, wherein the variant survivin polypeptide comprises the amino acid sequence of SEQ ID NO:2 or SEQ ID NO:3.

Embodiment 17

The composition of embodiment 15, wherein the variant survivin polypeptide consists of the amino acid sequence of SEQ ID NO:2 or SEQ ID NO:3.

Embodiment 18

A method for treating a malignancy, comprising administering to a subject in need of treatment an effective amount of:
(i) a variant survivin polypeptide, or
(ii) an expression construct comprising a nucleic acid sequence encoding the variant survivin polypeptide, or
(iii) an antigen presenting cell comprising the variant survivin polypeptide or the nucleic acid sequence encoding the variant survivin polypeptide,
wherein the variant survivin polypeptide comprises at least consecutive amino acids 16-87 (N-terminal zinc-binding baculovirus inhibitor of apoptosis protein repeat (BIR) domain) of the human wild-type survivin polypeptide (SEQ ID NO:1) modified to have an amino acid at position 34 which is other than threonine and an amino acid at position 84 which is other than cysteine, relative to the human wild-type survivin polypeptide, and wherein the variant survivin polypeptide:
(a) comprises a 142-amino acid sequence having at least 80% sequence identity to the human wild-type survivin polypeptide (SEQ ID NO:1), or
(b) is a subsequence (fragment) of the human wild-type survivin polypeptide (SEQ ID NO:1).

Embodiment 19

The method of embodiment 18, wherein the antigen presenting cells are those of any one of embodiments 1 to 10 or a composition of any one of embodiments 11 to 17.

Embodiment 20

The method of embodiment 18 or 19, wherein the antigen presenting cells are autologous cells.

Embodiment 21

The method of any one of embodiments 18 to 20, wherein the malignancy is myeloma.

Embodiment 22

The method of any one of embodiments 18 to 21, wherein the method further comprises administering one or more additional anti-cancer agents to the subject.

Embodiment 23

The method of any one of embodiments 18 to 22, wherein the method further comprises administering a chemotherapeutic drug (e.g., melphalan), immunomodulator, adjuvant, anemia drug (e.g., erythropoietin), radiation therapy, stem cell transplant, or a combination of two or more of the foregoing.

Embodiment 24

The method of any one of embodiments 18 to 23, wherein the method does not include administration of an anti-CD25 antibody.

Embodiment 25

The method of any one of embodiments 18 to 24, wherein the method does not include administration of a humanized IgG1 monoclonal antibody that binds specifically to the alpha subunit (p55 alpha, CD25, or Tac subunit) of the human high-affinity interleukin-2 (IL-2) receptor.

Embodiment 26

The method of any one of embodiments 18 to 25, wherein the subject is human.

Embodiment 27

The method of any one of embodiments 18 to 26, wherein the antigen presenting cells are administered by intradermal injection.

Embodiment 28

The method of embodiment 27, wherein the intradermal injection is at an anatomical site that drains to the axillary and/or inguinal lymph node basins of the subject.

Embodiment 29

The method of any one of embodiment 18, wherein the variant survivin polypeptide, expression construct, or antigen presenting cells are administered multiple times over a period of days.

Embodiment 30

The method of any one of embodiments 18 to 29, wherein the method further comprises conducting hematopoietic cell transplantation (hematopoietic stem cells or progenitor cells, e.g., from bone marrow, peripheral blood, or cord blood) on the subject.

Embodiment 31

The method of embodiment 30, wherein the hematopoietic cell transplant is autologous.

Embodiment 32

The method of embodiment 30 or 31, wherein the antigen presenting cells are administered before and after the hematopoietic cell transplantation.

Embodiment 33

The method of embodiment 30 or 31, further comprising conducting stem cell mobilization (e.g., using G-CSF) on the subject and collecting the hematopoietic cells from the subject prior to autologous hematopoietic cell transplantation.

Embodiment 34

The method of any one of embodiments 18 to 34, further comprising, prior to said administering, collecting mononuclear cells from the subject for production of the antigen presenting cells to be administered to the subject.

Embodiment 35

The method of embodiment 34, wherein the antigen presenting cells are cryopreserved prior to said administering.

Embodiment 36

The method of any one of embodiments 18 to 35, further comprising administering a chemotherapeutic agent (e.g., melphalan) before, during, or after said administering of the variant survivin polypeptide expression construct, or antigen presenting cells.

Embodiment 37

The method of embodiment 30, further comprising administering a chemotherapeutic agent (e.g., melphalan) during the hematopoietic cell transplantation.

Embodiment 38

The method of any one of embodiments 18 to 37, wherein the variant survivin polypeptide comprises the amino acid sequence of SEQ ID NO:2 or SEQ ID NO:3.

Embodiment 39

The method of any one of embodiments 18 to 37, wherein the variant survivin polypeptide consists of the amino acid sequence of SEQ ID NO:2 or SEQ ID NO:3.

Embodiment 40

A method for producing antigen presenting cells comprising a variant survivin polypeptide, or a nucleic acid sequence encoding the variant survivin polypeptide, comprising:
  contacting antigen presenting cells or their precursors with a variant survivin polypeptide, or transfecting antigen presenting cells or their precursors with an expression construct comprising a nucleic acid sequence encoding a variant survivin polypeptide,
  wherein the variant survivin polypeptide comprises at least consecutive amino acids 16-87 (N-terminal zinc-binding baculovirus inhibitor of apoptosis protein repeat (BIR) domain) of the human wild-type survivin polypeptide (SEQ ID NO:1) modified to have an amino acid at position 34 which is other than threonine and an amino acid at position 84 which is other than cysteine, relative to the human wild-type survivin polypeptide, and wherein the variant survivin polypeptide:
  (a) comprises a 142-amino acid sequence having at least 80% sequence identity to the human wild-type survivin polypeptide (SEQ ID NO:1), or
  (b) is a subsequence (fragment) of the human wild-type survivin polypeptide (SEQ ID NO:1).

Embodiment 41

The method of embodiment 40, wherein the expression construct is a viral vector, non-viral vector, or naked DNA.

Embodiment 42

The method of embodiment 40, wherein the expression construct is a viral vector selected from among adenovirus, adeno-associated virus, poxvirus, lentivirus, alphavirus, herpesvirus, retrovirus, and vaccina virus.

Embodiment 43

The method of any one of embodiments 40 to 42, wherein the method further comprises, prior to said transfecting, obtaining mononuclear cells for the production of myeloid dendritic cells.

Embodiment 44

The method of embodiment 43, wherein the mononuclear cells are obtained from a subject by apheresis.

Embodiment 45

The method of embodiment 43 or 44, wherein the mononuclear cells are cryopreserved before or after said transfecting.

Embodiment 46

The method of any one of embodiments 43 to 45, further comprising culturing the cells in chemically defined, serum-free hematopoietic cell medium, GM-CSF, and IL-4; and collecting the resulting antigen presenting cells before said transfecting.

Embodiment 47

A method for inducing an immune response in a subject, comprising administering to the subject an effective amount of:
  (i) a variant survivin polypeptide, or
  (ii) an expression construct comprising a nucleic acid sequence encoding the variant survivin polypeptide, or
  (iii) an antigen presenting cell comprising the variant survivin polypeptide or the nucleic acid sequence encoding the variant survivin polypeptide,
  wherein the variant survivin polypeptide comprises at least consecutive amino acids 16-87 (N-terminal zinc-binding baculovirus inhibitor of apoptosis protein repeat (BIR) domain) of the human wild-type survivin polypeptide (SEQ ID NO:1) modified to have an amino acid at position 34 which is other than threonine and an amino acid at position 84 which is other than cysteine, relative to the human wild-type survivin polypeptide, and wherein the variant survivin polypeptide:
  (a) comprises a 142-amino acid sequence having at least 80% sequence identity to the human wild-type survivin polypeptide (SEQ ID NO:1), or
  (b) is a subsequence (fragment) of the human wild-type survivin polypeptide (SEQ ID NO:1).

Embodiment 48

The method of embodiment 47, wherein the antigen presenting cells are those of any one of embodiments 1 to 10 or a composition of any one of embodiments 11 to 17.

Embodiment 49

The method of embodiment 47 or 48, wherein the variant survivin polypeptide comprises the amino acid sequence of SEQ ID NO: 2 or SEQ ID NO:3.

Embodiment 50

The method of embodiment 47 or 48, wherein the variant survivin polypeptide consists of the amino acid sequence of SEQ ID NO:2 or SEQ ID NO:3.

Embodiment 51

The method of any one of embodiments 47 to 50, wherein the subject has cancer.

Embodiment 52

The method of any one of embodiments 47 to 51, wherein the subject is human.

We claim:

1. An antigen presenting cell comprising a variant survivin polypeptide, or a nucleic acid sequence encoding the variant survivin polypeptide, wherein the variant survivin polypeptide comprises at least consecutive amino acids 16-87 (N-terminal zinc-binding baculovirus inhibitor of apoptosis protein repeat (BIR) domain) of the human wild-type survivin polypeptide (SEQ ID NO:1) modified to have an alanine both at position 34 and at position 84, relative to the human wild-type survivin polypeptide, and wherein the variant survivin polypeptide is a subsequence (fragment) of the human wild-type survivin polypeptide (SEQ ID NO: 1).

2. The antigen presenting cell of claim 1, wherein the variant survivin polypeptide comprises the full-length human wild-type survivin polypeptide having an alanine both at position 34 and at position 84, as set forth as SEQ ID NO: 3.

3. The antigen presenting cell of claim 1, wherein the variant survivin polypeptide further includes at least consecutive amino acids 6-10, consecutive amino acids 89-97 (linker region), and consecutive amino acids 97-141 (coiled coil domain) of the human wild-type survivin polypeptide (SEQ ID NO:1).

4. The antigen presenting cell of claim 1, wherein portions of the variant survivin polypeptide are presented on the cell surface of the antigen presenting cell.

5. A composition comprising antigen presenting cells of claim 1; and a pharmaceutically acceptable carrier.

6. The composition of claim 5, further comprising an adjuvant.

7. A composition comprising a variant survivin polypeptide, or a nucleic acid sequence encoding the variant survivin polypeptide; an antigen presenting cell, and an adjuvant,
wherein the variant survivin polypeptide comprises at least consecutive amino acids 16-87 (N-terminal zinc-binding baculovirus inhibitor of apoptosis protein repeat (BIR) domain) of the human wild-type survivin polypeptide (SEQ ID NO:1) modified to have an alanine acid both at position 34 and at position 84, relative to the human wild-type survivin polypeptide, and wherein the variant survivin polypeptide
is a subsequence (fragment) of the human wild-type survivin polypeptide (SEQ ID NO: 1).

8. A method for treating a malignancy, comprising administering to a subject in need of treatment an effective amount of:

(i) a variant survivin polypeptide, or
(ii) an expression construct comprising a nucleic acid sequence encoding the variant survivin polypeptide, and
(iii) an antigen presenting cell comprising the variant survivin polypeptide or the nucleic acid sequence encoding the variant survivin polypeptide,
wherein the variant survivin polypeptide comprises at least consecutive amino acids 16-87 (N-terminal zinc-binding baculovirus inhibitor of apoptosis protein repeat (BIR) domain) of the human wild-type survivin polypeptide (SEQ ID NO:1) modified to have an alanine both at position 34 and at position 84, relative to the human wild-type survivin polypeptide, and wherein the variant survivin polypeptide
is a subsequence (fragment) of the human wild-type survivin polypeptide (SEQ ID NO: 1),
wherein the malignancy is myeloma.

9. The method of claim 8, wherein the antigen presenting cells are cell is an autologous cell.

10. The method of claim 8, wherein the method further comprises conducting hematopoietic cell transplantation on the subject.

11. The method of claim 10, wherein the hematopoietic cell transplant is autologous.

12. The method of claim 8, wherein the variant survivin polypeptide comprises the amino acid sequence of SEQ ID NO:3.

* * * * *

```
                        SEQUENCE LISTING

<160> NUMBER OF SEQ ID NOS: 8

<210> SEQ ID NO 1
<211> LENGTH: 142
<212> TYPE: PRT
<213> ORGANISM: Homo sapiens

<400> SEQUENCE: 1

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Asp Pro Ile Glu Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Lys Lys Val Arg Arg Ala Ile Glu Gln Leu Ala Ala Met Asp
    130                 135                 140

<210> SEQ ID NO 2
<211> LENGTH: 142
<212> TYPE: PRT
<213> ORGANISM: Homo sapiens
<220> FEATURE:
<221> NAME/KEY: MISC_FEATURE
<222> LOCATION: (34)..(34)
<223> OTHER INFORMATION: Xaa is any amino acid other than threonine
<220> FEATURE:
<221> NAME/KEY: MISC_FEATURE
<222> LOCATION: (84)..(84)
<223> OTHER INFORMATION: Xaa is any amino acid other than cysteine

<400> SEQUENCE: 2

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Xaa Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60
```

```
Glu Gly Trp Glu Pro Asp Asp Pro Ile Glu His Lys Lys His
65                  70                  75                  80

Ser Ser Gly Xaa Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Lys Lys Val Arg Arg Ala Ile Glu Gln Leu Ala Ala Met Asp
    130                 135                 140
```

<210> SEQ ID NO 3
<211> LENGTH: 142
<212> TYPE: PRT
<213> ORGANISM: Homo sapiens

<400> SEQUENCE: 3

```
Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
                20                  25                  30

Cys Ala Pro Glu Arg Met Ala Glu Ala Gly Phe Ile His Cys Pro Thr
            35                  40                  45

Glu Asn Glu Pro Asp Leu Ala Gln Cys Phe Phe Cys Phe Lys Glu Leu
    50                  55                  60

Glu Gly Trp Glu Pro Asp Asp Pro Ile Glu His Lys Lys His
65                  70                  75                  80

Ser Ser Gly Ala Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Lys Lys Val Arg Arg Ala Ile Glu Gln Leu Ala Ala Met Asp
    130                 135                 140
```

<210> SEQ ID NO 4
<211> LENGTH: 45
<212> TYPE: DNA
<213> ORGANISM: Artificial
<220> FEATURE:
<223> OTHER INFORMATION: forward primer for the C84A survivin mutant

<400> SEQUENCE: 4
cataaaaagc attcgtccgg tgccgctttc ctttctgtca agaag         45

<210> SEQ ID NO 5
<211> LENGTH: 45
<212> TYPE: DNA
<213> ORGANISM: Artificial
<220> FEATURE:
<223> OTHER INFORMATION: forward primer for the C84A survivin mutant

<400> SEQUENCE: 5
cttcttgaca gaaaggaaag cggcaccgga cgaatgcttt ttatg         45

<210> SEQ ID NO 6
<211> LENGTH: 33
<212> TYPE: DNA
<213> ORGANISM: Artificial

```
<220> FEATURE:
<223> OTHER INFORMATION: forward primer for the T34A survivin mutant

<400> SEQUENCE: 6
gagggctgcg cctgcgcccc ggagcggatg gcc                                33

<210> SEQ ID NO 7
<211> LENGTH: 33
<212> TYPE: DNA
<213> ORGANISM: Artificial
<220> FEATURE:
<223> OTHER INFORMATION: forward primer for the T34A survivin mutant

<400> SEQUENCE: 7
ggccatccgc tccggggcgc aggcgcagcc ctc                                33

<210> SEQ ID NO 8
<211> LENGTH: 1190
<212> TYPE: DNA
<213> ORGANISM: Artificial
<220> FEATURE:
<223> OTHER INFORMATION: insert sequence

<400> SEQUENCE: 8
aagcttggta ccgagctcgg atccactagt aacggccgcc agtgtgctgg aattcatctg      60
tcgactgcta ccgccagatt tgaatcgcgg gacccgttgg cagaggtggc ggcggcggca     120
tgggtgcccc gacgttgccc cctgcctggc agcccttttct caaggaccac cgcatctcta   180
cattcaagaa ctggcccttc ttggagggct gcgcctgcgc cccggagcgg atggccgagg    240
ctggcttcat ccactgcccc actgagaacg agccagactt ggcccagtgt tcttctgct    300 tcaaggagct ggaaggctgg gagccagatg acgacccat agaggaacat aaaaagcatt     360
cgtccggtgc cgcttttcctt tctgtcaaga agcagtttga agaattaacc cttggtgaat    420
ttttgaaact ggacagagaa agagccaaga acaaaattgc aaaggaaacc aacaataaga    480
agaaagaatt tgaggaaact gcgaagaaag tgcgccgtgc catcgagcag ctggctgcca    540
tggattgagg cctctggccg gagctgcctg gtcccagagt ggctgcacca cttccagggt    600
ttattccctg gtgccaccag ccttcctgtg ggcccttag caatgtctta ggaaaggaga    660
tcaacatttt caaattagat gtttcaactg tgctcttgtt ttgtcttgaa agtggcacca     720
gaggtgcttc tgcctgtgca gcgggtgctg ctggtaacag tggctgcttc tctctctctc     780
tctctttttt gggggctcat ttttgctgtt ttgattcccg ggggatccta acatcgataa    840
aataaaagat tttatttagt ctccagaaaa aggggggaat gaaagacccc acctgtaggt     900
ttggcaagct agcttaagta acgccatttt gcaaggcatg gaaaatatca taactgagaa    960
tagagaagtt cagatcaagg tcaggaacag atggaacagc tgaatatggg ccaaacagga   1020
tatctgtggt aagcagttcc tgccccggct caggccaaga acagatggaa cagctgaata  1080
tgggccaaac aggatatctg tggtaagcag ttcctgcccc ggctcaggcc aagaacagat  1140
ggtcccagat tgcggtccag ccctcagcag tttctaagat agatatccga              1190
```